(12) United States Patent
Polizzotti et al.

(10) Patent No.: US 11,147,890 B2
(45) Date of Patent: Oct. 19, 2021

(54) STIMULI-RESPONSIVE PARTICLES ENCAPSULATING A GAS AND METHODS OF USE

(71) Applicant: Children's Medical Center Corporation, Boston, MA (US)

(72) Inventors: Brian D. Polizzotti, Swampscott, MA (US); Yifeng Peng, Newton, MA (US); John Kheir, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 99 days.

(21) Appl. No.: 16/489,541

(22) PCT Filed: Feb. 28, 2018

(86) PCT No.: PCT/US2018/020305
§ 371 (c)(1),
(2) Date: Aug. 28, 2019

(87) PCT Pub. No.: WO2018/160752
PCT Pub. Date: Sep. 7, 2018

(65) Prior Publication Data
US 2020/0009065 A1    Jan. 9, 2020

Related U.S. Application Data

(60) Provisional application No. 62/596,959, filed on Dec. 11, 2017, provisional application No. 62/465,109, filed on Feb. 28, 2017.

(51) Int. Cl.
| | | |
|---|---|---|
| A61K 49/22 | (2006.01) | |
| A61K 9/50 | (2006.01) | |
| A61K 9/51 | (2006.01) | |
| A23L 33/10 | (2016.01) | |
| A61P 7/00 | (2006.01) | |
| A61P 9/04 | (2006.01) | |
| A23B 7/157 | (2006.01) | |
| A61K 8/02 | (2006.01) | |
| A61K 8/22 | (2006.01) | |
| A61K 9/00 | (2006.01) | |
| A61K 9/08 | (2006.01) | |
| A61K 9/107 | (2006.01) | |
| A61K 33/00 | (2006.01) | |
| A61K 45/06 | (2006.01) | |
| A61Q 19/00 | (2006.01) | |
| B01J 13/08 | (2006.01) | |
| B01J 13/20 | (2006.01) | |
| C02F 1/24 | (2006.01) | |
| C10L 1/12 | (2006.01) | |
| C12M 1/00 | (2006.01) | |
| A61K 41/00 | (2020.01) | |
| C02F 101/32 | (2006.01) | |

(52) U.S. Cl.
CPC ............ *A61K 49/223* (2013.01); *A23B 7/157* (2013.01); *A23L 33/10* (2016.08); *A61K 8/0279* (2013.01); *A61K 8/22* (2013.01); *A61K 9/0019* (2013.01); *A61K 9/08* (2013.01); *A61K 9/107* (2013.01); *A61K 9/5036* (2013.01); *A61K 9/5089* (2013.01); *A61K 9/5161* (2013.01); *A61K 9/5192* (2013.01); *A61K 33/00* (2013.01); *A61K 41/0047* (2013.01); *A61K 45/06* (2013.01); *A61P 7/00* (2018.01); *A61P 9/04* (2018.01); *A61Q 19/00* (2013.01); *B01J 13/08* (2013.01); *B01J 13/206* (2013.01); *C02F 1/24* (2013.01); *C10L 1/1208* (2013.01); *C12M 29/00* (2013.01); *A23V 2002/00* (2013.01); *C02F 2101/32* (2013.01); *C10L 2230/22* (2013.01); *C10L 2250/04* (2013.01); *C10L 2250/06* (2013.01); *C10L 2270/026* (2013.01)

(58) Field of Classification Search
None
See application file for complete search history.

(56) References Cited

U.S. PATENT DOCUMENTS

| | | |
|---|---|---|
| 3,526,481 A | 9/1970 | Rubricius et al. |
| 4,276,885 A | 7/1981 | Tickner et al. |
| 4,446,642 A | 5/1984 | Chap |
| 4,466,442 A | 8/1984 | Hilmann et al. |
| 4,844,882 A | 7/1989 | Widder et al. |
| 4,911,689 A | 3/1990 | Hattler |
| 5,084,011 A | 1/1992 | Grady |
| 5,219,538 A | 6/1993 | Henderson et al. |

(Continued)

FOREIGN PATENT DOCUMENTS

| | | |
|---|---|---|
| EP | 0077752 A2 | 4/1983 |
| EP | 0 699 445 A2 | 3/1996 |

(Continued)

OTHER PUBLICATIONS

Invitation to Pay Additional Fees dated Apr. 23, 2018 for PCT/US2018/020305.

(Continued)

*Primary Examiner* — Jennifer Lamberski
(74) *Attorney, Agent, or Firm* — Wolf, Greenfield & Sacks, P.C.

(57) ABSTRACT

Provided herein are various gas-filled particles having a stimuli-responsive shell encapsulating the gas. The stimuli-responsive shell comprises one or more release triggers. Compositions for medical or non-medical applications, methods of use and treatment, and methods of preparation are also described.

6 Claims, 39 Drawing Sheets

(56) References Cited

U.S. PATENT DOCUMENTS

| | | |
|---|---|---|
| 5,487,390 A | 1/1996 | Cohen et al. |
| 5,558,094 A | 9/1996 | Quay |
| 5,573,751 A | 11/1996 | Quay |
| 5,665,383 A | 9/1997 | Grinstaff et al. |
| 5,711,933 A | 1/1998 | Bichon et al. |
| 5,733,572 A | 3/1998 | Unger et al. |
| 5,827,504 A | 10/1998 | Yan et al. |
| 5,840,275 A | 11/1998 | Bichon et al. |
| 5,863,520 A | 1/1999 | Bichon et al. |
| 5,869,538 A | 2/1999 | Van Liew et al. |
| 5,882,717 A | 3/1999 | Panesar et al. |
| 5,935,553 A | 8/1999 | Unger et al. |
| 6,045,777 A | 4/2000 | Church et al. |
| 6,200,548 B1 | 3/2001 | Bichon et al. |
| 6,210,611 B1 | 4/2001 | Needham et al. |
| 6,261,537 B1 | 7/2001 | Klaveness et al. |
| 6,315,981 B1 | 11/2001 | Unger |
| 6,333,021 B1 | 12/2001 | Schneider et al. |
| 6,416,740 B1 | 7/2002 | Unger |
| 6,443,898 B1 | 9/2002 | Unger et al. |
| 6,537,246 B1 | 3/2003 | Unger et al. |
| 6,808,720 B2 | 10/2004 | Unger |
| 6,844,317 B2 | 1/2005 | Winslow et al. |
| 7,105,151 B2 | 9/2006 | Unger et al. |
| 7,122,027 B2 | 10/2006 | Trescony et al. |
| 7,141,235 B2 | 11/2006 | Trevino et al. |
| 7,303,156 B1 | 12/2007 | Kim et al. |
| 8,481,077 B2 | 7/2013 | Kheir et al. |
| 10,357,450 B2 | 7/2019 | Kheir et al. |
| 10,577,554 B2 | 3/2020 | Kheir et al. |
| 2002/0155098 A1 | 10/2002 | Bolton |
| 2003/0120204 A1 | 6/2003 | Unger et al. |
| 2004/0013662 A1 | 1/2004 | Porter et al. |
| 2005/0260189 A1 | 11/2005 | Klibanov et al. |
| 2006/0051297 A1 | 3/2006 | Schneider et al. |
| 2007/0134332 A1 | 6/2007 | Turnell et al. |
| 2008/0226750 A1 | 9/2008 | Roth et al. |
| 2009/0191244 A1 | 7/2009 | Kheir et al. |
| 2010/0069814 A1 | 3/2010 | Borgia et al. |
| 2010/0080759 A1 | 4/2010 | Chang et al. |
| 2010/0158813 A1 | 6/2010 | Paradossi et al. |
| 2010/0209532 A1 | 8/2010 | Dube et al. |
| 2011/0207062 A1 | 8/2011 | McAlister |
| 2012/0156300 A1 | 6/2012 | Kheir et al. |
| 2012/0175305 A1 | 7/2012 | Borden et al. |
| 2012/0201900 A1 | 8/2012 | Borden et al. |
| 2013/0066264 A1 | 3/2013 | Matsumoto et al. |
| 2014/0010848 A1 | 1/2014 | Kheir et al. |
| 2014/0057108 A1 | 2/2014 | Sun et al. |
| 2015/0164787 A1 | 6/2015 | Kheir et al. |
| 2016/0030596 A1 | 2/2016 | Kheir et al. |
| 2016/0067276 A1 | 3/2016 | Polizzotti et al. |
| 2019/0388337 A1 | 12/2019 | Kheir et al. |

FOREIGN PATENT DOCUMENTS

| | | | |
|---|---|---|---|
| EP | 0 605 477 B2 | 6/2007 | |
| EP | 2 253 308 A1 | 11/2010 | |
| WO | WO 92/05806 A1 | 4/1992 | |
| WO | WO 92/17514 A1 | 10/1992 | |
| WO | WO 94/18954 A1 | 9/1994 | |
| WO | WO 94/28874 A1 | 12/1994 | |
| WO | WO 95/16467 A1 | 6/1995 | |
| WO | WO 97/00638 A2 | 1/1997 | |
| WO | WO 97/22409 A1 | 6/1997 | |
| WO | WO 98/18501 A2 | 5/1998 | |
| WO | WO 2004/069284 A2 | 8/2004 | |
| WO | WO 2005/063305 A1 | 7/2005 | |
| WO | WO 2009/043031 A2 | 4/2009 | |
| WO | WO 2009/082449 A2 | 7/2009 | |
| WO | WO 2011/013032 A2 | 2/2011 | |
| WO | WO 2011/034892 A2 | 3/2011 | |
| WO | WO 2012/065060 A2 | 5/2012 | |
| WO | WO-2014143808 A1 * | 9/2014 | A61K 9/5031 |
| WO | WO 2015/196065 A1 | 12/2015 | |

OTHER PUBLICATIONS

International Search Report and Written Opinion dated Jun. 25, 2018 for PCT/US2018/020305.

International Preliminary Report on Patentability dated Sep. 12, 2019 for PCT/US2018/020305.

[No Author Listed], Acute Myocardial Infarction with HyperOxemic Therapy II (AMIHOT II). Clinical Trials.gov. Last Accessed from http://clinicaltrials.gov/ct2/show/NCT00175058?tern=therox &rank=1 on Nov. 9, 2010. 5 pages.

[No Author Listed], DownStream System. Therox. Last Accessed from http://www.therox.com/products/downstream-system/index.cfm?print on Nov. 9, 2010. 1 page.

Adjei et al., Pulmonary delivery of peptide drugs: effect of particle size on bioavailability of leuprolide acetate in healthy male volunteers. Pharm Res. Jun. 1990;7(6):565-9.

Asai et al., Interaction of soybean oil with phosphatidylcholine and their formation of small dispersed particles. Drug Dev Ind Pharm. May 1999;25(5):643-50.

Baker et al., Hypothermia prevents ischemia-induced increases in hippocampal glycine concentrations in rabbits. Stroke. May 1991;22(5):666-73.

Barnhart et al., Characteristics of Albunex: air-filled albumin microspheres for echocardiography contrast enhancement. Invest Radiol. Sep. 1990;25 Suppl 1:S162-4.

Batchelor et al., The determination of the bulk stress in a suspension of spherical particles to order c2. J Fluid Mech. 1972;56(3):401-27.

Bauer et al., Perfluorocarbon-filled poly(lactide-co-gylcolide) nano- and microcapsules as artificial oxygen carriers for blood substitutes: a physico-chemical assessment. J Microencapsul. 2010;27(2):122-32. doi: 10.3109/02652040903052002.

Bertrand et al., Photo-responsive polymers: synthesis and applications. Polym. Chem. 2017, 8: 52-73.

Bisazza et al., Microbubble-mediated oxygen delivery to hypoxic tissues as a new therapeutic device. Conf Proc IEEE Eng Med Biol Soc. 2008;2008:2067-70.

Borden et al., Oxygen permeability of fully condensed lipid monolayers. J Phys Chem. 2004:108(19):6009-16.

Borden et al., A stimulus-responsive contrast agent for ultrasound molecular imaging. Biomaterials. Feb. 2008;29(5):597-606. Epub Oct. 30, 2007.

Borden et al., Dissolution behavior of lipid monolayer-coated, air filled microbubbles: Effect of lipid hydrophobic chain length. Langmuir. 2002;18(24):9225-33.

Borden et al., Influence of lipid shell physicochemical properties on ultrasound-induced microbubble destruction. IEEE Trans Ultrason Ferroelectr Freq Control. Nov. 2005;52(11):1992-2002.

Borden et al., Lateral phase separation in lipid-coated microbubbles. Lateral phase separation in lipid-coated microbubbles. Langmuir. Apr. 25, 2006;22(9):4291-7.

Borden et al., Physico-chemical properties of the microbubble lipid shell. IEEE Transactions on Ultrasonics Ferroelectrics and Frequency Control, Montreal, Canada (2004).

Borden et al., Surface phase behavior and microstructure of lipid/PEG-emulsifier monolayer-coated microbubbles. Colloids Surf B Biointerfaces. Jun. 1, 2004;35(3-4):209-23.

Brancewicz et al., Hydrophobic gas bubble formation in definity (R): a freeze fracture electron microscopy study. J Dispersion Sci Tech. 2006;27(5):761-5.

Brezis et al., Hypoxia of the renal medulla—its implications for disease. N Engl J Med. Mar. 9, 1995;332(10):647-55.

Bucana et al., Preservation of multilamellar lipid vesicles (liposomes) for ultrastructural studies. Scan Electron Microsc. 1983;(Pt 3):1329-37.

Burkhard et al., Oxygen transport to tissue by persistent bubbles: theory and simulations. J Appl Physiol. 1994;77(6):2874-8.

Cabrales et al., Early difference in tissue pH and microvascular hemodynamics in hemorrhagic shock resuscitation using polyethylene glycol-albumin- and hydroxyethyl starch-based plasma expanders. Shock. Jul. 2005;24(1):66-73.

Cabrales et al., Extreme hemodilution with PEG-hemoglobin vs. PEG-albumin. Am J Physiol Heart Circ Physiol. Dec. 2005;289(6):H2392-400. Epub Jul. 15, 2005.

(56) References Cited

OTHER PUBLICATIONS

Choi et al., Liposomes and niosomes as topical drug delivery systems. Skin Pharmacol Physiol. Sep.-Oct. 2005;18(5):209-19. Epub Jul. 5, 2005.
Choi et al., Noninvasive, transcranial and localized opening of the blood-brain barrier using focused ultrasound in mice. Ultrasound Med Biol. Jan. 2007;33(1):95-104.
Cortesi et al., Sugar cross-linked gelatin for controlled release: microspheres and disks. Biomaterials. Sep. 1998;19(18):1641-9.
Cravotto et al., On the mechanochemical activation by ultrasound. Chem Soc Rev. Sep. 21, 2013;42(18):7521-34. doi: 10.1039/c2cs35456j.
Davis et al., Topical oxygen emulsion: a novel wound therapy. Arch Dermatol. Oct. 2007;143(10):1252-6.
De Jong et al., Basic acoustic properties of microbubbles. Echocardiography. Apr. 2002;19(3):229-40.
Dewall et al., A simple, expendable, artificial oxygenator for open heart surgery. Surg Clin North Am. Aug. 1956:1025-34.
Diebel et al., Right ventricular response after myocardial contusion and hemorrhagic shock. Surgery. Oct. 1993;114(4):788-92; discussion 793.
Dressaire et al., Interfacial polygonal nanopatterning of stable microbubbles. Science. May 30, 2008;320(5880):1198-201.
Dubourg et al., Failure of the loop diuretic torasemide to improve renal function of hypoxemic vasomotor nephropathy in the newborn rabbit. Pediatr Res. Apr. 2000;47(4 Pt 1):504-8.
Duncan et al., Test of the Epstein-Plesset model for gas microparticle dissolution in aqueous media: effect of surface tension and gas undersaturation in solution. Langmuir. Mar. 30, 2004;20(7):2567-78.
Elberger et al., Double-labeling of tissue containing the carbocyanine dye DiI for immunocytochemistry. J Histochem Cytochem. May 1990;38(5):735-9.
El-Desoky et al., Effect of graded hypoxia on hepatic tissue oxygenation measured by near infrared spectroscopy. J Hepatol. Jul. 1999;31(1):71-6.
Epstein et al., On the stability of gas bubbles in liquid-gas solutions. J Chem Phys. 1950;18(11):1505-9.
Farook et al., Microbubbling by co-axial electrohydrodynamic atomization. Med Biol Eng Comput. Aug. 2007;45(8):781-9. Epub Jul. 12, 2007.
Farook et al., Preparation of microbubble suspensions by co-axial electrohydrodynamic atomization. Med Eng Phys. Sep. 2007;29(7):749-54. Epub Oct. 10, 2006.
Feinstein et al., Microbubble dynamics visualized in the intact capillary circulation. J Am Coll Cardiol. Sep. 1984;4(3):595-600.
Feinstein, The powerful microbubble: from bench to bedside, from intravascular indicator to therapeutic delivery system, and beyond. Am J Physiol Heart Circ Physiol. Aug. 2004;287(2):H450-7.
Ferenz et al., Safety of poly (ethylene glycol)-coated perfluorodecalin-filled poly (lactide-co-glycolide) microcapsules following intravenous administration of high amounts in rats. Results Pharma Sci. Apr. 30, 2014;4:8-18. doi: 10.1016/j.rinphs.2014.04.001. eCollection 2014.
Ferrara et al., Ultrasound microbubble contrast agents: fundamentals and application to gene and drug delivery. Annu Rev Biomed Eng. 2007;9:415-47.
Ferreira et al., Cellulose carboxylate/tosylate mixed esters: Synthesis, properties and shaping into microspheres. Carbohydr Polym. Nov. 5, 2016;152:79-86. doi: 10.1016/j.carbpol.2016.06.075. Epub Jun. 18, 2016.
Feshitan et al., Microbubble size isolation by differential centrifugation. J Colloid Interface Sci. Jan. 15, 2009;329(2):316-24. doi: 10.1016/j.jcis.2008.09.066. Epub Oct. 1, 2008.
Feshitan et al., Systemic oxygen delivery by peritoneal perfusion of oxygen microbubbles. Biomaterials. Mar. 2014;35(9):2600-6. doi: 10.1016/j.biomaterials.2013.12.070. Epub Jan. 15, 2014.
Fuchs et al., Ischemic hepatitis: clinical and laboratory observations of 34 patients. J Clin Gastroenterol. Apr. 1998;26(3):183-6.
Gerber et al., Long lived microbubbles for oxygen delivery. Artif Cells Blood Substit Immobil Biotechnol. 2007;35(1):119-24.
Goh et al., Alginates as a useful natural polymer for microencapsulation and therapeutic applications. Carbohydrate Polymers. Mar. 17, 2012; 88(1):1-12.
Hansel et al., Metabolic syndrome is associated with elevated oxidative stress and dysfunctional dense high-density lipoprotein particles displaying impaired antioxidative activity. J Clin Endocrinol Metab. Oct. 2004;89(10):4963-71.
Hattler et al., A respiratory gas exchange catheter: in vitro and in vivo tests in large animals. J Thorac Cardiovasc Surg. Sep. 2002;124(3):520-30.
Hernot et al., Microbubbles in ultrasound-triggered drug and gene delivery. Adv Drug Deliv Rev. Jun. 30, 2008;60(10):1153-66. Epub Apr. 3, 2008.
Hornig et al., Synthetic polymeric nanoparticles by nanoprecipitation. J. Mater. Chem. 19, 3838-3840; 2009.
Jones et al., Demonstration of nonperfused myocardium in late hemorrhagic shock. Circ Shock. 1978;5(2):97-104.
Karlsson et al., Dynamics of hepatic enzyme activity following birth asphyxia. Acta Paediatr. Nov. 2006;95(11):1405-11.
Kaya et al., Changes in lipid-encapsulated microbubble population during continuous infusion and methods to maintain consistency. Ultrasound Med Biol. Oct. 2009;35(10):1748-55. doi: 10.1016/j.ultrasmedbio.2009.04.023. Epub Jul. 26, 2009.
Kheir et al., Bulk manufacture of concentrated oxygen gas-filled microparticles for intravenous oxygen delivery. Adv Healthc Mater. Aug. 2013;2(8):1131-41. doi: 10.1002/adhm.201200350. Epub Mar. 8, 2013.
Kheir et al., Novel oxygen-bearing nanoparticles provide dose-dependent oxygen delivery. Critic Care Medic. 2007;35(12):A16-16.
Kheir et al., Oxygen gas-filled microparticles provide intravenous oxygen delivery. Sci Transl Med. Jun. 27, 2012;4(140):140ra88. doi: 10.1126/scitranslmed.3003679.
Kim et al., Artificial oxygen carriers as red blood cell substitutes: a selected review and current status. Artif Organs. Sep. 2004;28(9):813-28.
Kim et al., Mechanical properties and microstructure of polycrystalline phospholipid monolayer shells: novel solid microparticles. Langmuir. 2003;19(20):8455-66.
Kim et al., New protocols for preparing dipalmitoylphosphatidylcholine dispersions and controlling surface tension and competitive adsorption with albumin at the air/aqueous interface. Colloids Surf B Biointerfaces. Jul. 10, 2005;43(3-4):256-66.
Kim, Mechanical properties, microstructure, and specific adhesion of phospholipid monolayer-coated microbubbles. Ph.D. Dissertation, Duke University, (1999).
Klemcke et al., Is survival time after hemorrhage a heritable, quantitative trait?: an initial assessment. Shock. Jun. 2008;29(6):748-53.
Klibanov et al., Amphipathic polyethyleneglycols effectively prolong the circulation time of liposomes. FEBS Lett. Jul. 30, 1990;268(1):235-7.
Klibanov et al., Ultrasound contrast agents: development of the field and current status. Topics Curr Chem. 2002;222:1-34.
Kocak et al., Butun, pH-Responsive polymers. Polym. Chem. 8, 144-176 ; 2017.
Kohane et al., A re-examination of tetrodotoxin for prolonged duration local anesthesia. Anesthesiology. Jul. 1998;89(1):119-31.
Kohane et al., Sciatic nerve blockade in infant, adolescent, and adult rats: a comparison of ropivacaine with bupivacaine. Anesthesiology. Nov. 1998;89(5):1199-208; discussion 10A.
Korin et al., Shear-activated nanotherapeutics for drug targeting to obstructed blood vessels. Science. Aug. 10, 2012;337(6095):738-42. doi: 10.1126/science.1217815. Epub Jul. 5, 2012. Erratum in: Science. Sep. 21, 2012;337(6101):1453.
Kuhl et al., Modulation of interaction forces between bilayers exposing short-chained ethylene oxide headgroups. Biophys J. May 1994;66(5):1479-88.

(56) References Cited

OTHER PUBLICATIONS

Kutscher et al., Threshold size for optimal passive pulmonary targeting and retention of rigid microparticles in rats. J Control Release. Apr. 2, 2010;143(1):31-7. doi: 10.1016/j.jconrel.2009.12.019. Epub Jan. 5, 2010.
Kvale et al., Size fractionation of gas-filled microspheres by flotation. Separations Technol. 1996;6(4):219-26.
Laine et al., Polyethylene glycol nephrotoxicity secondary to prolonged high-dose intravenous lorazepam. Ann Pharmacother. Nov. 1995;29(11):1110-4.
Ledingham, Heart failure in experimental refractory shock. Eur J Intensive Care Med. Nov. 1976;2(3):111-7.
Leonov et al., Extending the golden hour of hemorrhagic shock tolerance with oxygen plus hypothermia in awake rats. An exploratory study. Resuscitation. Feb. 2002;52(2):193-202.
Li et al., Acoustic emulsification Part 1. Instability of oil-water interface to form initial droplets. J Fluid Mech. 1978;88(Oct.):499-511.
Li et al., Acoustic Emulsification Part 2. Breakup of large primary oil droplets in a water medium. J Fluid Mech. 1978;88(Oct.):513-28.
Liebert et al., Nanoparticles on the basis of highly functionalized dextrans. J Am Chem Soc. Aug. 3, 2005;127(30):10484-5.
Lindner, Microbubbles in medical imaging: current applications and future directions. Nat Rev Drug Discov. Jun. 2004;3(6):527-32.
Lum et al., Ultrasound radiation force enables targeted deposition of model drug carriers loaded on microbubbles. J Control Release. Mar. 10, 2006;111(1-2):128-34. Epub Dec. 27, 2005.
Lundgren et al., Intravascular fluorocarbon-stabilized microbubbles protect against fatal anemia in rats. Artif Cells Blood Substit Immobil Biotechnol. 2006;34(5):473-86.
Masters et al., Prolonged regional nerve blockade by controlled release of local anesthetic from a biodegradable polymer matrix. Anesthesiology. Aug. 1993;79(2):340-6.
McLure et al., Review of local anesthetic agents. Minerva Anestesiol. Mar. 2005;71(3):59-74.
Meade et al., Ventilation strategy using low tidal volumes, recruitment maneuvers, and high positive end-expiratory pressure for acute lung injury and acute respiratory distress syndrome: a randomized controlled trial. JAMA. Feb. 13, 2008;299(6):637-45.
Meure et al., Conventional and dense gas techniques for the production of liposomes: a review. AAPS PharmSciTech. 2008;9(3):798-809. doi: 10.1208/s12249-008-9097-x. Epub Jul. 3, 2008.
Mezzetti et al., Oxidative stress and cardiovascular complications in diabetes: isoprostanes as new markers on an old paradigm. Cardiovasc Res. Aug. 18, 2000;47(3):475-88.
Mulholland et al., Investigation and quantification of the blood trauma caused by the combined dynamic forces experienced during cardiopulmonary bypass. Perfusion. Nov. 2000;15(6):485-94.
Nakahata et al., pH- and sugar-responsive gel assemblies based on boronate-catechol interactions. ACS Macro Lett. 2014, 3: 337-340.
O'Neill et al., Acute Myocardial Infarction with Hyperoxemic Therapy (AMIHOT): a prospective, randomized trial of intracoronary hyperoxemic reperfusion after percutaneous coronary intervention. J Am Coll Cardiol. Jul. 31, 2007;50(5):397-405. Epub Jul. 16, 2007.
Paefgen et al., Evolution of contrast agents for ultrasound imaging and ultrasound-mediated drug delivery. Front Pharmacol. Sep. 15, 2015;6:197. doi: 10.3389/fphar.2015.00197. eCollection 2015.
Pancholi et al., Generation of microbubbles for diagnostic and therapeutic applications using a novel device. J Drug Target. Jul. 2008;16(6):494-501. doi: 10.1080/10611860802184884.
Pancholi et al., Novel methods for preparing phospholipid coated microbubbles. Eur Biophys J. Apr. 2008;37(4):515-20. Epub Aug. 9, 2007.
Pekkanen et al., Nanoparticle enhanced optical imaging and phototherapy of cancer. J Biomed Nanotechnol. Sep. 2014;10(9):1677-712.
Peng et al., Interfacial Nanoprecipitation toward Stable and Responsive Microbubbles and Their Use as a Resuscitative Fluid. Angew Chem Int Ed Engl. Jan. 26, 2018;57(5):1271-1276. doi: 10.1002/anie.201711839. Epub Jan. 2, 2018.
Phong et al., Properties and hydrolysis of PLGA and PLLA cross-linked with electron beam radiation. Polymer degradation and Stability 95; 95(2010)771-777.
Pu et al., Collapse and shedding transitions in binary lipid monolayers coating microbubbles. Langmuir. Mar. 28, 2006;22(7):2993-9.
Pu et al., Effect of microstructure on molecular oxygen permeation through condensed phospholipid monolayers. J Am Chem Soc. May 11, 2005;127(18):6524-5.
Rodriguez et al., Generation of microbubbles with applications to industry and medicine. Annu. Rev. Fluid Mech. 47, 405-429 (2015).
Ryter et al., Heme oxygenase-1/carbon monoxide: from basic science to therapeutic applications. Physiol Rev. Apr. 2006;86(2):583-650.
Sagi et al., Self-immolative polymers. J Am Chem Soc. Apr. 23, 2008;130(16):5434-5. doi: 10.1021/ja801065d. Epub Apr. 1, 2008.
Sakai et al., Hemoglobin-vesicles as oxygen carriers: influence on phagocytic activity and histopathological changes in reticuloendothelial system. Am J Pathol. Sep. 2001;159(3):1079-88.
Scholz, Mechanisms of (local) anaesthetics on voltage-gated sodium and other ion channels. Br J Anaesth. Jul. 2002;89(1):52-61.
Schubert et al., Using microbubbles to oxygenate blood: possible? Engineering in Medicine and Biology Society, 2003. Proceedings of the 25" Annual International Conference of the IEEE, 1(1721):431-34 (2003).
Seekell et al., Oxygen delivery using engineered microparticles. Proc Natl Acad Sci U S A. Nov. 1, 2016;113(44):12380-12385. Epub Oct. 17, 2016.
Sevitt, A review of the complications of burns, their origin and importance for illness and death. J Trauma. May 1979;19(5):358-69. Abstract Only.
Silvay et al., Cardiopulmonary bypass for adult patients: a survey of equipment and techniques. J Cardiothorac Vasc Anesth. Aug. 1995;9(4):420-4.
Sirsi et al., Microbubble Compositions, Properties and Biomedical Applications. Bubble Sci Eng Technol. Nov. 2009;1(1-2):3-17.
Span et al., Engineered microparticles delivering oxygen to enhance radiotherapy efficacy. Proc Natl Acad Sci U S A. Dec. 13, 2016;113(50):E8009. Epub Dec. 7, 2016.
Spiess, Perfluorocarbon emulsions as a promising technology: a review of tissue and vascular gas dynamics. J Appl Physiol (1985). Apr. 2009;106(4):1444-52. doi: 10.1152/japplphysiol.90995.2008. Epub Jan. 29, 2009.
Stieger et al., Enhancement of vascular permeability with low-frequency contrast-enhanced ultrasound in the chorioallantoic membrane model. Radiology. Apr. 2007;243(1):112-21.
Suslick et al., Acoustic Cavitation and Its Chemical Consequences. Phil. Trans. Roy. Soc. A. 1999;357:335-353.
Swanson et al., Phospholipid-stabilized microbubble foam for injectable oxygen delivery. Langmuir. Oct. 19, 2010;26(20):15726-9. doi: 10.1021/la1029432.
Takalkar et al., Binding and detachment dynamics of microbubbles targeted to P-selectin under controlled shear flow. J Control Release. May 18, 2004;96(3):473-82.
Takasu et al., Effects of increased oxygen breathing in a volume controlled hemorrhagic shock outcome model in rats. Resuscitation. Aug. 1, 2000;45(3):209-20.
Talu et al., Lipid-stabilized monodispersed microbubbles produced by flow focusing for use as ultrasound contrast agents. Ultrasonics Symposium, 2006 IEEE. 2006;2-6:1568-71.
Talu et al., Long-term stability by lipid coating monodisperse microbubbles formed by a flow-focusing device. Langmuir. Nov. 7, 2006;22(23):9487-90.
Talu et al., Maintaining monodispersity in a microbubble population formed by flow-focusing. Langmuir. Mar. 4, 2008;24(5):1745-9. Epub Jan. 19, 2008.
Talu et al., Tailoring the size distribution of ultrasound contrast agents: possible method for improving sensitivity in molecular imaging. Mol Imaging. Nov.-Dec. 2007;6(6):384-92.
Tayar et al., Severe hyperosmolar metabolic acidosis due to a large dose of intravenous lorazepam. N Engl J Med. Apr. 18, 2002;346(16):1253-4.

(56) References Cited

OTHER PUBLICATIONS

Taylor, Ostwald ripening in emulsions. Advances in Colloid and Interface Science. 1998;75(2):107-63.

Teraphongphom et al., Nanoparticle Loaded Polymeric Microbubbles as Contrast Agents for Multimodal Imaging. Langmuir. Nov. 3, 2015;31(43):11858-67. doi: 10.1021/acs.langmuir.5b03473. Epub Oct. 16, 2015.

Tracy et al., A method to fix lipids for staining fat embolism in paraffin sections. Histopathology. Jul. 2002;41(1):75-9.

Tsao et al., Enzyme-Degradable Hybrid Polymer/Silica Microbubbles as Ultrasound Contrast Agents. Langmuir. Jun. 28, 2016;32(25):6534-43. doi: 10.1021/acs.langmuir.6b01075. Epub Jun. 16, 2016.

Unger et al., Acoustically active liposheres containing paclitaxel: a new therapeutic ultrasound contrast agent. Invest Radiol. Dec. 1998;33(12):886-92.

Unger et al., Therapeutic applications of lipid-coated microbubbles. Adv Drug Deliv Rev. May 7, 2004;56(9):1291-314.

Vercherat et al., Stra13 regulates oxidative stress mediated skeletal muscle degeneration. Hum Mol Genet. Nov. 15, 2009;18(22):4304-16. doi: 10.1093/hmg/ddp383. Epub Aug. 13, 2009.

Wheatley et al., Surfactant-stabilized contrast agent on the nanoscale for diagnostic ultrasound imaging. Ultrasound Med Biol. Jan. 2006;32(1):83-93.

Winslow et al., Comparison of PEG-modified albumin and hemoglobin in extreme hemodilution in the rat. J Appl Physiol. Oct. 2004;97(4):1527-34. Epub Jun. 18, 2004.

Wu et al., Ultrasound, cavitation bubbles and their interaction with cells. Adv Drug Deliv Rev. Jun. 30, 2008;60(10):1103-16. Epub Apr. 8, 2008.

Xiong et al., Polymeric microbubbles for ultrasonic molecular imaging and targeted therapeutics. J Biomater Sci Polym Ed. 2011;22(4-6):417-28. doi: 10.1163/092050610X540440.

Xu et al., Controllable gas-liquid phase flow patterns and monodisperse microbubbles in a microfluidic T-junction device. Applied Physics Letters. 2006;88(13).

Zagorski et al., Chemokines accumulate in the lungs of rats with severe pulmonary embolism induced by polystyrene microspheres. J Immunol. Nov. 15, 2003;171(10):5529-36.

Zanen et al., The optimal particle size for parasympathicolytic aerols in mild asthmatics. Int J Pharm. 1995;114:111-5.
Zhao et al., Preparation, characterization and in vivo observation of phospholipid-based gas-filled microbubbles containing hirudin. Ultrasound Med Biol. Sep. 2005;31(9):1237-43.
Zhao et al., Radiation-force assisted targeting facilitates ultrasonic molecular Imaging. Mol Imaging. Jul. 2004;3(3):135-48.
Semple et al., Influence of cholesterol on the association of plasma proteins with liposomes. Biochemistry. 1996;35(8):2521-2525. doi:10.1021/bi950414i.

* cited by examiner

STIMULI-RESPONSIVE PARTICLES ENCAPSULATING A GAS AND METHODS OF USE

RELATED APPLICATIONS

This application is a national stage filing under 35 U.S.C. § 371 of international application number PCT/US2018/020305, filed Feb. 28, 2018, which claims the benefit under 35 U.S.C. § 119 of U.S. Provisional Application No. 62/465,109, filed Feb. 28, 2017, and U.S. Provisional Application No. 62/596,959, filed Dec. 11, 2017, the entire contents of each of which are incorporated herein by reference.

FEDERALLY SPONSORED RESEARCH

This invention was made with government support under Grant no. HL119145, awarded by The National Institutes of Health; and under Grant nos. W81XWH-15-1-0544 and W81XWH-11-2-0041, awarded by the U.S. Department of the Army. The government has certain rights in the invention.

BACKGROUND

All human cells require a constant oxygen supply to maintain cellular structure and function. When oxygen delivery decreases below Pasteur's point, cells undergo anaerobic respiration. Clinically, this can lead to critical organ dysfunction (e.g., brain and myocardial injury), which could result in death if not rapidly corrected. Impairments in oxygen supply can occur during airways obstruction, parenchymal lung disease, or impairments in pulmonary blood flow, circulation, blood oxygen content, and oxygen uptake. Brief interruptions in ventilation or pulmonary blood flow can cause profound hypoxemia, leading to organ injury and death in critically ill subjects.

Providing even a small amount of oxygen supply may significantly reduce the death rate or the severity of tissue damage in subjects suffering from hypoxia. One conventional attempt to restore the oxygen level in a patient is supportive therapy of patient's respiratory system (e.g., mechanical ventilation). This approach may be insufficient to fully reverse hypoxemia in patients with lung injury. Emergency efforts such as lung recruitment maneuvers, increased fraction of inspired oxygen or inhalational nitric oxide are other approaches used to deliver oxygen to a patient. However, in some instances these may be inadequate and/or require too long to take effect due to lack of an adequate airway or overwhelming lung injury.

SUMMARY

Previous work has established the possibility of encapsulating a gas, such as oxygen, in a microbubble with a lipid outer membrane and a gas core for therapeutic delivery of the gas to a subject. For example, previous work has established that administering to asphyxial subjects oxygen-filled microparticles via intravenous injection successfully restores oxygen supply in the subject, preserves spontaneous circulation during asphyxia, and reduces occurrence of cardiac arrest. When administered to the subject, the lipid particles were able to immediately release the gas core into the blood based on the properties of the lipid outer membrane. See, e.g., US Publication No. 2009/0191244 and PCT Application Publication No. WO 2012/065060, incorporated herein by reference.

It was discovered, quite surprisingly, according to one aspect of the invention, that stabilized particles encapsulating one or more gases in a stimuli-responsive shell such as a stimuli-responsive polymeric shell are useful in various medical and non-medical applications, for example, for delivering gas to a subject for therapeutic and diagnostic purposes. In addition to therapeutic and diagnostic utilities, the particles of the invention may be useful in a number of other settings. For instance the particles may be used as additives in cosmetic and personal care formulations for viscosity enhancer, color modulation, gas carriers, etc., additives in food products and beverages, for delivery of ozone gas as antimicrobial, or pesticides, for water treatment e.g., pesticide removal, bioremediation, etc., as thernostics; Plasmon-surfaced enhanced imaging; Ultrasound (US) contrast agents; US induced blasting agents, for loading polarized gas for MRI, for treatment for Sclerosis (foam therapy) or enhancement for radiotherapy and cancer immunotherapies, as soundproofing materials, for embedding in hydrogels as tissue scaffolds (templating, or facilitating gas transport), for addition into bioreactor/fermentor to facilitate gas transport, as fuel additives. (gas in oil emulsions), as flooding fluid for enhanced oil recovery or gas-based antimicrobial agents.

The particles of the invention have, for instance, a polymeric shell that includes a release trigger and encapsulates a gas therein. The particles are stabilized in a storage solution and release the encapsulated gas upon activation of the release trigger. For example, the polymeric shell of the particles may dissolve immediately upon activation of the release trigger. For instance, upon activation of a release trigger by a pH change, for example resulting from administration of the particles into blood by infusion from a solution having a significantly different pH, the particle releases the gas. It has been demonstrated that such particles are capable of delivering gas, e.g., oxygen, at a high dose to animals in need thereof.

The particles of the invention have a number of enhanced properties over the prior art lipid based microbubbles. For instance, the particles of the invention allow large volumes of gas, e.g., oxygen, to be safely administered via intravenous injection. Further, the particles of the invention have improved shelf life and stability (e.g., a shelf life of at least 3 months longer when stored at room temperature), and thus are more readily available in a number of commercial settings. Additionally, improved mechanical stability allows the particles of the invention to be filtered and rapidly infused with no free gas release. Further, the particles of the invention are stimuli-responsive, i.e., gas encapsulated in the particles is released upon activation of the release trigger, e.g., oxygen releases from the particles when the particles are subjected to a physiological pH, e.g., by administration of the particles to blood. The particles of the invention also have a deformable and biodegradable shell, which can dissolve after gas release. Such deformability and degradability of the shell is highly desirable for intravenous gas delivery as it minimizes the risk of a large number of injected particles causing potential blockage in blood vessels. In addition, particles having an improved size distribution can be prepared according to the invention.

The invention in some aspects is a gas-filled stable particle comprising a stimuli-responsive shell encapsulating one or more gases, wherein the stimuli-responsive shell includes at least one release trigger. In some embodiments, the shell is free of one or more lipids, and the gas is not a perfluorocarbon.

A gas-filled stable particle comprising a stimuli-responsive shell encapsulating one or more gases, wherein the stimuli-responsive shell includes at least one release trigger, and wherein the gas is pressurized to greater than 1 atmosphere, and wherein the gas is oxygen, carbon dioxide, carbon monoxide, nitrogen, nitric oxide, nitrous oxide, an inhalational anesthetic, hydrogen sulfide, argon, helium, or xenon, or a mixture thereof is provided in other aspects of the invention. In some embodiments, the shell is free of one or more lipids, and the gas is not a perfluorocarbon.

In other aspects of the invention, a gas-filled stable particle comprising a stimuli-responsive shell encapsulating one or more gases, wherein the stimuli-responsive shell includes at least one release trigger, and wherein the gas is pressurized to greater than 1 atmosphere and wherein the particle has an average particle size of from 100 nm to 50 μm is provided. In some embodiments, the shell is free of one or more lipids, and the gas is not a perfluorocarbon.

In any of the aspects described herein, the release trigger, when activated, causes release of gas encapsulated in the particles described herein. The release trigger may be activated by a change in at least one condition parameter of the surroundings to which the particles are exposed, e.g., the presence or absence of a stimulus or a change in the level of a condition parameter, e.g., but not limited to pH, temperature, and pressure. Examples of the release trigger include, but are not limited to a pH-responsive trigger, a salt-responsive trigger, a pressure-responsive trigger, a temperature-responsive trigger, a light-responsive trigger, an ultrasound-responsive trigger, a magnetic field-responsive trigger, a release trigger that is responsive to partial pressure of gas in a fluid, and a combination of two or more thereof. In some embodiments, the release trigger is stable in water.

In some embodiments of various aspects described herein, the stable particles are formed using nanoprecipitation. For example, the stable particles are formed using interfacial nanoprecipitation, e.g., nanoprecipitation of one or more amphiphilic polymers at an air/liquid interface. In some embodiments, the interfacial precipitation may be oil-templated interfacial nanoprecipitation, e.g., perfluorocarbon-templated interfacial nanoprecipitation. In some embodiments, the amphiphilic polymer(s) comprise(s) a release trigger. In some embodiments, the release trigger is a chemical functional moiety that imparts responsiveness to a stimulus such that the stable particle dissolves when it is exposed to a condition that provides the stimulus.

In some embodiments, the amphiphilic polymers that are amenable to form the stable particles, e.g., using nanoprecipitation, can comprise one or more polymers comprising hydrophobic functional groups and hydrophilic functional groups. In some embodiments, the number of hydrophobic functional groups and hydrophilic functional groups present in the amphiphilic polymers are not the same. For example, in some embodiments, the number of hydrophobic functional groups present in the amphiphilic polymers may be higher than the number of hydrophilic functional groups present in the amphiphilic polymers. In some embodiments, the number of hydrophobic functional groups present in the amphiphilic polymers may be lower than the number of hydrophilic functional groups present in the amphiphilic polymers.

In some embodiments, the amphiphilic polymers can be produced by modifying hydrophilic polymers or hydrophobic polymers. By way of example only, dextran has 3 hydroxyl groups per polymer repeat. These hydroxyl groups are hydrophilic but also serve as reaction points for further modification. To render dextran amphiliphic, the hydroxyl groups of dextan can be modified with hydrophobic groups. In some embodiments, to render them responsive, they can be modified with various other chemical functional groups.

In some embodiments, for fabrication of stable particles using a hydrophilic polymer (e.g., dextran) with 3 or more hydrophilic groups per polymer repeat, some of the hydrophilic functional groups (e.g., hydroxyl groups) can be modified with a hydrophobic functional group (e.g., acetyl group). In some embodiments, the degree of substitution of the hydrophilic groups (e.g., hydroxyl groups) in a hydrophilic polymer with 3 hydrophilic groups per polymer repeat is in the range of about 1-2.5. In other words, 1 to 2.5 of the hydrophilic groups (e.g., hydroxyl groups) can be modified with a hydrophobic group (e.g., an acetyl group), such that the remaining hydrophilic groups would be in the range of 0.5-2. In some embodiments, at least one of the hydrophilic functional groups (e.g., hydroxyl groups) of a hydrophilic polymer (e.g., dextran) can be modified with a responsive trigger (e.g., a pH responsive trigger such as succinyl moiety). In these embodiments, the number of the hydrophobic functional group can remain the same. In some embodiments where dextran is used for fabrication of stable particles, the degree of substitutions of the hydroxyl group in dextran is between 0 to 2 for the succinic acid group. In other words, 0 to 2 of the hydroxyl groups in dextran can be modified with the succinic acid group.

In some embodiments of any aspects described herein, the stable particles comprises a stimuli-responsive shell surrounding a gas core, wherein the stimuli-responsive shell includes a release trigger. The gas core comprises one or more gases that suit the need of a selected application. In some embodiments, the gas core does not include a gas useful as a flame retardant. For example, in some embodiments, the gas core can comprise a biological gas which has utility in a therapeutic or diagnostic method. The biological gas may be oxygen. In some embodiments, the biological gas is oxygen, carbon dioxide, carbon monoxide, nitrogen, nitric oxide, nitrous oxide, an inhalational anesthetic, hydrogen sulfide, argon, helium, or xenon, or a mixture thereof in some embodiments. In alternative embodiments, the gas core can comprise hydrogen gas, ozone, and/or other gases that are appropriate for other applications such as gas-based antimicrobial agents.

In preferred embodiments of one or more aspects described herein, the stimuli-responsive shell comprises a biocompatible polymer or monomer. The polymer may be selected from the group consisting of dextran, poly(lactic-co-glycolic acid (PLGA), polyglutamic acid (PGA), hyaluronic acid, poly(citrate), poly(glycerol sebacate), chitosan, elastin, poly(carbonate), poly(hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof. In one embodiment, the stimuli-responsive shell comprises dextran or a derivative thereof as the biocompatible polymer.

In some embodiments, the biocompatible polymer or monomer of the stimuli-responsive shell may be modified to include a release trigger. By way of example only, dextran may be functionalized with at least one or more chemical moieties such that the chemical moiety or moieties transform in response to a stimulus or a change in at least one condition parameter of the surroundings to which the particles are exposed. In one embodiment, dextran may be functionalized with acetyl group(s) and succinyl group(s), wherein the succinyl group(s) correspond to the pH-responsive trigger. The —COOH moiety of the succinyl group(s) of the modified dextran forms hydrogen bonding with water molecules when the polymer is present in water, but a pH change (e.g., an increase in pH) can result in deprotonation of the —COOH moiety of the succinyl group(s) and thus a change in physical properties (e.g., increased solubility) of the polymer.

The particle may be a microparticle or a nanoparticle. In some embodiments, the particle has an average particle size of from 100 nm to 50 µm. In other embodiments the particle has an average particle size of from 0.5 µm-2 µm, 0.5 µm-3 µm, 0.5 µm-10 µm; 0.2 µm-2 µm, 0.2 µm-3 µm, 0.2 µm-10 µm, or 0.1 µm-less than 0.5 µm.

The gas in the particle is pressurized in some embodiments. In other embodiments, the particle comprises at least 20%, 30%, 40%, 50%, 60%, 70%, 80% 90% or 95% gas by volume.

In some embodiments, the stable particle does not comprise a non-gas-based hydrophobic or hydrophilic drug.

In some embodiments, the shelf-life of the particle is greater than 3 months, or greater than 6 months or greater than 1 year. For example, the stable particles retain at least about 90% or higher (including, e.g., at least about 95%, at least about 98%, at least about 99%, or up to 100%) of the gas fraction inside the particles and/or particle size after storage for a period of time, e.g., a period of greater than 3 months, greater than 6 months, or greater than 1 year.

According to other aspects the invention is a pharmaceutical composition comprising a gas-filled stable particle described herein and a pharmaceutically acceptable excipient.

A suspension of a gas-filled particle described herein in aqueous solution for storage is provided in other aspects of the invention.

In other aspects a powder of a gas-filled particle described herein formulated in a powder form for storage is provided.

In any of the above aspects, in certain embodiments, the one or more gases is not a fluorinated gas, perfluorocarbon based liquid, or a hemoglobin (e.g., a natural or synthetic hemoglobin). In certain embodiments, the one or more gases is not air (e.g., natural air). In certain embodiments, the one or more gases is not covalently bound to the particle. In certain embodiments, the one or more gases is not dissolved in the shell of the stable particle.

In certain embodiments, the particle and/or pharmaceutical composition comprising the particle further includes a therapeutic agent. In certain embodiments, the particle and/or pharmaceutical composition comprising the particle further includes a therapeutic agent co-formulated with the gas to be delivered.

In another aspect, provided is a method of delivering a gas to a subject in need thereof, the method comprising administering to the subject a pharmaceutical composition comprising a particle as described herein and a pharmaceutically acceptable excipient. In certain embodiments, the pharmaceutical composition is administered to the subject by intravenous, intraosseous, intraperitoneal, intraarterial, subcutaneous, and/or intramuscular injection or infusion. In certain embodiments, the pharmaceutical composition is administered to the subject by inhalation or nebulization. In certain embodiments, the pharmaceutical composition is administered topically to the skin, e.g., to a wound or lesion. In certain embodiments, the gas is oxygen. In certain embodiments, oxygen is delivered at an infusion rate of 10 to 400 ml/minute to the subject. In certain embodiments, the subject is or is suspected of experiencing local or systemic hypoxia. In certain embodiments, the subject has or is suspected of having a disease or disorder selected from the group consisting of congenital physical or physiologic disease, transient ischemic attack, stroke, acute trauma, cardiac arrest, exposure to a toxic agent (e.g., such as carbon monoxide), heart disease, hemorrhagic shock, pulmonary disease, acute respiratory distress syndrome, infection (e.g. sepsis), acute decompression sickness, and multi-organ dysfunction syndrome. In some embodiments, the pharmaceutical composition may be delivered to a solid tumor that is hypoxic in one or more regions of the tumor. In some embodiments, the pharmaceutical composition may be administered in combination with radiotherapy, radiation therapy, cancer immunotherapy, or any combinations thereof.

The stable particles and compositions comprising the same described herein can be used in various medical or non-medical applications, e.g., but not limited to therapeutic applications in which the stable particles are used to deliver a gas to a subject in need thereof; as a contrast agent in diagnostic imaging (e.g., ultrasound imaging, Plasmon-surface enhanced imaging, or MRI imaging); as additives in cosmetic and/or personal care compositions, e.g., for viscosity enhancement and color modulation; as additives in food products and/or beverages, e.g., to improve texture and/or stability; as antimicrobial or pesticides (e.g., for plants or crops, or for water treatment, or for treatment of skin diseases); as fuel additives to improve fuel efficiency; etc. Additional applications include, but are not limited to use of the stable particles described herein to form acoustic barriers; addition of the stable particles described herein in a flooding fluid for enhanced oil delivery; and addition of the stable particles described herein in a hydrogel tissue scaffold as porogens or to facilitate gas transport.

Methods of preparing the stable particles according to one or more embodiments described herein are also provided. For example, in one embodiment, the method comprises homogenizing, in the presence of air, a solution comprising one or more materials that form a stimuli-responsive shell, thereby forming hollow particles comprising a stimuli-responsive shell. The hollow particles are subsequently filled with one or more gases, e.g., by back diffusion of one or more gases into the hollow particles, to form the gas-filled stable particles described herein.

Other methods for making the stable particles are also contemplated. For example, particles may be made around a small core component to create a hollow structure, wherein the core component is removed to form a hollow dried particle.

For example, in one embodiment, provided is a method of preparing a particle encapsulating a core component, the method comprising mixing one or more materials with a core component to form a pre-suspension comprising particles encapsulating the core component in a stimuli-responsive shell.

In another embodiment, provided is a method of preparing a particle encapsulating a core component, the method comprising: mixing one or more materials with a core component to form a pre-suspension comprising particles encapsulating the core component in a stimuli-responsive shell, wherein at least one material comprises a covalent or non-covalent crosslinkable group; and subjecting the particle to polymerization or crosslinking conditions in order to provide a covalent or non-covalent crosslinked stimuli-responsive shell. In some embodiments the core component is removed. In other embodiments the core component is a volatile medium.

In another aspect, provided is a method of preparing a particle encapsulating a core component, the method comprising: mixing one or more materials with a core component to form a pre-suspension comprising particles encapsulating the core component around a stimuli-responsive shell, wherein at least one material comprises a covalent or non-covalent crosslinkable group; and contacting the particle with a material which comprises a covalent or non-covalent crosslinkable group, wherein the material encapsulates the membrane as a covalent or non-covalent crosslinked sheath membrane upon subjecting the mixture to polymerization or crosslinking conditions. In certain embodiments, the core component is removed from the particle to provide a hollow dried particle.

In another aspect a method for preparing a gas filled particle is provided. The method involves spray drying a polymer with a core component to produce a hollow dry particle and contacting the hollow dry particle with a biological gas. In some embodiments the biological gas is oxygen. In other embodiments the gas is pressurized. In yet other embodiments the spray drying of the polymer is achieved using a 3-fluid nozzle.

In other aspects, methods for preparing a stable particle (e.g., including a release trigger) are provided. In some embodiments, the method involves adjusting hydrophobic/hydrophilic balance of a polymer to produce a functionalized polymer (e.g., comprising a release trigger), performing an interfacial nanoprecipitation of the functionalized polymer (e.g., nanoprecipitation of the functionalized polymer at the air/liquid interface) by dissolving the functionalized polymer in an organic solvent and water to create a mixture, subjecting the mixture to homogenization to generate microbubble templates, adding water to further induce nanoprecipitation at the polymeric interface of the microbubble templates, thereby producing a cream of stable particles (e.g., including the release trigger). The stable particles can then be collected and loaded with a gas of interest to generate stable gas-filled particles (e.g., particles that are stimulus-responsive). In some embodiments of the methods described herein, the homogenization step is performed in the presence of air.

In some embodiments, the method for preparing a stable particle involves adjusting hydrophobic/hydrophilic balance of a polymer to produce a functionalized polymer; performing an oil-template based phase separation in the presence of the functionalized polymer, wherein the functionalized polymer acts as a self-emulsifier and oil forms particle templates; performing an interfacial nanoprecipitation (e.g., nanoprecipitation at an air/liquid interface) to generate an oil-filled particle; drying or freeze-drying the oil-filled particle, thereby producing a stable gas-filled particle. In some embodiments, the oil comprises perfluorocarbon. In some embodiments, the interfacial nanoprecipitation is oil-templated interfacial nanoprecipitation, e.g., perfluorocarbon-templated interfacial nanoprecipitation. In some embodiments, the method can further comprise subjecting the mixture to homogenization to facilitate generation of microbubble templates. In some embodiments, the method can further comprise adding water to further induce nanoprecipitation at the polymeric interface of the microbubble templates, thereby producing stable particles. In some embodiments of the methods described herein, the homogenization step is performed in the presence of air.

In some aspects, provided herein is a composition comprising a stable particle having a shell comprised of a nanoaggregate of primary particles, each primary particle having an average diameter of 50 nm or less, surrounding a gas core, wherein the shell has a thickness of 10-280 nm. In some embodiments, the shell includes a release trigger. Examples of a release trigger include, but are not limited to a pH-responsive trigger and any of the release triggers described herein.

In some embodiments, the stable particle is formed by nanoprecipitation of an amphiphilic polymer comprising a release trigger at an air/liquid interface to form the shell. For example, the amphiphilic polymer can comprise acetylated polymer such as acetylated dextran (Dex-Ac).

In another embodiment involving any of the stable particles described herein, the shell can comprise succinylated and acetylated polymer in an acetyl:succinyl ratio of 2-3:0.3-1.0, 2.2-2.3:0.3-1.0, 2-3:0.5-0.6, or 2.25-2.30:0.5-0.6.

In some embodiments, the shell can comprise succinylated and acetylated dextran (Dex-Ac-Suc), wherein the succinyl moiety of the Dex-Ac-Suc is the pH-responsive trigger.

In some embodiments, the gas core comprises, essentially consists of, or consists of oxygen.

In some embodiments involving any of the stable particles described herein, the stable particle may have a mean diameter of from 1 to 5 μm. In some embodiments, the stable particle may has a mean diameter of from 3 to 4 μm. In some embodiments, the stable particle may have a mean diameter of from 50 nm to 900 nm, or from 100 nm to 800 nm, or from 200 nm to 600 nm, or from 200 nm to 500 nm.

In some embodiments involving any of the stable particles described herein, the stable particle may have a shell thickness of 10-200 nm, 10-100 nm, 10-50 nm, 15-200 nm, 15-100 nm, 15-50 nm, 20-200 nm, 20-100 nm, 20-50 nm, 20-40 nm, 30-40 nm, or 20-30 nm. In some embodiments, the stable particle may have a shell thickness of 1-20 nm, 1-10 nm, 1-5 nm, 5-20 nm, 5-10 nm, 2-20 nm, 2-10 nm, 2-5 nm, 2-4 nm, 3-4 nm, or 2-3 nm.

In some embodiments involving any of the stable particles described herein, the stable particle can comprise 30-100%, 40-100%, 50-100%, 60-100%, 65-100%, 30-90%, 40-90%, 50-90%, 60-90%, 65-90%, 30-80%, 40-80%, 50-80%, 60-80%, 65-80%, 30-70%, 40-70%, 50-70%, 60-70%, 65-70%, 30-65%, 40-65%, 50-65%, 60-65%, or 63-65% gas carrying capacity.

In some embodiments involving any of the stable particles described herein, the stable particle can comprise 25-40, 25-30, 28-35, 29-33, 30-33 or 31-32 mL $O_2$/gram of polymer.

In some embodiments involving any of the compositions described herein, the composition may have minimal to no change in size distribution of stable particles for greater than 3 months, wherein the minimal change is 5% or less, 4% or less, 3% or less, 2% or less, 1% or less, 0.8% or less, 0.5% or less, 03% or less, or 0.1% or less. In some embodiments, the composition may have no change in size distribution of stable particles for greater than 3 months or longer. In some embodiments, the composition may have minimal to no change in size distribution of stable particles for greater than 6 months or longer. In some embodiments, the composition may have minimal to no change in size distribution of stable particles for greater than 1, 2, 5, or 10 years or longer.

In some embodiments involving any of the compositions described herein, the composition may have minimal to no change in total number of stable particles for greater than 3 months or longer, wherein the minimal change is 5% or less, 4% or less, 3% or less, 2% or less, 1% or less, 0.8% or less, 0.5% or less, 0.3% or less, or 0.1% or less. In some embodiments, the composition may have minimal to no change in total number of stable particles for greater than 6 months or longer. In other embodiments the composition has minimal to no change in total number of stable particles for greater than 1, 2, 5, or 10 years or longer.

In some embodiments involving any of the stable particles described herein, the stable particles have a high shear plateau comparable to lipidic oxygen microbubbles. For example, in some embodiments, the high shear plateau is $\gamma > 0.1 \text{ s}^{-1}$.

Some other aspects provided herein relate to stable therapeutic compositions. In one aspect, provided herein is a stable therapeutic composition comprising a stable particle having a shell comprised of polymeric primary particles, surrounding a gas core, wherein the stable particle has a gas permeability comparable to a lipidic oxygen microbubble and wherein the composition has no microvascular obstruction when infused at a 50% to 80% volume.

In another aspect, provided herein is a stable therapeutic composition comprising a stable particle having a shell comprised of primary particles, surrounding a gas core, wherein the composition has minimal to no change in total number of or change in size distribution of stable particles for greater than 3 months or longer, wherein the minimal change is 5% or less, 4% or less, 3% or less, 2% or less, 1% or less, 0.8% or less, 0.5% or less, 0.3% or less, or 0.1% or less.

In a further aspect, provided herein is a medical delivery device comprising a container and any of the compositions or stable particles described herein and instructions for administering the composition to a subject in need of administration of a gas. In some embodiments, the container is an infusion bag.

The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWINGS

The figures are illustrative only and are not required for enablement of the invention disclosed herein.

DETAILED DESCRIPTION OF CERTAIN EMBODIMENTS OF THE INVENTION

Figure 1:
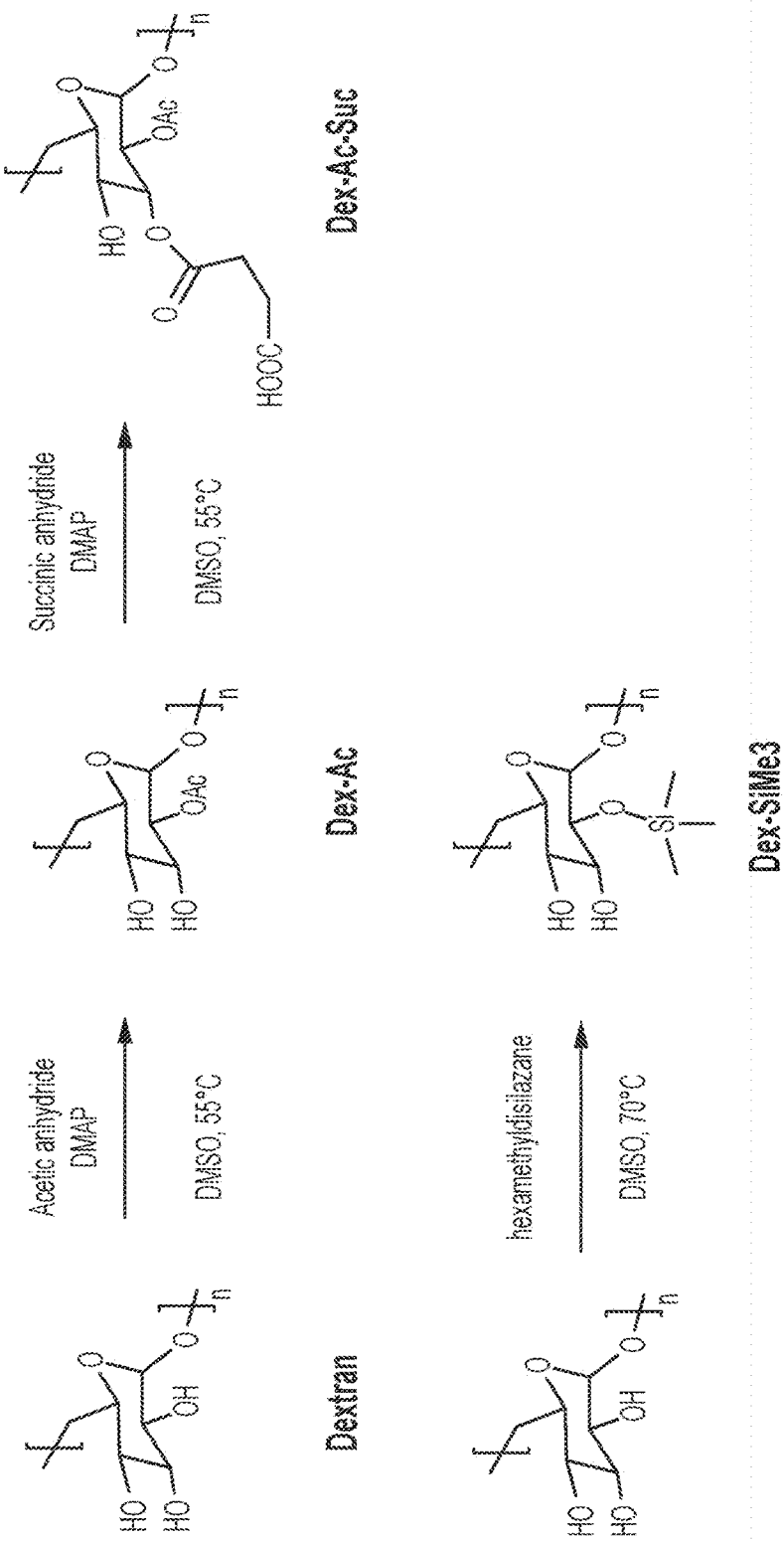
FIG. 1 shows an exemplary synthesis scheme for dextran derivatives for use in fabrication of the particles according to some embodiments described herein.

The following examples are intended to illustrate certain aspects of certain embodiments of the present invention, but do not exemplify the full scope of the invention.

Previous work has established the possibility of encapsulating a gas, such as oxygen, in a lipid membrane in the form of a microbubble for therapeutic delivery of the gas to a subject. The fluidity of the lipid membrane of the microbubble resulted in rapid delivery of the gases when administered to a subject. For example, previous work has established that administering to asphyxial subjects oxygen-filled microparticles via intravenous injection successfully restores oxygen supply in the subject, preserves spontaneous circulation during asphyxia, and reduces occurrence of cardiac arrest. See, e.g., US Publication No. 2009/0191244 and PCT Application Publication No. WO 2012/065060, incorporated herein by reference. However, current microbubble formulations may break upon experiencing high shear forces (e.g. by rapid injection through an intravenous or intraosseous catheter) causing free gas release and bubble coalescence which lead to fatal pulmonary embolism. Furthermore, the instability of lipid-based microparticles when stored prior to use may be attributed to three main mechanisms: lipid oxidation, lipid hydrolysis, and/or aggregation. The lipid-based microbubbles also may be less stable at various temperatures. Lipid oxidation and hydrolysis can occur via a variety of mechanisms and ultimately lead to the degradation of the lipid backbone, which destabilizes the lipid monolayer and promotes dissolution of the encapsulated oxygen gas, causing these molecules to have a short shelf life.

It was discovered, quite surprisingly, according to one aspect of the invention, that stabilized particles encapsulating one or more gases in a stimuli-responsive shell (e.g., a stimuli-responsive polymeric shell) are useful in various medical or non-medical applications, for example, for delivering gas to a subject for therapeutic and diagnostic purposes. In particular, the stimuli-response shell includes a release trigger such that the shell of the gas-filled particles remains stable under a first condition in which the release trigger is stable, and begins to break up or dissolve under a second condition that activates the release trigger, e.g., triggered by a physiological pH. The shell of the particles may further deform and disintegrate, thereby reducing the risk of a large number of injected particles blocking blood vessels when they accumulate. The contents of the particle may be released from the particle before, at the same time as or after the release trigger is activated. For instance, the contents of the particle may remain completely within the particle until after the release trigger is activated and then be released when the particle breaks apart. Alternatively, the contents may be release before the triggering event. For example, when a particle encapsulates oxygen and there is a change in oxygen tension, such tension allows oxygen (inside the particles) to rapidly exchange with dissolved gas (e.g., dissolved nitrogen) in the blood. In other words, dissolved gas (e.g., dissolved nitrogen) would diffuse into the particles while gaseous oxygen would dissolve into water and diffuse out of the particles. Upon activation of the release trigger to dissolve the shell, the remaining gas inside the particles (if there is any left) is released. In other embodiments where oxygen-filled particles are added to an oxygen-rich environment, encapsulated oxygen is released upon activation of the release trigger in the shell of the particles.

Cardiac arrest (i.e. complete cessation of blood flow) is the most lethal medical condition and resuscitation requires immediate restoration of oxygen delivery to the myocardium. Intravenous injection (i.v.) of oxygen carrying microcarriers is an emerging strategy for rapid myocardial oxygen delivery; however, existing microcarriers are unstable and cause vascular obstructions making them unsuitable for clinical use. Ultra-stable and triggered self-eliminating microbubbles (stable particles) as gas carriers have been developed using a method in some embodiments that manipulates a phenomenon of nanoprecipitation of amphiphilic biopolymers at air/liquid interface. These stable particles are extremely stable for long periods of time, and rapidly dissolve when infused into blood. In the tests described herein we have observed no change in size distribution or total number of particles after several months, which is quite unexpected. Repeated i.v. infusions were safe and hemodynamically well tolerated in animal models. When added to a standard resuscitation algorithm in an asphyxial cardiac arrest model, the stable particles increased survival from 0% to 100%.

The invention in some aspects is a gas-filled stable particle comprising a stimuli-responsive shell encapsulating one or more gases, wherein the stimuli-responsive shell includes a release trigger. In some embodiments, the shell is free of one or more lipids, and the gas is not a perfluorocarbon.

The term "particles" as used herein refers to a shell capable of housing a gas within the hollow core. In some embodiments, the particles may be nanoparticles or microparticles.

A "stabilized particle" and "stable particle" as used interchangeably herein to refer to a particle comprising a stimuli-responsive shell that remains stable when the release trigger is not activated, and deforms and optionally dissolves or disintegrates when the release trigger is activated. Thus, a stable particle is a particle that is at least stable under a condition in which the release trigger is not activated. By way of example only, a stable particle remains stable over a period of time, e.g., at least three months or longer, when it is maintained at room temperature in a first solution having a first pH, and deforms or optionally dissolves or disintegrates when it is exposed to a second solution having a second pH, wherein the first pH and the second pH are different. In some embodiments, the second pH corresponds to a physiological pH.

The stabilized particle may be composed solely of a stimuli-responsive shell and a gas core. Alternatively the stabilized particle may include a stimuli-responsive shell surrounding an optional sheath wherein the sheath is positioned between the gas core and the stimuli-responsive shell and/or other components. The sheath may be composed of a lipid membrane. In some embodiments the sheath is a lipid membrane such as a microbubble lipid membrane described in US Publication No. 2009/0191244 or PCT Publication No. WO2012/065060. The stimuli-responsive shell and sheath may be each independently covalently or non-covalently crosslinked and/or stabilized, for example, by a stabilizing agent or by the interactions between the one or more components of the membrane or based on the chemical properties of the one or more components of the membrane (for instance the hydrophobicity of a polymer such as PLGA).

A "stabilized particle" as used herein does not encompass a bubble or microbubble having a non-crosslinked lipid membrane, unless the bubble or microbubble includes a further stimuli-responsive shell composed of a material other than non-crosslinked lipids. For instance, a stabilized particle may include an inner non-crosslinked lipid membrane and an outer stimuli-responsive shell comprising one or more polymers.

The stability of the particles described herein may be characterized by measuring the size or volume of the particles over a period of time. For example, in some embodiments, particles are "stable" when the decrease in particle size or volume is no more than 10% or less (including, e.g., no more than 9%, no more than 8%, no more than 7%, no more than 6%, no more than 5%, no more than 4%, no more than 3%, no more than 2%, no more than 1% or less) over a period of at least three months or longer (including, e.g., at least four months, at least five months, at least six months, at least nine months, at least one year, or longer). In some embodiments, particles are "stable" when the increase in particle size or volume (e.g., due to Ostwald ripening or coalescence) is no more than 10% or less (including, e.g., no more than 9%, no more than 8%, no more than 7%, no more than 6%, no more than 5%, no more than 4%, no more than 3%, no more than 2%, no more than 1% or less) over a period of at least three months or longer (including, e.g., at least four months, at least five months, at least six months, at least nine months, at least one year, or longer).

In some embodiments, the stability of the particles described herein may be characterized by measuring the height of foam in which the particles are suspended over a period of time. For example, in some embodiments, particles are "stable" when the decrease in foam height is no more than 10% or less (including, e.g., no more than 9%, no more than 8%, no more than 7%, no more than 6%, no more than 5%, no more than 4%, no more than 3%, no more than 2%, no more than 1% or less) over a period of at least three months or longer (including, e.g., at least four months, at least five months, at least six months, at least nine months, at least one year, or longer). The height of the foam may be visually measured using a volume marked syringe in which foam is stored.

A "stimuli-responsive shell" as used herein is a shell including a release trigger and surrounding a hollow core capable of being filled with a gas. The shell remains stable when the release trigger is not activated (or suppressed), and deforms and optionally dissolves or disintegrates when the release trigger is activated, thereby releasing gas encapsulated therein. Upon activation of the release trigger, the dissolution and/or disintegration of the shell may occur within seconds, e.g., within 1 second, 2 seconds, 3 seconds, 4 seconds, 5 seconds, or more. The stimuli-responsive shell may comprise a polymer, a monomer, or a monomer-polymer mixture. In some embodiments, the stimuli-responsive shell is lipid-free.

A "release trigger" as used herein refers to an entity, e.g., a chemical moiety, a molecule, a compound, a polymer, a monomer, or a material, that exhibits a response to a trigger or stimulus, or a change in the level of an environmental condition parameter (e.g., but not limited to pH, temperature, and pressure) and the response causes the gas-filled particles described herein to begin to break up or dissolve. In some embodiments, the encapsulated gas may release from the particles, e.g., by diffusion, due to the presence of a concentration gradient. In these embodiments, a portion of the encapsulated gas may release from the particles to equilibrate with the surroundings before the shell of the particles breaks up or dissolves. Upon activation of the release trigger to dissolve the shell, the remaining gas inside the particles is released. In other embodiments, e.g., in the absence of a concentration gradient, the encapsulated gas may be released from the particles upon activation of the release trigger that causes the gas-filled particles to break up or dissolve. The release trigger may be activated, for example, by subjecting the particles described herein to one or more stimuli that directly or indirectly trigger release of gas encapsulated inside the particles. Examples of a stimulus that may act as a trigger or stimulus include, but are not limited to pH, salt type and/or concentration, pressure, temperature, light, ultrasound, magnetic field, a chemical or biological molecule, partial pressure of a gas in a fluid, and a combination of two or more thereof. In some embodiments, the release trigger is stable in water.

Figure 2:
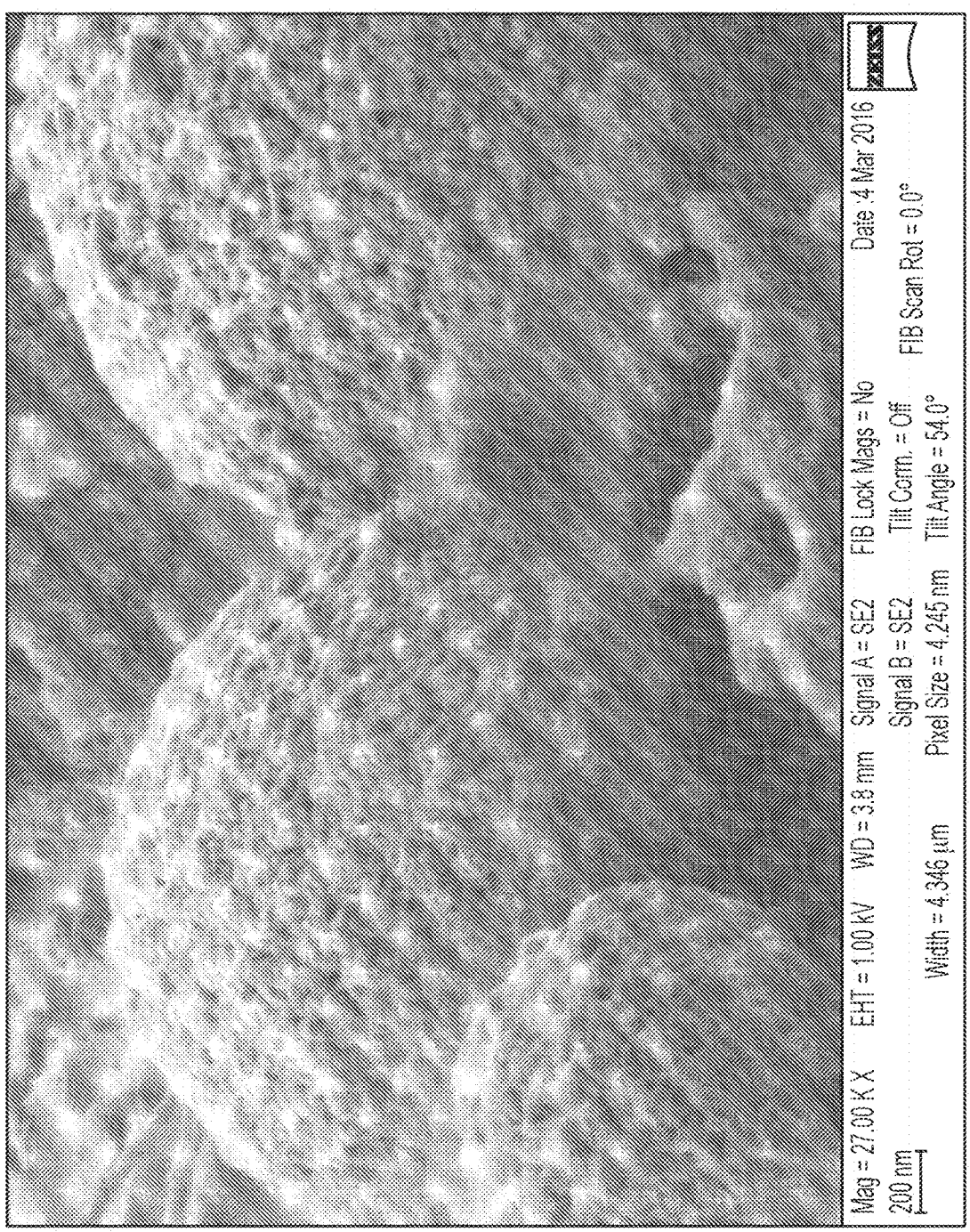
FIG. 2 shows a cryo-image of microparticles (MPs) formed using Dex-Ac-Suc polymers. The degrees of substitution are 2.2 and 0.1, respectively.
Figure 3:
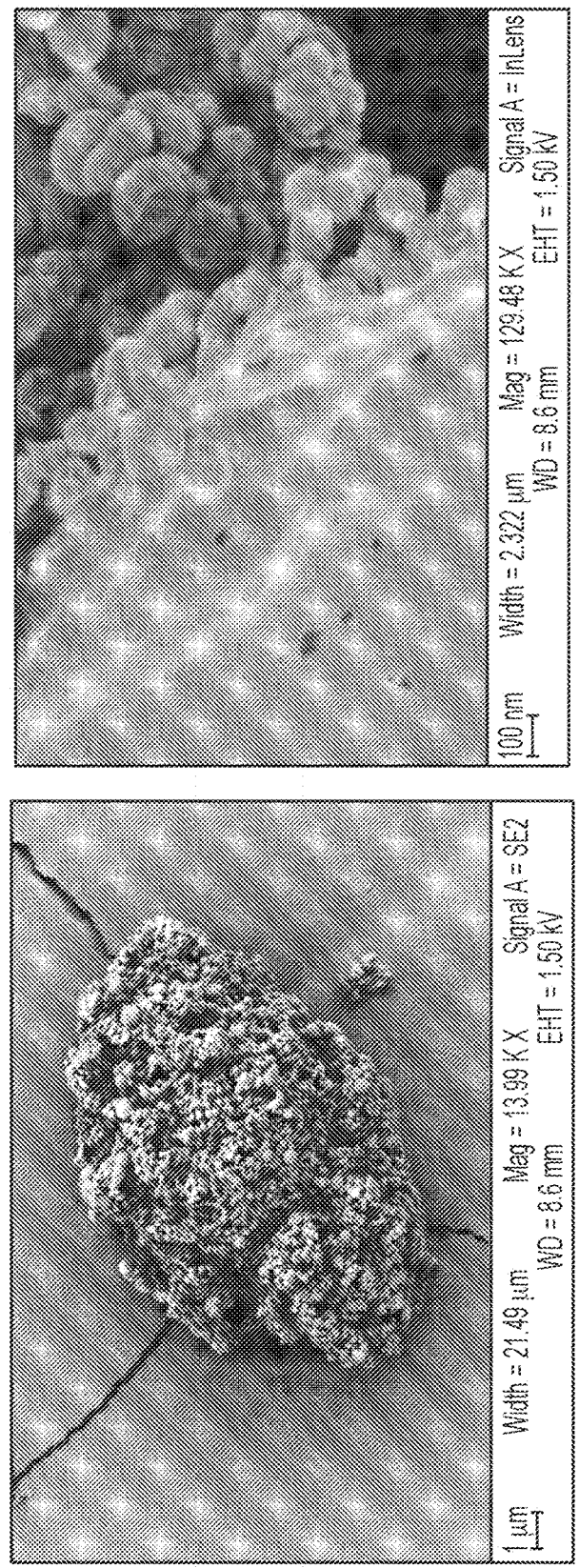
FIG. 3 shows SEM images of microbubbles formed using Dex-SiMe3 after freeze-drying. The left images shows an intact MP. The right image depicts the cross-section of a MP, showing a smooth interior and nanoparticle aggregates on the exterior.

In some embodiments, the stable particle is a nanoprecipitated particle, for example, a particle formed by nanoprecipitation. For example, the stable particle is formed using interfacial nanoprecipitation, e.g., nanoprecipitation of one or more amphiphilic polymers (e.g., one or more polymers comprising a balanced ratio of hydrophobic functional groups and hydrophilic functional groups) at an air/liquid interface. In some embodiments, the air/liquid interface can be air/water interface. In some embodiments, the air/liquid interface can be air/oil interface. In some embodiments, the particle comprises a stimuli-responsive shell surrounding a gas core, wherein the shell comprises nanoparticle aggregates and a release trigger. FIGS. 2-3 show examples of the stable particles according to some embodiments described herein, wherein the stable particles comprise a shell formed of nanoparticle aggregates and comprising a release trigger. The nanoparticles in the aggregates may comprise any polymer, e.g., as described in the "Polymers" section below. The size of the nanoparticle in the aggregates can vary depending on the materials. For example, in some embodiments, the nanoparticles in the aggregates may have a size in the range of about 10 nm to about 100 nm. In one embodiment, the nanoparticles are dextran-based.

The term "hydrophobic functional group" as used herein refers to a group that does not have an affinity for water. Hydrophobic groups have the ability to catalyze chemical reactions and adsorb and/or immobilize target compounds or other functional groups, by excluding water, or by providing a surface for hydrophobic interactions, or by providing a reactive surface. An example of such group, without limitation, is a nonionic group, an ester group, a succinimide group or an epoxy group. Other examples of hydrophobic functional groups include hydrocarbons having 4 or more carbon atoms, free-radically polymerizable monomers which include vinyl aromatic monomers, e.g., styrene, .alpha.-methyl styrene, t-butyl styrene and vinyl toluene; vinyl and vinylidene halides, e.g., vinyl chloride and vinylidene chloride; vinyl esters; vinyl ethers, vinyl butyrates, alkyl esters of acrylic and methacrylic acids having from 4 to 17 carbon atoms in the alkyl group, including butyl methacrylate, butyl acrylate, cyclohexyl methacrylate, 4-tert-butylcyclohexylacrylate, cyclohexyl acrylate, 2-ethylhexyl methacrylate, 2-ethylhexyl acrylate, butyl hexylmethacrylate, butyl hexylacrylate, isooctylmethacrylate, isooctylacrylate, isodecyl methacrylate, isodecyl acrylate, isobornyl methacrylate, isobornyl acrylate, lauryl methacrylate and lauryl acrylate; and mixtures thereof. In some embodiments, degree of hydrophobicity is determined based on the degree of substitution.

The term "hydrophilic functional group" as used herein refers to a group that has an affinity for water but does not undergo significant ionic dissociation upon contact with water. An example of such group, without limitation, is a hydroxyl group. Other examples of suitable hydrophilic groups include, for example, a hydroxyalkyl group (where the alkyl group is preferably a lower alkyl group), an amino group, a pyrrolidonyl group, ethanolamine, hydroxyethyl methacrylate, hydroxypropyl acrylate, vinylpyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate. Preferred hydrophilic groups include a hydroxyl group and a hydroxyalkyl group.

In some embodiments, a polymer for use in formation of stable particles, e.g., through nanoprecipitation, are surface active. In some embodiments, a polymer that is not surface active can be modified to be surface active. By way of example only, dextran is not surface active. Modifying it with, e.g., acetyl groups with a degree of substitution (DS) of 1.0 or greater renders dextran polymer surface active. A surface active polymer can bind at the air-water interface and stabilize gas bubbles.

In some embodiments, a polymer for use in formation of stable particles, e.g., through nanoprecipitation, can self-emulsify oils (e.g., perfluorocarbon) in water. By way of example only, modifying dextran with, e.g., acetyl groups and alkylamine (e.g., but not limited to butylamine) groups, can render dextran polymer as a self-emulsifier. Thus, dextran can self-emulsify oil (e.g., perfluorocarbon) in water and subsequently undergo interfacial nanoprecipitation to generate oil-filled core-shell particles. In some embodiments, the particles formed by oil-templated interfacial precipitation may have a mean diameter of 50 nm to 1000 nm, 100 nm to 900 nm, 200 nm to 800 nm, 250 nm to 600 nm, 250 nm to 500 nm, or 300 nm to 400 nm.

In some embodiments, the stable particle is a Pickering foam. A Pickering foam is that particles are arranged at the interface between two liquid phases and form a mechanical barrier against the combining of the liquid droplets. Accordingly, one aspect provided herein relates to a gas-filled Pickering foam comprising a stimuli-responsive shell surrounding a gas core, wherein the shell includes a release trigger and comprises nanoparticle aggregates. The nanoparticles in the aggregates may comprise surface functional groups, including but not limited to —COOH, —Si, and —R groups as described in the "Polymers" section below. Non-limiting examples of such nanoparticles include functionalized silica, starch nanoparticles, surface functionalized polyester nanoparticles, cellulose nanoparticles, and any combinations thereof. The size of the nanoparticles in the aggregates can vary depending on the materials. For example, in some embodiments, the nanoparticles in the aggregates may have a size in the range of about 10 nm to about 100 nm.

In some embodiments, the stable particle, e.g., the shell of the stable particle, comprises a Janus particle. Janus particles are particles whose surfaces have two or more distinct physical properties. For example, Janus particles have different surface makeups, structures or compartments on two sides. Methods for making Janus particles are known in the art, e.g., as described in Walther and Muller, "Janus Particles: Synthesis, Self-Assembly, Physical Properties, and Applications" Chem. Rev. (2013) 113(7): 5194-5261. For example, the Janus particles may comprise a shell that includes one or more amphiphilic polymers known in the art.

The gas-carrying capacity of the particles described herein can vary with particle size. In some embodiments, the gas-carrying capacity of the particles may range from 0.5-100 µl/mg of particles or 1-50 µl/mg of particles or 5-50 µl/mg of particles, or 5-25 µl/mg of particles. In some embodiments, the gas carrying capacity of the particles is 10 µl/mg of particles, wherein the average particle size is between 2-5 µm.

Polymers and Stimuli-Responsive Polymers

The stimuli-responsive shell and/or sheath membrane may be composed of one or more polymers. Depending on the types of medical or non-medical applications, a wide variety of biodegradable or non-biodegradable polymers can be used as a component (or as the sole constituent) of the particle, e.g., provided in the stimuli-responsive shell and/or the sheath membrane. A polymer is a chemical compound or mixture of compounds composed of structural units created through polymerization. Polymers include but are not limited to natural/biological and synthetic polymers. Polymers may be branched or unbranched. In some embodiments, the polymers are biocompatible and/or degradable, for example, when the stable particles are used in medical applications or in vivo applications.

In certain embodiments, the polymer is modified, e.g., by substitution or comprising a group X or Y attached to the material, to form covalent crosslinkages, and/or by substitution with a lipid tail.

In some embodiments, any polymer that partially dissolves in a single phase organic/aqueous mixture and/or forms nanoparticle aggregates at air-water interface in situ may be used to form the particles described herein. Examples of such polymers include, but are not limited to, proteins, carbohydrates, poly(hydroxy acids) (e.g., poly(lactic acid), poly(glycolic acid), and poly(lactic-co-glycolic acid) (PLGA), polyglycolides, polylactides, polylactide co-glycolide copolymers and blends, polyanhydrides, polyorthoesters, polyglutamic acid (PG), polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly (vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly (methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), polyallylamines, copolymers and blends thereof. As used herein, "derivatives" include polymers having substitutions, additions of substituents, for example, alkyl, alkenyl (e.g., vinyl, allyl), alkynyl, carbocyclyl, heterocyclyl, aryl, heteroaryl, etc. modifications by hydroxylations, oxidations (e.g., oxidation to provide —CHO or —CO$_2$H functionalization), and others routinely made by those skilled in the art.

The polymers may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (e.g., arborescent and hyperbranched polymers). The polymers can be formed from a single monomer (i.e., they can be homopolymers), or they can be formed from multiple monomers (i.e., they can be copolymers) that can be distributed, for example, randomly, in an orderly fashion (e.g., in an alternating fashion), or in blocks. In many embodiments of the present invention, biodisintegrable polymers are employed. A "biodisintegrable material" is one that, subsequent to release within the subject, undergoes dissolution, degradation, resorption and/or other disintegration processes.

Further examples of polymers for use in conjunction with the present invention, not necessarily exclusive of those listed above, and which may be repetitive, many of which are readily biodisintegrable, include, but are not limited to, polysaccharides and polysaccharide derivatives such as starch (e.g., Hetastarch), dextran, dextran derivatives, chitosan, and alaginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), poloxomers, polyoxyethylene (polyethylene glycol, PEG), PEGylated lipids, polyanhydrides, polyvinylalcohol, polyethyleneamine and polypyrridine, additional salts and copolymers thereof.

Examples of non-biodegradable polymers include cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts; ethylene vinyl acetate, poly(meth)acrylic acid, polyamides, copolymers and mixtures thereof. Non-biodegradable polymers can be used when the stable particles described herein are not used for in vivo applications, e.g., as an external oxygenator for organ transplant.

Examples of preferred biodegradable polymers include dextran-based polymers and/or polymers of hydroxy acids such as lactic acid and glycolic acid polylactide, polyglycolide, polylactide co glycolide, and copolymers with PEG, polyanhydrides, poly(ortho)esters, polyurethanes, poly(butyric acid), poly(valeric acid), and poly(lactide-co-caprolactone). In general, these materials degrade in vivo by both non-enzymatic and enzymatic hydrolysis.

Bioadhesive polymers of particular interest for use in imaging of mucosal surfaces, as in the gastrointestinal tract, include polyanhydrides, polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate).

In some embodiments, the polymer is a poloxamer. Poloxamers are nonionic triblock copolymers composed of a central hydrophobic chain of polyoxypropylene (also known as poly(propylene oxide)) flanked by two hydrophilic chains of polyoxyethylene (also known as poly(ethylene oxide)). The three digit number 188 indicates the approximate molecular mass of the polyoxypropylene core (i.e., 1800 g/mol) and the polyoxyethylene content (i.e., 80%). Poloxamers are commercially available, e.g., provided by BASF Corporation. Exemplary poloxamers include, but are not limited to, PLURONIC® F68, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85. In certain embodiments, the polymer is PLURONIC® F68 (poloxamer 188), PLURONIC® F108 (poloxamer 338), or PLURONIC® F127 (poloxamer 407), In certain embodiments, the stimuli-responsive shell comprises dextran or a derivative thereof as the biocompatible polymer.

In certain embodiments, the polymer is a polyethylene glycol (PEG) polymer, such as a PEGylated lipid. Exemplary PEGylated lipids include, but are not limited to, PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy (Polyethylene glycol)-5000]. In certain embodiments, the polymer is PEG-stearate.

While not necessary, in certain applications where it may be desirable to release encapsulated gas from the stable particles over a period of time, the shell of the stable particles may comprise a polymer film (e.g., a thin polymer film) that can be either porous or nonporous. In some embodiments, the polymer film may comprise a crosslinked polymer in which a bond, e.g., a covalent bond, links one polymer chain to another. Thus, in certain embodiments, any one of the polymers as described herein may be modified or comprise one or more X and Y groups to provide a crosslinkable polymer. In certain embodiments, the membrane or shell and/or sheath membrane is a crosslinked polymer (e.g., functionalized with one or more groups X and Y to form a crosslink A) as described herein.

In certain embodiments, the X and Y groups are acrylate groups. For example, in one particular embodiment, the polymer is a poloxamer modified with one or more acrylate groups, such as Pluronic F127 diacrylate. In certain embodiments, the polymer is polyglutamic acid (PG) or poly(lactic-co-glycolic acid) (PLGA), wherein one or more free carboxylic acids attached to the polymer backbone are optionally modified as acrylate groups.

Proteins are a type of polymer and may form the basis of the stimuli-responsive shell.

In certain embodiments, the protein is modified, e.g., by substitution or comprising a group X or Y attached to the material, to form covalent crosslinkages, and/or by substitution with a lipid tail. It is understood that "polypeptide" or "protein" are used interchangeably and refer to a string of at least three amino acids linked together by peptide bonds. Proteins may contain only natural amino acids, although non-natural amino acids (i.e., compounds that do not occur in nature but that can be incorporated into a polypeptide chain) and/or amino acid analogs as are known in the art may alternatively be employed. One or more of the amino acids in a protein may be modified, for example, by the addition of a chemical entity such as a carbohydrate group, a phosphate group, a farnesyl group, an isofarnesyl group, a fatty acid group, a linker for crosslinking, functionalization, or other modification.

Proteins include, for example, lipophilic and amphiphilic proteins, fibrous proteins (e.g., cytoskeletal proteins such as actin, keratin, collagen, gelatin, extracellular matrix proteins such as elastin), globular proteins (e.g., plasma proteins such as serum albumin, coagulation factors, acute phase proteins), hemoproteins, cell adhesion proteins, transmembrane transport proteins, immune system proteins (e.g., immunoglobulins (antibodies)), lung surfactant proteins (e.g., SP-A, SP-B, SP-C, or SP-D, synthetic lung surfactant proteins, lung surfactant protein mimetics), glycoproteins, and enzymes.

In certain embodiments, the protein is a cytoskeletal protein such as gelatin.

In certain embodiments, the protein is a globular protein such as an albumin protein. In certain embodiments, the albumin protein is human serum albumin or bovine serum albumin (BSA).

In certain embodiments, any one of the proteins as described herein is modified or comprise with one or more X and Y groups to provide a crosslinkable protein. In certain embodiments, the membrane and/or sheath membrane is a crosslinked protein (e.g., functionalized or comprising one or more groups X and Y to form a crosslink A) as described herein.

In certain embodiments, the X and Y groups are thiol groups, and upon oxidation form a disulfide bond. For example, in one particular embodiment, the protein is albumin with cysteine groups which react, under oxidative conditions to form a crosslinked albumin protein.

Carbohydrates or sugars may also be used as a component of the particle, e.g., provided in the stimuli-responsive shell and/or the sheath membrane.

The terms "sugar," "polysaccharide," and "carbohydrate" may be used interchangeably, and generally have the molecular formula $(CH_2O)n$. A carbohydrate may be a monosaccharide, a disaccharide, trisaccharide, oligosaccharide, or polysaccharide. The most basic carbohydrate is a monosaccharide in the D, L, cyclic or acyclic form, such as glucose (e.g., D-glucose, also known as dextrose), sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g. raffinose, stachyose), and polysaccharides include six or more monosaccharide units. Exemplary polysaccharides include starch, glycogen, and cellulose. In certain embodiments, the carbohydrate is modified, e.g., by substitution or comprising a group X or Y attached to the material, to form covalent crosslinkages, and/or by substitution with one or more lipid tails. Carbohydrates may further contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, isomers, or derivatives thereof. In one example, carbohydrates (e.g., sugars) can be oxidized with an agent such as sodium periodate to yield a reactive aldehyde group which can be used for conjugation reactions.

In certain embodiments, the carbohydrate is lactose or glucose (e.g., dextrose).

In certain embodiments, any one of the carbohydrates as described herein is modified or comprise with one or more X and Y groups to provide a crosslinkable sugar. In certain embodiments, the membrane and/or sheath membrane is a carbohydrate shell or membrane, e.g., a shell or membrane formed from modified carbohydrate (e.g., a carbohydrate modified with one or more lipid groups, such as sucrose stearate or crosslinked carbohydrate (e.g., functionalized or comprising one or more groups X and Y to form a crosslink A)).

In certain embodiments, the X and Y groups are acrylate groups. For example, in one particular embodiment, the carbohydrate is a sugar modified with one or more acrylate groups, such as starch modified with acrylate groups, which react to form a crosslinked carbohydrate.

Stimuli-Responsive Polymers

In some embodiments, the biocompatible polymer or monomer of the stimuli-responsive shell may be selected to provide a desirable release trigger as described herein. Stimuli-responsive polymers that undergo an abrupt change in its physical properties in response to an external stimulus are known in the art and may be used to form stimuli-responsive shell described herein. For example, in some embodiments, the biocompatible polymer of the stimuli-responsive shell may comprise a pH-responsive polymer. pH-responsive polymers comprise pendant acidic or basic group that can either accept or release a proton in response to changes in environmental pH, examples of which include, but are not limited to, poly(methacrylic acid), poly(vinylpyridine), poly(vinylimidazole), or any polymer that comprises or is modified to comprise a functional group that can either accept or release a proton in response to changes in environmental pH. FIG. 1 shows modification of a dextran-based polymer to become a pH-responsive polymer (e.g., Dex-Ac-Suc as shown in FIG. 1). In some embodiments, the release trigger is a pH trigger, e.g., comprising a pH-responsive polymer (e.g., as described herein). In these embodiments, gas release is triggered when the particles described herein are subjected to a desirable pH, e.g., any pH between pH=1 and pH=14. In some embodiments, the pH trigger corresponds to a physiological pH. In some embodiments, the pH trigger corresponds to the pH of a target tissue to which the particles are delivered.

In some embodiments, the pH trigger comprises one or more pH-responsive polymers that comprise one or more acid labile moieties, including, e.g., but not limited to acetal, ketal, schiff base, silyl, amine, vinyl ether, hydrazone, etc. In some embodiments, the pH trigger comprises one or more pH-responsive polymers that comprise one or more base labile moieties, including, e.g., but not limited to carboxylic acids.

In some embodiments, the biocompatible polymer of the stimuli-responsive shell may comprise a temperature-responsive polymer. Temperature-responsive polymers (also known as thermo-responsive polymers) undergo abrupt change in their solubility in response to a change in temperature. In some embodiments, a temperature-responsive polymer exhibits temperature-dependent and reversible sol-gel transitions near body temperature that control the rate of release of encapsulated gas along with maintaining physicochemical stability and biological activity. Examples of temperature-responsive polymers include, but are not limited to poly(N-isopropyl acrylamide) (PNIPAM), poly(N,N-diethylacrylamide), poly(N-vinylalkylamide), poly(N-vinylcaprolactam), phosphazene derivatives, pluronics, tetronics, polysaccharide derivatives, chitosan, and PLGA-PEG-PLGA triblock copolymers, any other lower critical solution temperature (LCST) or upper critical solution temperature (UCST) polymers known in the art, and any combinations thereof.

In some embodiments, the biocompatible polymer of the stimuli-responsive shell may comprise a bio-responsive polymers. Bio-responsive polymers are polymers that respond to a biological molecule. Bio-responsive polymers may be classified into antigen-responsive polymers, glucose- or sugar-sensitive polymers, and enzyme-responsive polymers. For example, in some embodiments, the stimuli-responsive shell may comprise a sugar-responsive shell. The sugar-responsive shell may comprise one or more polymers containing, e.g., one or more boronate moieties, e.g., as described in Nakahata et al. "pH- and Sugar-Responsive Gel Assemblies Based on Boronate-Catechol Interactions" *ACS Macro Lett.* (2014) 3: 337-340; and/or one or more phenylboronic acid monomer as described in the U.S. Pat. Application Publication No. US 2013/0066264, the contents of which is incorporated herein by reference. In some embodiments, the stimuli-responsive shell may comprise an enzyme-responsive shell. The enzyme-responsive shell may comprise one or more polymers containing one or more enzyme cleavage sites or enzyme-labile linkages, including, e.g., but not limited to esters (susceptible to lipases), amides or peptides (susceptible to proteases), DNA (susceptible to DNases), RNA (susceptible to RNases), and/or one or more self-immolative moieties that are attached with at least one enzymatic sensitive group, including, e.g., but not limited to poly(benzyl carbamate). Self-immolative moieties are known in the art, e.g., as described in Fan and Gillies (2015) "Self-Immolative Polymers" *Encyclopedia of Polymer Science and Technology.* 1-35.

In some embodiments, the biocompatible polymer of the stimuli-responsive shell may comprise a field-responsive polymer. Field-responsive polymers are polymers that respond to the application of electric, magnetic, sonic, or electromagnetic fields. In some embodiments, the biocompatible polymer of the stimuli-responsive shell may comprise a light-responsive polymer, e.g., a UV-responsive or a visible light-responsive polymer on the basis of the wavelength of light that triggers the phase transition of the polymer. The stable particles that comprise a light-responsive shell may be useful for photothermal, photodynamic, and/or photoacoustic therapies. A light-responsive shell may comprise one or more polymers containing one or more photo-cleavable linkages such as coumarinyl esters, methoxyphenacyl ester, and/or one or more self-immolative moieties that are attached with a light sensitive group, including, e.g., but not limited to poly(benzyl carbamate). Light-responsive or photo-responsive polymers, for example, as described in Bertrand and Gohy, "Photo-responsive polymers: synthesis and applications" *Polym. Chem.* (2017) 8: 52-73, can be used in the stimuli-responsive shells as described herein. Alternatively, a light-responsive shell may incorporate optically responsive nanoparticles such as gold. For example, a light-responsive shell may comprise gold nanoparticles. Gold nanoparticles can interact with light and have strong tunable surface plasmon resonance which are useful for noninvasive imaging as they can be detected using multiple imaging modalities, e.g., as described in Pekkanen et al., "Nanoparticle enhanced optical imaging and phototherapy of cancer," *J. Biomed Nanotechnol* (2014) 10: 1677-1712.

In some embodiments, the biocompatible polymer of the stimuli-responsive shell may comprise an electric field-responsive polymer that changes its physical properties (e.g., increased solubility) in response to a change in electric current, examples of which include but are not limited to sulfonated polystyrenes, poly(thiophene), and poly(ethyloxazoline).

In some embodiments, the biocompatible polymer of the stimuli-responsive shell may comprise an ultrasound-responsive polymer, e.g., ethylene vinylacetate. In some embodiments, the ultrasound responsive polymer may comprise one or more polymers containing one or more linkages of mechanophore, including, e.g., but not limited to benzocyclobutene, bis(adamantyl)-1,2-dioxetane, etc. See, e.g., Cravotto et al. "On the mechanochemical activation by ultrasound" *Chem. Soc. Rev.* (2013) 42: 7521-7534, for examples of moieties that are responsive to ultrasound.

In some embodiments, the biocompatible polymer of the stimuli-responsive shell may comprise a magnetic field-responsive polymer, e.g., a polymer comprising iron or iron oxide particles or powder dispersed therein, and/or magnetically active nanoparticles (including, e.g., iron oxide, gold, etc.).

In some embodiments, the biocompatible polymer of the stimuli-responsive shell may comprise a salt-responsive polymer that change its physical properties (e.g., increased solubility) in response to the presence of a salt, as compared to their physical properties in the absence of a salt (e.g., water without salt). For example, in some embodiments, a salt-responsive shell may comprise one or more polymers that undergo a conformational change as a result of chelating with ions. Such an exemplary salt-responsive polymer includes, but is not limited to alginate.

In some embodiments, the stimuli-responsive shell may comprise a pressure-responsive shell. The pressure-responsive shell may comprise a pressure-responsive polymer. Alternatively, the pressure-responsive shell may comprise weakly associated nanoparticles that undergo dissociation upon exposure to pressure or flow, e.g., as described in Korin et al. "Shear-activated nanotherapeutics for drug targeting to obstructed blood vessels" *Science* (2012) 337: 738-742.

In some embodiments the biocompatible polymer or monomer for use in the stimuli-responsive shell may be modified to provide or conjugated to a release trigger. By way of example only, dextran may be functionalized with at least one or more chemical moieties such that the chemical moiety or moieties transform in response to a desirable stimulus, e.g., but not limited to pH and a target molecule (e.g., glucose or $CO_2$). For examples, dextran may be functionalized with acetyl group(s) and succinyl group(s), wherein the succinyl group(s) correspond to the pH trigger. See, for example, Example 1 and FIG. 1 for an exemplary method to synthesize a pH-responsive dextran. The —COOH moiety of the succinyl group(s) in dextran forms hydrogen bonding with water molecules when the dextran polymer is present in water, but a pH change (e.g., an increase in pH) in the surrounding solution can result in deprotonation of the COOH moiety of the succinyl group(s), thus changing the physical properties (e.g., increased solubility and/or decreased mechanical property) of the dextran polymer. The dissolution rate of the modified dextran can further be tuned by the degree of substitution (DS) of the succinyl group. As an illustration, Example 2 shows that particles formed from dextran with high DS of succinyl groups (e.g., DS=0.3) instantly dissolve at a physiological pH with the shell disintegrating quickly, while ones formed from dextran with a lower DS of succinyl groups (e.g., DS=0.1) are filled with fluid while the shells become deformable rather than disintegrating quickly.

Similarly, other structural variation of dextran can be prepared as follows to provide release trigger.

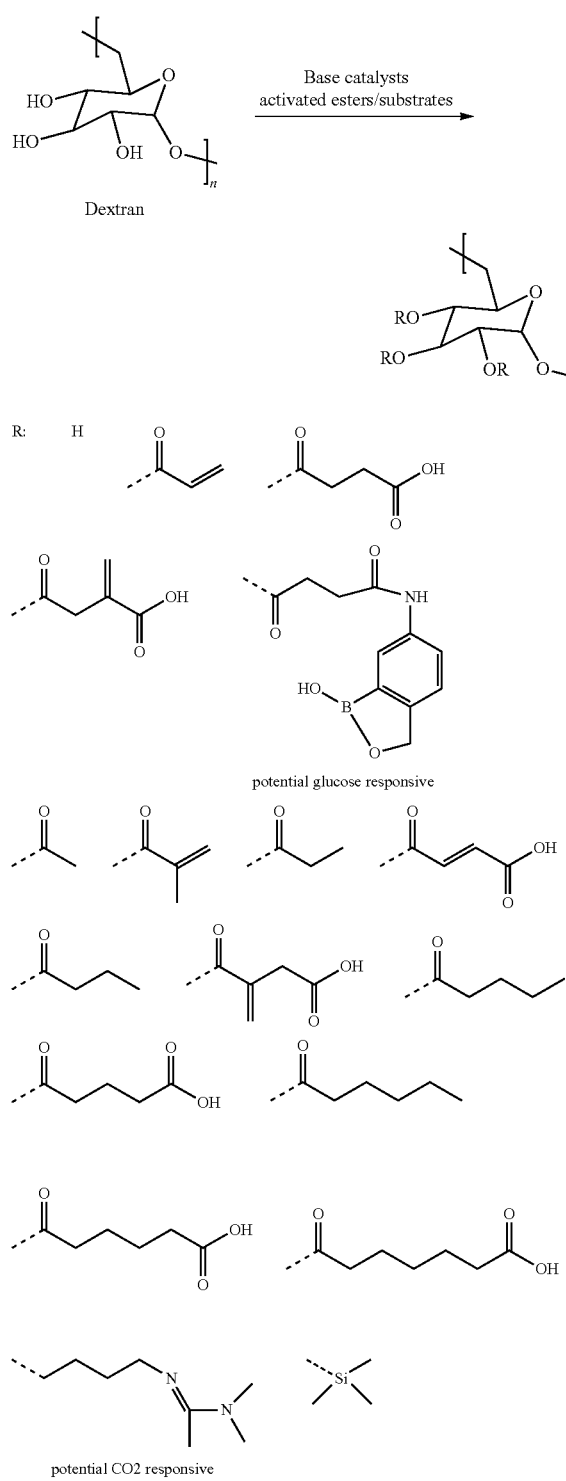

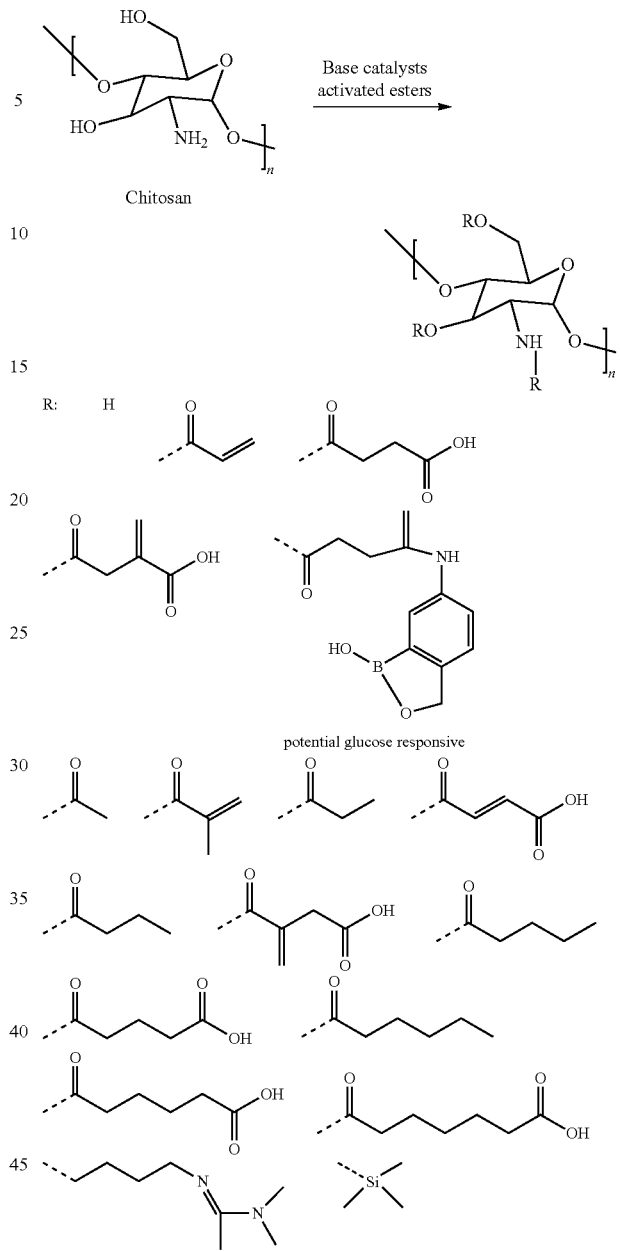

The R substitution can be any combination. Groups with —COOH or —Si are pH-responsive.

Without wishing to be limited, other polysaccharides (e.g., but not limited to chitosan, hyaluronic acid, starch, pullulan, cellulose, and heparin) can also be modified to include a release trigger. For example, chitosan may be modified in a manner similar to the modifications of dextran as described herein.

In general, any polymers that contain either —OH, —$NH_2$, and/or —NHR' may be modified to include a release trigger. For example, a polymer containing —OH, —NH2, and/or —NHR' may be modified in a manner similar to the modifications of dextran as described herein.

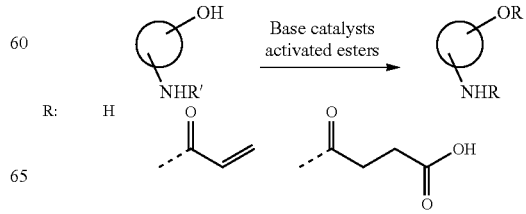

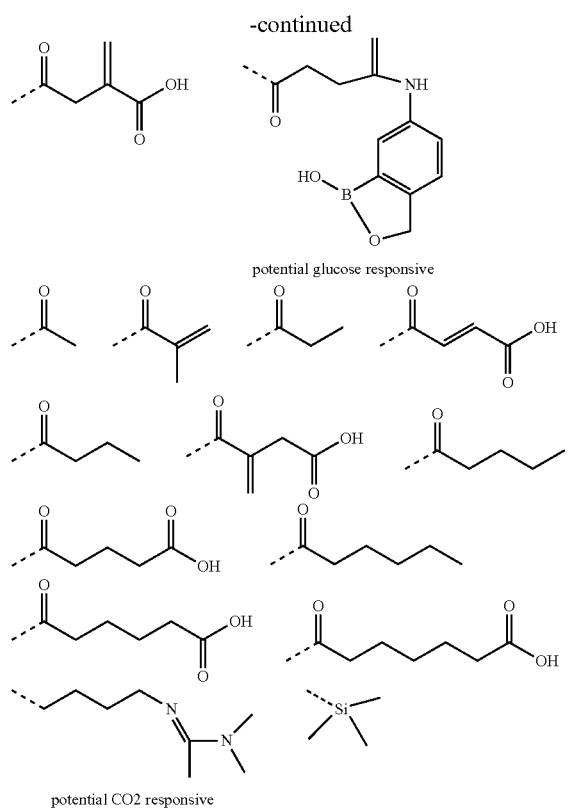

potential glucose responsive potential CO2 responsive

The hydrophobic and/or release trigger chemical moieties can be introduced into the polymers described herein by any methods known in the art or described herein. For example, the hydrophobic and/or release trigger chemical moieties can be introduced into the polymers described herein via esterification as shown above, or ring-opening of epoxy or reaction with isocyanate, for example as shown below.

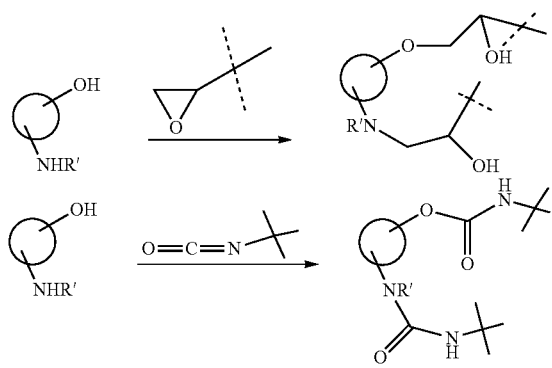

Monomers

Monomers (or the building blocks of polymers) may also be used as a component of the particle. Monomers include for instance, the building blocks of sugars, such as sucrose and lactose.

Other Agents that can be Included in the Particles or Shell Described Herein

Stabilizing Agents

As generally defined above, one aspect of the present disclosure is a particle comprising a stimuli-responsive shell encapsulating one or more gases, wherein the shell or optional sheath membrane includes one or more additional components such as a stabilizing agent, e.g., in addition to stabilization by covalently bound and/or non-covalently bound components of the shell. For example, stabilization of the membrane may further include non-covalent and/or covalent stabilization, and in that case, the addition of the stabilizing agent further stabilizes the shell.

As used herein, a "stabilizing agent" refers to a compound capable of preventing particle aggregation and/or decomposition of the particle, and which aids in membrane formation at the gas/liquid interface. In certain embodiments, the stabilizing agent contains a hydrophobic component, which orients itself towards the gas filled core, and a hydrophilic component, which interacts with the aqueous phase and minimizes the energy of the particle, thereby enabling its stability.

In certain embodiments, the stabilizing agent is a hydrophilic material, e.g., a hydrophilic polymer, lipidic material, or carbohydrate, attached to a hydrophobic anchor via one or more covalent bonds. Hydrophilic, in this context, refers to a moiety of the polymer, lipidic material, or carbohydrate which orients itself towards an aqueous or hydrophilic environment. Hydrophobic, in this context, refers to a moiety which orients itself away from an aqueous or hydrophilic environment, and towards a non-aqueous (e.g., gaseous core) environment. In certain embodiments, the hydrophobic anchor is a lipid group, as described herein.

The prevention of aggregation involves two main methods for stabilization, electrostatic and steric stabilization. In electrostatic the particles are made to repel each other, in steric the particles have large polymers (like polyethylene glycol) sprouting from there surfaces to physically prevent aggregation. It is also possible to enhance the viscosity of the solution in which the particle are immersed as to physically prevent touching. Other types of stabilization refer to prevention of degradation of the particle or the drug it houses. For instance, tocopherol prevents lipid oxidation. Also some humidity reducing agents that stops hydrolysis of PLGA are useful for this purpose.

The concentration of each of the various stabilizing agents can vary and optional concentrations can be determined via routine methodology. In certain embodiments, the stimuli-responsive shell comprises from 0.1 to 20%, or from 5 to 10% of a stabilizing agent.

Detergents

A wide variety of detergents can be used as a component of the particle, e.g., provided in the stimuli-responsive shell and/or the sheath membrane. Detergents, as used herein, include emulsifiers, surfactants, and wetting agents. Some detergents may also be used as stabilizing agents. Some detergents may also be used to adjust the release trigger contained in the stimuli-responsive shell. For example, surfactants or additives may be used to shift the lower critical solution temperature of poly(N-isopropyl acrylamide), a thermosensitive polymer, from 32° C. body temperature.

Steroids

Steroids may also be used as a component of the particle, e.g., provided in the stimuli-responsive shell and/or the sheath membrane. Some steroids may also be used as stabilizing agents, e.g., sterols such as cholesterol. In certain embodiments, the shell comprises cholesterol; however, in certain embodiments, the shell does not include cholesterol. In certain embodiments, the steroid is modified, e.g., by substitution or comprising a group X or Y attached to the steroid, to form covalent crosslinkages, and/or by substitution with one or more lipid tails.

Anti-Oxidants

In certain embodiments, the stimuli-responsive shell and/or the external crosslinked shell further comprises an anti-oxidant (e.g., non-enzymatic anti-oxidant). Exemplary anti-oxidants include, but are not limited to, tocopherol (vitamin E), vitamin A, glutathione, carotenoids (e.g. lycopene, lutein, polyphenols, β-carotene), flavonoids, flavones, flavonols, glutathione, N-acetyl cysteine, cysteine, lipoic acid, ubiquinal (coenzyme Q), ubiquinone (coenzyme Q10), melatonin, lycopene, butylated hydroxyanisole, butylated hydroxytoluene (BHT), benzoates, methyl paraben, propyl paraben, proanthocyanidins, mannitol, and ethylenediamine tetraacetic acid (EDTA).

In certain embodiments, the anti-oxidant is tocopherol.

Cryoprotectants

In certain embodiments, the stimuli-responsive shell and/or the external crosslinked shell further comprises a cryoprotectant. A cryoprotectant is a substance that is used to protect a material from freezing damage. Cryoprotectants may also function by lowering the glass transition temperature of a material. In this way, the cryoprotectant prevents actual freezing, and the material maintains some flexibility in an amorphous state. Many cryoprotectants also function by forming hydrogen bonds with biological molecules as water molecules are displaced. Exemplary cryoprotectants include, but are not limited to, glycols (alcohols containing at least two hydroxyl groups, such as ethylene glycol, propylene glycol, and glycerol), dimethyl sulfoxide (DMSO), and sugars such as sucrose.

Gas Core

As generally understood from the present disclosure, the gas core of the particle contains one or more gases. The gas core is the gas encapsulated within the stimuli-responsive shell. In certain embodiments, the gas core does not contain a fluorinated gas. In certain embodiments, the gas core does not contain a perfluorocarbon-based liquid. In certain embodiments, the gas core does not contain a hemoglobin, e.g., a natural or synthetic hemoglobin.

In certain embodiments, the gas is a biological gas, e.g., a gas used for therapeutic purposes.

In this context, the gas must be pharmacologically acceptable, i.e., must be biocompatible and have minimal toxicity when released. The shell of the particles described herein can be tuned to allow gas diffusion following administration. Exemplary gases include, but are not limited to, nitrogen, carbon dioxide, nitric oxide, helium, inhalational anesthetics, and neuroprotective gases (e.g., argon or xenon or hydrogen sulfide).

In other embodiments, the gas is not a biological gas, and is useful for non-therapeutic purposes.

The gas may be in the gas core alone or in combination with one or more other gases. For example, the gas core may contain a gas mixture containing oxygen and one or more additional gases. In certain embodiments, the gas is oxygen. In certain embodiment the gas is a mixture of oxygen and another gas. In certain embodiments, the gas contained within the particle may be a biological gas other than oxygen, including, but not limited to, nitric oxide, and inhalational anesthetics, such as isoflurane.

In certain embodiments, the volume of the gas core comprises about 10%, 20%, 30%, 40%, 50%, 60%, 70%, 80% 90%, 95%, 99%, 99.9% or 99.99% of gas, e.g., the volume of the gas core comprises between about 10% to about 99.99%, inclusive, of gas. In certain embodiments, the volume of the gas core is 50 to 60% of the overall volume of the suspension. In certain embodiments, lower volume percentages are preferred, e.g., between about 5% to about 50% gas. Particle suspensions containing less than 80% gas (by volume), may be useful when resuscitation is desired in trauma, or in microvascular flaps being treated with particles. In some embodiments, the gas content in a concentrated suspension is at least 10%, 20%, 30%, 40%, 50%, 60% (e.g., 70%, 80%, or 90%) by volume.

Pressurized Gas

The gas filled particles may be pressurized. In a pressurized gas particle the amount of gas per particle can be increased significantly. Pressurization techniques for making gas filled polymers that are pressurized are known in the art and for instance are described in patents such as U.S. Pat. No. 4,344,787.

Particle Size

As understood from the disclosure, the size of the particles described herein can range from microns to millimeters. In some embodiments, the particles described herein are microparticles. A microparticle has a particle diameter of between about 0.001 microns to about 500 microns. In certain embodiments, the particle has a diameter of about 0.02 microns to about 50 microns, e.g., about 0.05 microns to 40 microns, about 0.05 microns to 30 microns, about 0.05 microns to 20 microns, about 0.05 microns to 10 microns, about 0.05 microns to 6 microns, about 0.05 microns to 5 microns, about 0.05 microns to 4 microns, about 0.05 microns to 3 microns, about 0.05 microns to 1 micron, about 0.05 microns to 0.5 microns, 5 microns to 10 microns, 2 microns to 5 microns, 2 microns to 3 microns, 0.05 microns to 1 micron, or about 0.1 microns to 3 microns, inclusive.

In certain embodiments, 90% of the particles of a batch are within the above recited diameters (referred to as the "D90").

The overall diameter of the particle is selected to provide a high surface area to volume ratio, thereby favoring rapid transfer of the gas out of the particles.

The stable particles can have a particle size that is within the above recited diameters to suit the need of medical or non-medical applications. For example, for delivery of oxygen to a patient, typically, the particle has diameters of about 10 microns or smaller, preferably the upper limit for the diameter of the particles ranges from 7 microns or smaller, or 5 microns or smaller in order to pass through the pulmonary capillary bed following intravenous injection. In certain embodiments, the diameter below which 90% of the particles share (D90) is between about 2 to about 3 microns, inclusive, for intravenous particles. In certain embodiments, the diameter below which 90% of the particles share (D90) is between about between about 0.001 microns and about 1 micron, inclusive, for inhalational particles. As another example, the size of the particles can be as large as several hundred microns to millimeters for non-medical applications.

The size of these particles can be determined using a suitable device, e.g., Accusizer® or Multisizer® III. Microscopy can be applied to directly visualize the particles in the concentrated suspension. Dynamic light scattering may be used for particles less than 2 microns. Accusizer using light obscuration may be used to examine larger particles.

Stimuli-Responsive Shell and Sheath Membrane

As generally understood from the present disclosure, the present invention provides particles which comprise a stimuli-responsive shell which encapsulates a gas, and which optionally further includes a sheath membrane.

In certain embodiments, the stimuli-responsive shell (e.g., comprising nanoparticle aggregates) is between 1 and 500 nm thick, between 10 and 400 nm thick, between 20 and 300 nm thick, or between 5 and 100 nm thick, inclusive. In certain embodiments, the stimuli-responsive shell is a monolayer about 10 nm thick. A thin stimuli-responsive shell increases gas carrying capacity, while preventing a direct gas-blood interface.

In some embodiments where the particle further comprise a sheath membrane, the sheath membrane may be between 1 and 100 nm thick, between 1 and 10 nm thick, or between 2 and 5 nm thick, inclusive.

In certain embodiments, the nature of the stimuli-responsive shell and optionally sheath membrane impart a stability to the particle, wherein the shelf-life is greater than 3 months, e.g., greater than 4 months, 5 months, 6 months, 7 months, 8 months, 9 months, 10 months, 11 months, or 12 months (1 year). In certain embodiments, the shelf-life of the particle is greater than 1 year, e.g., 1.5 years, 2 years, 2.5 years, or more. For example, the stable particles retain at least about 70% or higher (including, e.g., at least about 80%, at least about 90%, at least about 95%, at least about 98%, at least about 99%, or up to 100%) of the gas fraction inside the particles and/or particle size after storage for a period of time, e.g., a period of greater than 3 months, greater than 6 months, or greater than 1 year.

Pharmaceutical Compositions and Suspensions

As generally understood from the present disclosure, the particles as described herein may be formulated as a pharmaceutical composition for administration or as a suspension (e.g., emulsion) for storage.

Pharmaceutical compositions and suspensions of the particle may comprise a pharmaceutically acceptable excipient, which, as used herein, includes any and all solvents, dispersion media, diluents, or other liquid vehicles, dispersion or suspension aids, surface active agents, isotonic agents, viscosity enhancing agents (e.g., thickening agents), preservatives, solid binders, lubricants and the like, as suited to the particular formulation desired. Remington's The Science and Practice of Pharmacy, 21st Edition, A. R. Gennaro, (Lippincott, Williams & Wilkins, Baltimore, Md., 2006; incorporated herein by reference) discloses various excipients used in formulating compositions and suspensions and known techniques for the preparation thereof. Except insofar as any conventional excipient is incompatible with a substance or its derivatives, such as by producing any undesirable biological effect or otherwise interacting in a deleterious manner with any other component(s) of the compositions or suspensions, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of the compositions and suspensions include, but are not limited to, inert diluents, dispersing agents, surface active agents and/or emulsifiers, disintegrating agents, preservatives, buffering agents, lubricating agents, and/or oils. Excipients such as coloring agents can be present in the compositions or suspensions, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc. and combinations thereof.

Exemplary dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, crosslinked poly(vinyl-pyrrolidone) (crospovidone), sodium carboxymethyl starch (sodium starch glycolate), carboxymethyl cellulose, crosslinked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an antioxidant. In other embodiments, the preservative is a chelating agent.

Exemplary buffering agents include, but are not limited to, dextrose buffer solutions (e.g., 10% dextrose buffer solutions), citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc. and combinations thereof.

For in vivo or medical applications, the compositions and suspensions as described herein should be generally isotonic with blood. Thus the compositions and suspensions may also contain small amounts of one or more isotonic agents. The isotonic agents are physiological solutions commonly used in medicine and they comprise water, aqueous saline solution, e.g. 0.9% NaCl, 2.6% glycerol solution, lactated Ringer's solution, and 10% dextrose solution, biologically compatible organic solvents (e.g., DMSO), and/or commercially available intravenous fluid or blood.

The compositions and suspensions may also be mixed with volume expanders, such as Hextend, hetastarch, albumin, 6% Hydroxyethyl Starch in 0.9% Sodium Chloride Infusion (Voluven), etc. The compositions and suspensions can also be mixed with blood (e.g. packed red blood cells) or hemoglobin-based oxygen carriers. Additionally, the compositions and suspensions can be mixed in a physiologic buffer (e.g. tris(hydroxymethyl) aminomethane, "THAM"). This is particularly useful in a clinical situation of impaired ventilation. In other embodiments, the compositions and suspensions can contain one or more cryoprotectants, e.g., glycols such as ethylene glycol, propylene glycol, and glycerol. The compositions or suspensions may further comprise an aqueous solution comprises a calcium salt for enhanced stability.

The particles may also be suspended in a medium (e.g., an aqueous and/or organic medium) comprising a viscosity enhancing agent. Such particles may also be prepared in such a medium, as further described herein. Exemplary viscosity enhancing agents for use as a component of a storage medium and/or a preparative medium include, but are not limited to, corn syrup (e.g., Clearsweet corn syrup (CS)); glycerin; cellulose derivatives (e.g., methylcellulose (MC); hydroxypropylmethylcellulose (HPMC); carboxymethylcellulose (CMC); microcrystalline cellulose (CC); ethyl cellulose; hydroxyethyl cellulose (HEC); hydroxypropyl cellulose (HPC); cellulose); gelatin; starch; hetastarch; poloxamers; pluronics; sodium CMC; sorbitol; acacia; povidone; carbopol; polycarbophil; chitosan; alginate; chitosan glutamate; hyaluronic acid; elastin; hyaluronan; maltodextrin DE; deoxyglycocholate (GDC); polymethacrylic acid; glycols (e.g., polymethylene glycol; polyethylene glycol); cyclodextrins (e.g., sulfobutylether B cyclodextrin); sodium tauro-dihydrofusidate (STDHF); and N-trimethyl chitosan chloride (TMC). In certain embodiments, the viscosity enhancing agent is corn syrup (e.g., Clearsweet corn syrup (CS)) or glycerin.

In certain embodiments, the particles are suspended in a medium (e.g., an aqueous and/or organic medium) comprises between about 5% to about 90% by weight of one or more viscosity enhancing agents, e.g., between about 5% to about 85%, between about 5% to about 80%, between about 5% to about 75%, between about 5% to about 70%, between about 5% to about 65%, between about 5% to about 60%, between about 5% to about 55%, between about 5% to about 50%, between about 5% to about 45%, between about 5% to about 40%, between about 10% to about 80%, between about 15% to about 80%, between about 20% to about 80%, between about 25% to about 80%, between about 30% to about 80%, between about 35% to about 80%, between about 40% to about 80%, between about 45% to about 80%, between about 50% to about 80%, or between about 25% to about 75%, inclusive.

As generally understood from the above, the medium (e.g., an aqueous medium and/or organic medium) which comprises one or more viscosity enhancing agents is a viscous medium. A viscous medium is defined as a fluid whose viscosity is sufficiently large to make viscous forces.

In certain embodiments, the gas-filled microparticle compositions and suspensions described above can be formulated in a manner suitable for topical administration, e.g., as a liquid and semi-liquid preparation that can be absorbed by the skin. Examples of a liquid and semi-liquid preparation include, but are not limited to, topical solutions, liniments, lotions, creams, ointments, pastes, gels, and emulgels.

In certain embodiments, the particle and/or pharmaceutical composition comprising the particle further includes a therapeutic agent, e.g., which can be, but are not limited to, hydrophilic or hydrophobic drugs, lipid-soluble drugs, nucleic acid-based drugs (including, e.g., genes, DNA, RNA, agRNA, smRNA, siRNAs, microRNAs, Crisper/Cas constructs, and/or nucleic acids for gene therapy), protein drugs such as antibodies, free radical scavengers, nitric oxide, a chemotherapeutic agent, a small molecule drug, and combinations thereof. In certain embodiments, the compositions and suspensions are co-formulated with one or more additional therapeutic agents for co-delivery of the gas or gas mixture inside the microparticles and the one or more agents, which can be, but are not limited to, hydrophilic or hydrophobic drugs, lipid-soluble drugs, nucleic acid-based drugs such as siRNAs or microRNAs, protein drugs such as antibodies, or free radical scavengers. In certain embodiments, the therapeutic agent is encapsulated in the core of the particle. Alternatively, in certain embodiments, the particle comprises a therapeutic agent attached to the outer surface of the particle, e.g., by covalent attachment or by non-covalent association with the membrane.

Any of the particle-containing suspension described herein can be either in suspension form or in dry powder form (e.g., obtained via spray drying or by lyophilization). When in dry powder form, the suspension can be mixed with a solution such as saline immediately before use.

The gas-filled particle compositions or suspensions described above can be used for gas delivery shortly after their preparation. If needed, they can be stored under suitable conditions (e.g., refrigerated conditions) before administration.

Additional methods of preparing these suspensions, dry particles and powers, and filling the particles with gas are described herein. See, for example, the methods of preparation and the Examples.

Further contemplated are kits or pharmaceutical packs comprising a particle and instructions for use. In certain embodiments, the kit comprises a container housing a particle, a container housing a pressurized aqueous phase mixture, and instructions for mixing the particle and the aqueous phase. In certain embodiments, the container housing the particle and the container housing the aqueous phase are separate compartments within a single container.

Methods of Treatment and Use

As generally understood from the present disclosure, some aspects provided are methods of delivering a gas to a subject in need thereof, the method comprising administering to the subject a pharmaceutical composition comprising a particle as described herein and a pharmaceutically acceptable excipient. The gas-filled particles described herein can be used to deliver a gas into a subject, thereby treating various diseases and conditions. The gas-filled particles may be administered to any subject, tissue or organ in need thereof, i.e., in need of the gas to be delivered, e.g., by intravenous, intraosseous, intraperitoneal, intraarterial, subcutaneous, and/or intramuscular injection or infusion; alternatively it can be topically applied as a powder or wetted, or inhaled, ingested or applied topically to a body cavity, such as the pleura, the pericardium or the peritoneum or administered peritoneal or retroperitoneal. The particles may be administered alone or in combination with other treatments as an adjunctive therapy. Depending upon the need of a subject, the particle can be designed such that they release the gas or gas mixture immediately following administration (e.g., <10 milliseconds to 1 minute). Alternatively, the particles can be designed to provide sustained release of the gas or gas mixture, and/or to persist in vivo until they reach the target tissue, where the membrane collapses to release the gas or gas mixture.

The term "treating" as used herein refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disease/disorder, the symptoms of the disease/disorder, or the predisposition toward the disease/disorder.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds.

In certain embodiments, the subject is or is suspected of experiencing local or systemic hypoxia. In certain embodiments, the subject has or is suspected of having a disease or disorder selected from the group consisting of congenital physical or physiologic disease, transient ischemic attack, stroke, acute trauma, cardiac arrest, exposure to a toxic agent, heart disease, hemorrhagic shock, pulmonary disease, acute respiratory distress syndrome, infection, solid hypoxic tumor, and multi-organ dysfunction syndrome.

An "effective amount" is the amount of the particles that alone, or together with one or more additional therapeutic agents, produces the desired response, e.g. increase in the local or systemic level of a desired gas such as oxygen in a subject or increases the tissue PO2 in a particular target organ. In the case of treating a particular disease or condition, the desired response can be inhibiting the progression of the disease/condition. This may involve only slowing the progression of the disease/condition temporarily, although more preferably, it involves halting the progression of the disease/condition permanently. This can be monitored by routine methods. The desired response to treatment of the disease or condition also can be delaying the onset or even reducing the risk of the onset of the disease or condition. An effective amount will depend, of course, on the particular disease/condition being treated, the severity of the disease/condition, the size of the patient, the volume of distribution of the drug, the individual patient parameters including age, physical condition, size, gender and weight, the duration of the treatment, the nature of concurrent therapy (if any), the specific route of administration and like factors within the knowledge and expertise of a health practitioner. These factors are well known to those of ordinary skill in the art and can be addressed with no more than routine experimentation. It is generally preferred that a moderate dose of the particles be used, that is, the highest safe dose according to sound medical judgment, taking into account that following a hypoxic injury, for example, an excessive or even normal oxygen tension may be harmful during the recovery period.

A. Therapeutic Applications of Gas-Filled Particles

Suspensions containing oxygen-filled particles as described herein can be used to restore the oxygen level in a patient experiencing or being suspected of experiencing local or systemic hypoxia via any of the methods described above. Thus, they have broad therapeutic utilities, including treatment of traumatic brain injury, cardiac arrest (via either intraarterial infusion or intravenous infusions), promotion of wound healing, topical augmentation of oxygen delivery (as topically administered to a body cavity or enterally administered) and preservation of organs during transplant.

After the gas-filled particles are delivered into a subject, the gas core reaches an equilibrium across the membrane between the gas core and the surrounding plasma, which may include desaturated hemoglobin. When the gas core contains oxygen, it binds rapidly to hemoglobin, which provides an "oxygen sink." This strongly favors a tendency of oxygen to leave the particle's core rather than remain within it. When particles reach capillaries intact, oxygen may equilibrate directly with surrounding tissues without interposed hemoglobin as an oxygen carrier.

Fully saturated whole blood with physiologic hemoglobin contains 16-20 mL oxygen per dL. Particle suspensions can be manufactured to contain between 40 and 70 mL oxygen per dL of suspension. Thus, the injection of one dL of suspension can deliver about 40-70 mL of oxygen directly to a tissue or organ in need of immediate oxygenation. In certain embodiments, oxygen is delivered at an infusion rate of 10 to 400 mL/minute to the subject.

The particles may be administered in an effective amount and at suitable rate for increasing or maintaining the PO2 in a subject following administration. Typically, the particles are administered in an effective amount and at suitable rate to deliver an effective amount of oxygen to a subject to ischemic tissues or to desaturated blood in a time ranging from 0.5 to 30 seconds following administration, wherein the amount of oxygen that is delivered is effective to restore PO2 levels to normal levels or prevent or alleviate hypoxic injury. In certain embodiments, the particles provide sustained release of oxygen; such particles may be used, for example, to deliver oxygen or other gas to the brain and other tissues.

Cerebral Protectant During Childbirth

An effective amount of suspension containing oxygen- or other gas-filled particles and optionally other therapeutic agents can be administered into the epidural, subdural, or subarachnoid (or nearby) spaces during intrapartum distress so as to maintain sufficient oxygen supply to the neonate, thereby reducing the risk of cerebral damage during childbirth.

Provide Oxygen Supplementation Via the Enteral Route

Oxygen-filled particles and, optionally, lipid nutrients, carbohydrates, or other nutrients found in blood (e.g., glucose and other blood components), can be delivered via the enteral route, e.g., to a site in the abdominal cavity, such as the intestine or the peritoneum, to provide an alternate source of intestinal oxygenation and prevents or mitigates intestinal ischemia, which may contribute to necrotizing enterocolitis, a leading cause of pediatric morbidity and mortality in preterm infants. This may also decrease the burden of anaerobic bacteria in the bowel, decreasing the risk of bacterial translocation and sepsis. This can also benefit prematurely born infants as it may decrease toxicity to premature lungs, prevents retinopathy of prematurity, and also provides lipid nutrition at the same time. In addition, it may be used in adults such as COPD patients, who require supplemental oxygen for some reason. It may also provide an alternative method of providing supplemental oxygen to critically ill patients such as ARDS patients, in whom increasing oxygen delivery through the lungs may be prohibitively injurious.

Preservation of Organ and Blood In Vitro

Low blood oxygen tensions within stored blood may contribute to the blood storage defect, causing cells within the plasma to generate lactate and toxins, which may decrease the therapeutic value of transfused blood and diminish its shelf life. Oxygen-filled particles may be added to a blood sample periodically to prolong in vitro blood storage. In an explanted organ, a suspension containing oxygen-filled particles can be delivered into a blood vessel in an organ to provide oxygen supply, thereby ameliorating tissue damage due to hypoxia. This is particularly useful in preserving organs to be used in transplantation. In addition, oxygen-filled particles can be added to a blood sample periodically to prolong in vitro blood storage.

Promote Wound Healing

Delivery of oxygen-filled particles to a wound site or a site nearby a wound can provide a continuous supply of oxygen to the wounded tissue, which is essential to the healing process. Thus, this approach benefits healing of a wound, such as that associated with a disease or disorder (e.g., diabetes, peripheral vascular disease, or atherosclerosis). In some embodiments, the suspension is prepared as a topical formulation for treating external wounds. The wound may be, for instance, a burn. The invention also contemplates bandages or would healing devices comprising the particles of the invention.

Improve Efficacy of Tumor Radiotherapy and/or Cancer Immunotherapies and Reduce Side Effects Caused Thereby Tumor radiotherapy often damages non-cancerous tissues nearby a tumor site. Applying an effective amount of oxygen-filled particles delivered locally or systemically can reduce such damage by increasing the oxygen content of a local tumor environment. In addition, it also can increase the effects of ionizing radiation delivered to the tumor, thereby improving efficacy of a radiotherapy. In some embodiments, the oxygen-filled particles can also include carbon dioxide gas, e.g., as described in Janssens et al. "Accelerated radiotherapy with carbogen and nicotinamide for laryngeal cancer: results of a phase III randomized trial" *J Clin Oncol* (2012) 30: 1777-83. In some embodiments, the particles are delivered directly to a tumor site. In others, the particles are administered to a site nearby a tumor.

Localized oxygen delivery can also increase intratumoral oxygen tensions, which can improve the efficacy of endogenous and adoptive immunotherapies or cancer immunotherapies. Accordingly, in some embodiments, the stable particles described herein (e.g., encapsulating oxygen) can be used, in combination with cancer immunotherapies, to deliver oxygen to solid hypoxic tumors, while improving the efficacy of cancer immunotherapies. See, e.g., Hatfield et al. "Immunological mechanisms of the antitumor effects of supplemental oxygenation" *Science Translational Medicine* (2015) 7: 277ra30 for the antitumor effects of supplemental oxygenation. In some embodiments, the stable particles described herein (e.g., encapsulating oxygen) can be administered to deliver oxygen to solid hypoxic tumors while improving the efficacy of endogenous and adoptive immunotherapies.

Immunotherapies

Delivery of oxygen-filled stable particles described herein can be used for immunotherapies. In some embodiments, the stable particles can include hydrogen.

Ameliorate Sickle Cell Crisis

Sickle cell crisis refers to several independent acute conditions occurring in patients with sickle cell anemia, including acute chest syndrome (a potentially lethal condition in which red blood cells sickle within the lungs and lead to necrosis, infection and hypoxemia), vasoocculsive crisis (i.e., obstruction in circulation caused by sickled red blood cells, leading to ischemic injuries), aplastic crisis (acute worsening of the baseline anemia in a patient, causing pallor, tachycardia, and fatigue), splenic sequestration crisis (acute, painful enlargements of the spleen), and hyper hemolytic crisis (acute accelerated drops in hemoglobin level). Administering an effective amount of oxygen-filled particles to a sickle cell anemia patient or a subject suspected of having the disease can reduce sickle cell crisis, in particular, vaso-occlusive crisis, in part because the sickle crisis is perpetuated by local and regional hypoxemia.

Improve Anti-Infective Activity of Immune Cells

Oxygen-filled particles can be preferentially taken up by lymphocytes of varying types, including macrophages so as to raise intracellular oxygen tension. This may potentiate lymphocyte killing of microbial agents by enabling superoxide dismutase and the production of intracellular free radicals for microbicidal activity without causing resistance.

Treatment of Anaerobic Infections

Administration of oxygen-filled microparticles via the topical, intravenous, intraarterial, intradermal, intramuscular, enteral or other route may provide a potent mechanism to counter anaerobic infections. This mechanism may be particularly attractive due to its alternative mechanism of action—this is unlikely to be countered by typical bacterial resistance mechanisms.

Minimize Organ Injury During Cardiopulmonary Bypass in Adults, Children, and Neonates During cardiopulmonary bypass operations, the heart must be cross-clamped (i.e. no oxygen delivery to the myocardium) and cooling/protective agents reduce myocardial oxygen consumption. Additionally, some portions of the surgery in neonates and children utilize deep hypothermic circulatory arrest in which all of the blood is removed from the body and all cannulas removed. Use of oxygen-filled particles to add a small amount of oxygen supply on a continuous basis to organs or to the blood used to deliver the cold cardioplegia solution would better protect the heart, brain and other organs and mitigate post-cardiac bypass injury. The majority of the oxygen-filled particles is gas, which could be consumed by the myocardium, leaving only a lipid shell and a small amount of carrier, if any. This is important because a large volume of perfusate cannot be used due to obscuration of the surgical field. This may provide a way to keep a clean surgical field while still providing oxygen to the myocardium, with or without hemoglobin as an intermediary.

For example, in one aspect, provided is a method of delivering a gas to a subject during cardiopulmonary bypass surgery, comprising administering to the subject during the surgery a pharmaceutical composition comprising a gas-filled particle. In certain embodiments, the pharmaceutical composition is administered to the blood of the subject. In certain embodiments, the pharmaceutical composition is administered to the blood upstream of a filtration device.

Oxygenate Venous Blood in Myocardial Infarction Patients

During a heart attack (myocardial infarction), an arterial thrombus prevents perfusion and therefore oxygen delivery to a selected region of myocardium. Perfusing the right atrium (through an intravenous injection) with highly oxygenated blood, via delivery of oxygen-filled particles, and providing a high coronary sinus pressure via a high right atrial pressure can back-perfuse a region of ischemic myocardium via the coronary sinus and venous plexus of the heart. The majority of the volume of the injectate (i.e., gas) will be consumed and disappear, allowing a continuous infusion into a dead-end space (i.e. a venous plexus feeding a region of myocardium previously fed by a thrombosed coronary artery, whether partially or completely obstructed. The thin-walled atrium may directly absorb oxygen from the oxygen-rich right atrial blood. In practice, using oxygen-filled particles can be an easy way to perfuse the heart with oxygen rich blood during acute coronary syndrome. For example, the oxygen-filled particles can be delivered using an occlusive balloon catheter blown up in the coronary sinus with a power-injection of oxygen-rich suspension into the coronary sinus such that the suspension could flow retrograde throughout the heart, including the region affected by the coronary thrombus (because there would be no clot on the venous side).

Cardiopulmonary Bypass Surgery

During cardiopulmonary bypass surgery the blood of a patient is circulated through a filtration device. The particles of the invention may be delivered directly to the patient or to the blood as it is being circulated outside of the body. In some embodiments the particles are administered upstream of a filtration device. An advantage of this embodiment is that the gas can be delivered to the blood and then the particles are removed by filtration before the blood is returned to the body.

Reduce Cardiac Arrhythmia During Coronary Angiography

Cardiac arrhythmia, even fatal arrhythmia, is a common adverse effect during coronary angiography in both adults and children for diagnostic or therapeutic purposes. Using an oxygen-filled particle suspension (e.g., of approximately 20 mL/dL oxygen) optionally mixed with a contrast agent allows for sustained oxygen delivery to sick myocardium during a selected injection of a coronary artery and prevents a substantial number of adverse events and deaths from these risky procedures.

Replace Blood During Bloody Procedures or in Early Resuscitation in Trauma

Oxygen-filled particles capable of translocating oxygen directly to mitochondria can be used as "blood replacement" during bloody procedures or in the early resuscitation in trauma. This would of course be a temporizing procedure such that the 'blood' lost via a bleeding source (e.g. the back during a spinal fusion, other arteries during many bloody procedures) would contain mostly non-blood components. The majority or all of the blood could be removed at the beginning of an operation and the body can be perfused with a suspension of the oxygen-filled particles (which may further contain a buffer for the absorption of carbon dioxide, energy substrates such as glucose, and clotting factors such as platelets, FFP and cryoprecipitate) during the operation. Once the bloody portion of the procedure is near the end, the blood could be replaced, and the perfusate of oxygen-filled particles could quickly go away due to absorption of oxygen gas and renal filtration (or mechanical ultrafiltration) of the diluent. When necessary, suspensions containing ~90-95 mL of oxygen gas per dL of suspension may be used given the prolonged time (hours) of providing for the body's entire oxygen consumption.

Cyanotic Congenital Heart Disease

A unique feature of congenital heart disease is partial or complete mixing of saturated and desaturated blood. In perioperative states, systemic desaturation can lead to significant cerebral and myocardial dysfunction. For example, frequently subjects with hypoplastic left heart syndrome require extracorporeal life support in the perioperative period primarily to prevent death due to hypoxemia and the concomitant myocardial dysfunction. ELSO. Extracorporeal Life Support Registry Report, International Summary; 2008 January, 2008.

Particles containing oxygen may be administered intravenously in an effective amount to raise mixed venous oxygen content, systemic arterial oxygen content, and improve myocardial function in subjects in a perioperative states. Thus the particles can be administered in place of a more invasive use of extracorporeal life support device.

Traumatic Brain Injury

Infusion of oxygen-bearing particles into the cerebral circulation may decrease neuronal death at the ischemic penumbra. Given the improved oxygen content of particle suspensions over that of whole blood, subjects with impaired cerebral blood flow, e.g. in traumatic brain injury or intracranial hypertension, directed administration of oxygenated particles into a carotid artery would increase the oxygen content (Ca O2) of blood flow directed to the brain, and may balance the decrease in flow with an improvement in oxygen content.

Treat Pulmonary Hypertension

Perfusion of the venous system, and therefore the pulmonary arteries and arterioles, with 'blood' rich in oxygen, nitric oxide, or other gaseous vasodilators can more effectively relax the pulmonary arterioles (putatively a major contributor to the pathology of pulmonary hypertension). This would be most effective during a pulmonary hypertensive crisis, a potentially fatal event in which high pulmonary pressures cause a decrease in blood flow to the left heart and decreased cardiac output. Accordingly, a venous injection of a suspension containing oxygen-filled particles can quickly reverse the process. This approach could be more effective than delivering oxygen to the lungs via inhalation because of its exposure to the pulmonary arterioles, which are the farthest point in the circulation from the pulmonary capillaries.

Treat Pulmonary Embolus or Hypertension

In near-fatal pulmonary embolus a defect could be created in the atrial septum to permit the flow of venous blood across the atrial septum to allow filling of the left heart (a Rashkind balloon atrial septostomy) from the right heart, bypassing the lungs temporarily. In this setting, a suspension containing oxygen-filled particles can be used to oxygenate blood, thereby permitting time and clinical stability for a surgical thrombectomy, catheter based interventions or medical therapies to be applied to the clot.

Treat Carbon Monoxide Poisoning

Subjects (including patients, soldiers) with severe carbon monoxide poisoning are currently treated with hyperbaric oxygen. This is an expensive and scarce resource, and is impractical for unstable patients due to the technical constraints of the hyperbaric chamber itself. The oxygen-filled particles described herein can be used to create hyperbaric oxygen conditions (i.e. the oxygen content of the blood under hyperbaric conditions is 22-24 mL/dL versus 20 at atmospheric pressure; additionally, pressurized oxygen microparticles could be used to raise the $PaO_2$ of blood to above 700 mmHg). More specifically, use of an oxygen-filled particle suspension containing, for example, 60-80 mL oxygen/dL of suspension, can displace carbon monoxide from hemoglobin and restore normal hemoglobin function as occurs in the hyperbaric chamber. This would obviate the need for a hyperbaric chamber, allow for the contemporaneous treatment of multiple subjects with carbon monoxide poisoning (e.g. terrorist attacks, house fires, soldiers), the treatment of ICU patients with CO poisoning, and permit the rapid reversal of CO poisoning at or near the point of injury (e.g. at the scene of a fire).

Reduce Injury Caused by Low Systemic Blood Oxygen Saturation

There are many congenital heart lesions in which desaturated blood (from the body) and oxygenated blood (from the lungs) mix in the heart. In some instances, e.g., immediately after a Norwood operation or unrepaired D-transposition of the great arteries, the degree of mixing or the degree of pulmonary blood flow causes the systemic oxygen saturations to be extremely low such that the body develops acidosis and organ injury. In these subjects, raising the oxygen tension of the systemic venous return by even a small amount would raise the systemic oxygen saturations significantly (due to mixing). This would avert a substantial number of subjects who currently are placed on ECMO for even a few days for this reason.

Resuscitation in Obstructed Systemic-Pulmonary Shunts

Several congenital heart lesions (e.g. hypoplastic left heart syndrome) are initially treated with a small tube graft from the innominate artery or the right ventricle to the pulmonary artery. The acute obstruction of these shunts (usually a B-T shunt) causes death within minutes and is an important cause of interstage mortality for these children. The availability to oxygenate the venous blood in these subjects, using the oxygen-filled particles described herein, would allow even a paramedic to effectively resuscitate a subject in need with oxygenated blood. This could also prevent death in a substantial number of hospitalized subjects in hospitals with or without the ability to rapidly place a subject onto ECMO.

Delivery of Oxygen-Filled Particles to Fetuses, Neonates and Infants

The gas filled particles may be administered to a fetus, neonate, or infant in need of additional oxygen. The gas filled particles may be administered to low birth weight infants or premature infants. In one embodiment, the particles filled with oxygen are administered in an effective amount to ensure that the fetus, neonate, or infant is receiving sufficient oxygen, particularly to ensure that the brain of the fetus, neonate or infant receives sufficient oxygen for development and maintenance of normal function.

If a mother is experiencing preeclampsia, the baby must be born. Optionally, the gas filled particles can be administered to the baby, mother, or both in effective amount to deliver an effective amount of oxygen to maintain normal bodily functions when the mother is experiencing preeclampsia.

Neonates with hypoxic ischemic brain injury at the time of birth often suffer from extensive brain injury, manifested as cerebral palsy. This may occur due to even brief periods of hypoxia during the peripartum period. In clinical situations where this is appreciated prior to delivery, such as a nuchal cord or placental abruption, injection of gas filled particles into the umbilical circulation or into the dural space may avert critical hypoxia and may ameliorate some forms of hypoxic ischemic brain injury in this setting.

Newborns with congenital heart disease can have diseases that cause profound cyanosis and organ injury. For example, newborn subjects with D-transposition of the great arteries receive systemic arterial blood flow from the right ventricle, blood flow which is not exposed to the lungs at all. In subjects with inadequate mixing at the atrial level, profound cyanosis can cause organ injury and death. These subjects could be stabilized and transported to definitive care by oxygenating the venous return via infusion of oxygen-filled particles. Subjects with obstructed pulmonary venous return, representing the only true pediatric congenital heart emergency, could be stabilized by creation of an atrial septal defect and oxygenation of venous return as discussed above.

Intestinal Ischemia

The particles of the invention are also useful for the enteral or peritoneal or retroperitoneal administration of oxygen to patients at risk of intestinal ischemia, including but not limited to premature infants at risk for necrotizing enterocolitis or adults with mesenteric ischemia Provide Inotropic Support Myocardium extracts a higher proportion of oxygen from the blood than any other organs. In post-cardiac bypass or post-myocardial infarction patients (exhibiting tissue edema and mitochondrial dysfunction), a catheter placed into the coronary root may allow delivery of oxygen-filled particles, thereby supersaturating the coronary blood flow and provide a novel route of inotropic support different from all current inotropic methods, all of which rely on the beta receptor. This approach could provide an effective inotropic supplement, especially to those patients with downregulated beta receptors.

Calculate Cardiac Output

Cardiac output is defined as the flow rate of blood through the heart and vasculature. It is possible that injection of a small volume of gas could be detected based on a change in oxygen saturation (by injecting oxygen filled particles into the veins of patients with a saturation below 98%, or alternatively, by infusing carbon dioxide, nitrogen or carbon monoxide, or other gas), and detecting the time it took to detect the change by standard pulse oximeter. Alternatively, one could utilize ultrasound to determine the time it took particles to travel from injection to the arterial system. This may be useful as a bedside tool to determine cardiac output, and would be useful even in children with cyanotic congenital heart defects.

Treat Multi-Organ Dysfunction Syndrome

Use of an oxygen-filled particle suspension with high oxygen concentration can be used to achieve extremely high oxygen tensions at the capillary level with or without hemoglobin. This would enhance the uptake of oxygen by dysfunctional mitochondria or through an inflamed endothelium.

Acute Respiratory Distress Syndrome (ARDS)

Refractory hypoxemia is the hallmark of acute lung injury and ARDS. Profound hypoxemia accounts for 10% of the mortality of this common disorder. Meade et al, "Ventilation strategy using low tidal volumes, recruitment maneuvers, and high positive end-expiratory pressure for acute lung injury and acute respiratory distress syndrome: a randomized controlled trial." JAMA, 299(6):637-45 (2008). Particles containing oxygen may be administered intravenously in an effective amount to alleviate the hypoxemia associated with severe intrapulmonary shunting and decrease the mortality and morbidity of ARDS.

Alternatively, nanoparticle or microparticles could be nebulized (with or without pressurization of the gas within it) and administered inhalationally to a patient. The particle may diffuse into pulmonary edema fluid and raise the oxygen tension of the fluid in the alveolar space, causing an increase in systemic oxygenation.

Hemorrhagic Shock

In acute hemorrhage, resuscitative trauma therapy focuses upon restoration of circulating blood volume and oxygen carrying capacity. In states of hypovolemic shock, such as resulting from severe blood loss, the oxygen extraction ratio of peripheral tissues is increased. The result is further desaturation of blood returning to the right heart. Models of blunt chest trauma and hemorrhagic shock have suggested that right ventricular (RV) dysfunction impedes resuscitation efforts.

In late hemorrhagic shock, myocardial ischemia causes impaired contractility. Volume resuscitation of an ischemic, dysfunctional right ventricle may lead to increased RV end-diastolic volume, causing septal shift into the left ventricle (LV), and decreased LV end-diastolic volume.

The oxygen-filled particles can be injected at an appropriate concentration and rate to deliver oxygen directly to the myocardium in a time period ranging from 3 to 10 second following injection. For example, if the oxygen-filled particles contains from 40 to 70 mL oxygen per dL of suspension, the injection of one dL of suspension could deliver approximately 40-70 mL of oxygen directly to the myocardium. Optionally, the oxygen-filled particles may contain a specialized resuscitation fluid, such as synthetic colloid (e.g. Hextend™) or hemoglobin-based oxygen carrier (HBOC) as the carrier.

Neurological Disease

Further contemplated is a method of delivering a gas to the brain of a subject suffering from a neurological disease. The subject may be delivered a neuroprotective gas such as a noble gas, e.g. argon. The particles may be designed to deliver the gas to the blood which will be delivered to the area of the brain. The gas can then pass through the blood brain barrier. Alternatively or additionally the particles may be designed such that they will cross the blood brain barrier. For instance the particles may be nanometer sized.

Organs

The particle of the invention may be delivered topically to a variety of organs including skin and internal organs.

Additional Therapeutic Methods Contemplated

Further contemplated is a method of delivering a gas to an organ of a subject, comprising topically administering to the organ of the subject a pharmaceutical composition comprising a gas-filled particle, wherein the pharmaceutical composition is topically administered directly to the organ. In certain embodiments, the organ is skin and a skin disorder or wound is treated. In certain embodiments, the wound is a burn.

Further contemplated is a method of delivering a gas to a subject having a neurological disease, comprising administering to the subject a pharmaceutical composition comprising a gas-filled particle in an effective amount to deliver the gas to the brain of the subject. In certain embodiments, the gas filled particles have an average particle size of less than one micron. In certain embodiments, the gas is a noble gas such as argon.

Delivery of a gas other than oxygen can confer various therapeutic benefits. For example, isoflurane-filled particles can be delivered to a subject having or suspected of having asthma for treating the disease. In another example, particles filled with an insoluble gas (e.g., nitrogen or a noble gas) can be used as a volume expander. Particularly, particles having a size of 1-5 microns do not pass through gap junctions and thereby serve as an excellent volume expander. Moreover, gaseous sedatives can be delivered via gas-filled particles to achieve a quick effect.

In some embodiments, the stable particles described herein can be filled with a gas-based antimicrobial agent and applied to skin of a subject for treatment of a skin condition, disease or disorder and/or facilitate wound healing. For example, in some embodiments, the stable particles described herein can be filled with ozone or a therapeutically active ozonated derivative, e.g., as described in Travagil et al. "Ozone and ozonated oils in skin diseases: a review" *Mediators Inflamm.* (2010) 2010:610418. In some embodiments, the stable particles described herein can be filled with nitric oxide. See, e.g., Hardwick et al. "A novel method for the delivery of nitric oxide therapy to the skin of human subjects using a semi-permeable membrane" *Clinical Science* (2001) 100: 395-400.

In some embodiments, the stable particles described herein can be used as a carrier to deliver an active agent other than a gas, e.g., for therapeutic applications. Thus, one aspect described herein relates to a stable particle having a shell surrounding a hollow core, wherein the shell includes a release trigger, and the hollow core comprises an active agent. Examples of an active agents include, but are not limited to therapeutic agents, drugs, and gene constructs.

In some embodiments, the stable particles described herein can be used for thernostics applications, e.g., plasmon-surfaced enhanced imaging, ultrasound contrast agents, and/or ultrasound induced blasting agents. For example, in some embodiments, the shell of the gas-filled stable particles described herein can further include a targeting moiety that specifically binds to a target to be detected and/or treated, e.g., a target cell, a target tissue, or a target biological object such as a kidney stone. By way of example only, in some embodiments, the shell of the gas-filled stable particles described herein can include a field-responsive release trigger (e.g., an ultrasound-responsive trigger) and a bisphosphonate tag to specifically target kidney stones. These stable particles may preferentially bind to the stone and not surrounding tissue. Ultrasound or another suitable form of energy can then be applied causing the gas-filled stable particles to induce cavitation and fragment the stones. This can be used as an adjunct to ureteroscopy or percutaneous lithotripsy to aid in fragmentation. Randall's plaques, which also contain hydroxyapatite crystals that bind to bisphosphonates with high affinity, can also be targeted to preemptively destroy these stone precursors. Additionally, targeted stable particles can aid in kidney stone diagnostics by virtue of being used as an adjunct to traditional imaging methods. See, e.g., Ramaswamy et al. "Targeted microbubbles: a novel application for the treatment of kidney stones" *BJU Int.* (2015) 116(1): 9-16 and/or WO 2013/028942, the contents of which are incorporated herein by reference.

In other embodiments, the stable particles can be used for detection and treatment of cancer. For example, the stable particles can encapsulate oxygen and/or anti-cancer agents within the stimuli-responsive shell, and the shell of the stable particles can comprise a pH release trigger, e.g., an acidic pH release trigger, and gold nanoparticles for use in optical imaging for detection of cancer. See, e.g., Wang, "Plasmon-resonant gold nanoparticles for cancer optical imaging" *Science China Physics, Mechanics and Astronomy* (2013) 56: 506-513.

In some embodiments, the stable particles can be loaded with polarized gas such as Xenon-129 and/or Helium-3 for magnetic resonance imaging in vivo, e.g., as described in U.S. Pat. No. 6,051,208, the contents of which is incorporated herein by reference.

In some embodiments, a foam or suspension comprising stable particles that include a light-responsive shell and encapsulate a photosensitizer that induces intracellular oxidation can be used for treatment of sclerosis. For example, a foam comprising stable particles that include a light-responsive shell and encapsulate a photosensitizer Temoporfin may be injected into a vein or target area. Upon light activation, the light-responsive shell may dissolve and release the photosensitizer Temoporfin, which is in turn activated and thus produces an intracellular oxidation that acts to induce morphologic changes in cells. See, e.g., the U.S. Pat. Appl. No. 2008/0275432, the content of which is incorporated herein by reference.

In addition to the therapeutic applications, gas-filled particles can also be used for non-therapeutic purposes, e.g., as MRI and ultrasound contrast agents, fuel additives, cosmetics, bioremediation, water treatment, inks, paints and coatings, lightweight packaging materials, lightweight electronic materials, lightweight materials, or research tools for defining the volume of oxygen exposed to an environment.

In addition to stabilizing the particles, it is possible that this technique may extend the utility of these particles to having alternative uses. Specifically, particles which persist in the bloodstream following oxygen transfer may be useful as dual purpose agents in trauma resuscitation. They may be useful as a volume expander in military applications because they are lightweight and, if properly designed, can be manufactured not to be able to leave the bloodstream and into the interstitial space following injection.

Ultrasound Contrast Agents and/or Ultrasound-Based Theranostic Agents and/or Other Applications In some embodiments, the stable particles described herein (e.g., stable particles having a shell surrounding a gas core, wherein the shell comprises nanoparticle aggregates, and the shell is porous) can be used for ultrasound and can improve diagnostics and/or drug delivery. In some embodiments, the stable particles are highly echogenic and are able to exhibit second harmonics, for example, possibly because of the nanoporous structure imparted on the stable particles during fabrication. This is a surprising discovery as no other traditional polymer shelled microparticles can achieve this result.

In some embodiments, the stable particles described herein (e.g., stable particles having a shell surrounding a gas core, wherein the shell comprises nanoparticle aggregates, and the shell is porous) cavitate at extremely low mechanical indices, which can make them valuable for targeted drug delivery and diagnostics using ultrasound. Thus, in some embodiments, the stable particles described herein can be used as ultrasound-based theranostic agents, e.g., for both imaging and therapeutic uses (e.g., but not limited to drug delivery, sonoporation).

In some embodiments, the stable particles described herein for use as ultrasound contrast agents and/or ultrasound-based theranostic agents are formed by nanoprecipitation.

In some embodiments, the stable particles described herein (e.g., stable particles produced by interfacial nanoprecipitation) comprise a porous shell, for example, that is made of nanoparticle aggregates, such that a gas inside the stable particles can be capable of oscillating freely to some extent through the interstitial capillaries within the porous shell, e.g., exhibiting non-linear behaviors to allow harmonic imaging using ultrasound. In some embodiments, by manipulating the shell compositions, the stable particles can be designed that cavitate at specific sound pressure, measured by mechanical index (MI).

In some embodiments, the stable particles described herein (e.g., stable particles having a shell surrounding a gas core, wherein the shell comprises nanoparticle aggregates, and the shell is porous) can exhibit second harmonic in response to an incident pressure wave, for example, at MI of about 0.05, about 0.06, about 0.07, about 0.08, about 0.09, about 0.1, about 0.2, about 0.3, or higher. In some embodiments, the stable particles described herein can exhibit second harmonic in response to an incident pressure wave, for example, at MI of no more than about 0.4, no more than about 0.3, no more than about 0.2, no more than about 0.1, no more than about 0.09, no more than about 0.08, no more than about 0.07 or lower. In some embodiments, the stable particles described herein can exhibit second harmonic in response to an incident pressure wave at a pressure of about 200-250 kPa or about 210-220 kPa.

In some embodiments, the stable particles described herein (e.g., stable particles having a shell surrounding a gas core, wherein the shell comprises nanoparticle aggregates, and the shell is porous) can be used as theranostic particles. At least one or more active agents (e.g., but not limited to drugs or therapeutic agents) can be loaded into the shell of the stable particles, e.g., during fabrication process. Additionally or alternatively, the stable particles described herein can be used as contrast agent for imaging below the MI/pressure threshold that causes cavitation. Raising MI at specific location can cavitate the stable particles, thus allowing both drug release from the shells, and also sonoporation that increase the cell permeability at targeted sites.

In some embodiments, the particles described herein can be used as intravascular oxygen delivery carriers. In some embodiments, the particles described herein can be used as blood substitute.

B. Non-Medical Uses of Gas-Filled Particles

In some embodiments, the gas-filled stable particles described herein can be used as fuel additives, e.g., gas in oil emulsions. For example, oxygen filled particles could be used to enhance the oxygen tension and oxygen content of fossil fuels, and improve the efficiency of combustion processes. This may enhance fuel economy, and be used to make any such process more efficient, powerful and/or cost-effective. See, e.g., U.S. Pat. No. 4,138,281, the content of which is incorporated herein by reference. In some embodiments, stable particles filled with fuel such as heavy fuel oil (e.g., diesel) can be formed, e.g., to improve fuel performance, and/or to reduce contaminants such as NOx and SOx. These fuel-filled particles can absorb water molecules that are smaller than the oil particles.

In some embodiments, gas-filled stable particles described herein can be used as additives in cosmetics and personal care formulations for viscosity enhancer, color modulation, gas carriers, etc. For example, gas-filled stable particles can be used added to a cosmetic composition to modulate its refractive index when applied to skin. See, e.g., WO 2000/051553 and WO2014/098294, the contents of each of which are incorporated herein by reference.

In some embodiments, gas-filled stable particles described herein can be used as additives in food products and beverages, e.g., to improve anti-spattering effects in frying food products, and/or to improve texture and/or effervescence and/or stability of food products or beverages. In some embodiments, the gas-filled stable particles can be coated with an agent, e.g., protein. See, e.g., WO 2002/060283, the content of which is incorporated herein by reference.

In some embodiments, the stable particles filled with oxygen and/or ozone gas can be used as antimicrobials or pesticides, e.g., for plants and crops as described in WO 2007/007969, the content of which is incorporated herein by reference.

In some embodiments, ozone-filled stable particles described herein can be used to remove pesticide residues, e.g., from food produces. For example, pesticide (e.g., fenitrothion)-treated vegetables can be immersed in water comprising ozone-filled stable particles to remove the pesticides. See, e.g., Ikeura et al. "Removal of residual pesticides in vegetables using ozone microbubbles" *Journal of Hazardous Materials* (2011) 186: 956-959.

In some embodiments, the gas-filled stable particles described herein can be used to facilitate water treatment and/or bioremediation. For example, ozone-filled stable particles described herein can be used to facilitate removal of oil or pollutant droplets from water by adding the ozone-filled stable particles such that oil or pollutants is/are converted into a form that can be retained by a mechanical filtration such as sand filtration. See, e.g., Cha et al. "Removal of oil and oil sheen from produced water by pressure-assisted ozonation and sand filtration," *Chemosphere* (2010) 78: 583-590.

In some embodiments, the gas-filled stable particles described herein can be used to form acoustical barriers or soundproofing materials. The acoustical barriers comprising the gas-filled stable particles can be used, e.g., in mufflers and headphones. See, e.g., U.S. Pat. No. 5,658,656, the contents of which are incorporated herein by reference.

In some embodiments, the gas-filled stable particles described herein can be embedded in hydrogels or tissue scaffolds, for example, as biocompatible porogens to facilitate creation of a porous hydrogel or tissue scaffold, or as gas carriers to facilitate gas transport within the hydrogel or tissue scaffold. See, e.g., Lima et al. "Microbubbles as biocompatible porogens for hydrogel scaffolds" *Acta Biomater.* (2012) 8: 4334-4341.

In some embodiments, the gas-filled stable particles described herein can be added into a bioreactors or fermentators to facilitate gas transport. In some embodiments, the gas-filled stable particles can comprise oxygen, e.g., for replenishment of dissolved oxygen in a bioreactor culture or a fermentation medium. See, e.g., U.S. Pat. No. 4,041,180, the contents of which are incorporated herein by reference. In some embodiments, the gas-filled stable particles can comprise a poorly soluble gas, e.g., for removal of excess saturated $CO_2$ in a bioreactor culture or a fermentation medium.

In some embodiments, a fluid comprising carbon dioxide-filled stable particles can be used as a flooding fluid for enhanced oil recovery. See, e.g., Telmadarreie et al. "$CO_2$ microbubbles—A potential fluid for enhanced oil recovery: Bulk and porous media studies" *Engineering* (2016) 138: 160-173.

Administration

The compositions containing particle suspensions may be administered locally or systemically, depending on the condition to be treated. The compositions are typically administered via injection. In some embodiments the compositions can be administered as continuous infusions. In some embodiments the compositions are administered intravenously, intraosseously, or intraarterially. In others, the compositions are administered directly to the tissue or organ in need of treatment. In other embodiments the particles can be administered inhalationally, topically (to the pleural or peritoneal cavity, to the skin, to a burn, to a wound, to the fascia, to the muscles, to the intestines or other organs), enterally (orally, sublingually, enterally, rectally).

In certain embodiments, the pharmaceutical composition is administered to the subject by intravenous, intraosseous, intraperitoneal, intraarterial, subcutaneous, and/or intramuscular injection or infusion. In certain embodiments, the pharmaceutical composition is administered to the subject topically, orally, enterally, sublingually, intranasally, or by inhalation. In certain embodiments, topical delivery is delivery to pleural, skin, peritoneum, or facial.

In one embodiment, the particle suspensions are stable in storage for prolonged periods of time, and may be withdrawn and directly injected without further alterations of the solution.

In another embodiment, the particles may be stored as a powder and reconstituted at the point of use with a pharmaceutical compound.

In another embodiment, the particles may be stored as a powder and applied topically to enterally as a powder or as viscous slurry.

In another embodiment, the particles may be formed just prior to administration, e.g. within seconds or minutes of injection, by a suitable device. The methods disclosed herein allow for rapid production of oxygen-containing particles for use in clinical settings or in the field.

The volume of the gas-filled particle suspension to be administered is a function of a number of factors including, the method of administration, the gas percentage of the particle suspension, and the age, sex, weight, oxygen or carbon dioxide tension, blood pressure, systemic venous return, pulmonary vascular resistance, and physical condition of the patient to be treated.

The whole body oxygen consumption of an 70 kg adult at rest is approximately 200 mL oxygen per minute. Thus, oxygen can be delivered at a rate of about 200 mL oxygen per minute or higher or lower depending on the demand of oxygen in a subject in need thereof. One of skill in the art can determine the corresponding infusion rate of the particle suspensions or compositions as described herein to provide the necessary amount of oxygen. Since most of the suspension contains oxygen gas, most of the volume decreases following administration and release of the gas. Additionally, when used in the setting of an acute resuscitation or in organ-targeted oxygen delivery, volumes of co-infusate may be much lower, For example, a 10 mL bolus of 50% (volume gas/volume suspension) particles in adults may provide a suitable amount of oxygen to improve the survival of the organ.

In another example, to administer 200 mL/min of oxygen gas, an emulsion containing 70 volume % gas at 10 ATM would be infused at 28.5 mL/min to deliver 8.5 mL/min of aqueous phase and 20 mL/min of gas phase at 10 ATM, or 200 mL/min of aqueous phase. For the same emulsion at 70 vol % and 20 ATM, the volume of the aqueous phase to be infused would be 4.2 mL/min, which would still provide 200 mL/min of oxygen gas at STP.

The particles are preferably designed to release the gas encapsulated therein quickly following administration in vivo. Typical release times range from 0.5 seconds to 1 minute, with shorter time periods, such as from 0.5 to 30 seconds, more preferably from 0.5 to 10 seconds, being preferred for acute resuscitations and resuscitations of the heart and with longer time periods being preferred for delivery of oxygen to the brain.

In some embodiments, the particles are designed to persist in vivo until they reach hypoxic tissue, at which time they will release the encapsulated oxygen and the particle with collapse. The particle does not persist in vivo for a sufficient time to carry carbon dioxide or other gases to the lungs. The particles generally release the encapsulated gas and the gas is absorbed by hemoglobin prior to the first circulation into the pulmonary vasculature. In a healthy adult subject with a normal cardiac output, the release of the encapsulated gas typically occurs from 4 to 5 seconds following injection, or faster.

The suspension is delivered into a subject at a suitable flow rate depending upon the subject's need. For example, when the subject needs oxygen supply, a suspension containing oxygen-filled particles can be delivered to that subject at a flow rate of 10 mL/min up to 400 mL/min (e.g., 50-300 mL/min or 100-200 mL/min). The flow-rate can also be adjusted based on the subject's oxygen consumption, oxygen saturation, skin and mucous membrane color, age, sex, weight, oxygen or carbon dioxide tension, blood pressure, systemic venous return, pulmonary vascular resistance, and/or physical conditions of the patient to be treated.

Methods of Preparation

The particles of the invention may be produced using nanoprecipitation methods. It has been discovered quite surprisingly according to the invention that micro/nanosized microbubbles having polymer shells and relatively good polydispersities can be prepared using nanoprecipitation of a polymer at the air-water interface. For example, an interfacial nanoprecipitation can be performed by providing a functionalized polymer comprising a release trigger and also a combination of hydrophobic and hydrophilic functional groups at an appropriate ratio to provide desired amphiphilicity, performing an interfacial nanoprecipitation (e.g., nanoprecipitation at the air/liquid interface) on the functionalized polymer by dissolving the functionalized polymer in an organic solvent and water to create a mixture, subjecting the mixture to homogenization to generate microbubble templates, and adding water to further induce nanoprecipitation at the polymeric interface of the microbubble templates, thereby producing a cream of stable particles including the release trigger. This interfacial nanoprecipitation method allows incorporation of functional groups (e.g., chemical functional moieties) into the shell structure of microbubbles to enable temporal control of microbubble stability. This microbubble fabrication method can also allow one to manipulate and control nanostructure and/or physio-chemical properties of the microbubbles described herein, for example, without making significant changes or alterations to the polymer precursor structure. The stable particles can then be collected and loaded with a gas of interest to generate stable gas-filled particles that are stimulus-responsive. In some embodiments of the methods described herein, the homogenization step is performed in the presence of air.

In some embodiments, the stable microbubbles as described herein can be produced as follows. A polymer such as dextran (MW 40,000) can be used to make the particles of the invention by adjusting the hydrophobic/hydrophilic balance of the dextran polymer, for example, by functionalizing with acetyl (Ac) groups through an esterification reaction, e.g., using varying amount of acetic anhydride under the presence of a base (e.g., 4-dimethylaminopyridine (DMAP)). The resultant Dex-Ac may be further functionalized to form succinylated Dex-Ac (Dex-Ac-Suc), for example, by reacting Dex-Ac with succinic anhydride. Alternatively, dextran could be functionalized, for example, with trimethylsilane (Dex-SiMe3). The functionalized dextran polymers are purified, and characterized, and fabricated into particles. The functionalized dextran polymers are dissolved in an organic solvent and 1 ml of water, and subjected to homogenization at various temperatures for 2 minutes to generate the microbubbles. Water is then added to produce a cream of particles on the top, which can then be collected, for example, in fresh water. The particles size can be adjusted by varying the speed of homogenization. Upon homogenization, the air-water interface is created so that the polymers act as surfactants and diffuse to the interface in order to minimize surface tension. This leads to an enriched concentration at interface, resulting in rapid precipitation of polymers and thus forming a shell network of nanoparticle aggregates that coat the particles.

The gas-filled particles described herein can also be prepared by any conventional methods which are modified to incorporate the release trigger, including shear homogenization (see Dressaire et al., Science 320(5880):1198-1201, 2008), sonication (see Suslick et al., Philosophical Transactions of the Royal Society of London Series a-Mathematical Physical and Engineering Sciences 357(1751):335-353, 1999; Unger et al., Investigative Radiology, 33(12): 886-892, 1998; and Zhao et al., Ultrasound in Medicine and Biology, 31(9):1237-1243, 2005), extrusion (see Meure et al., AAPS PharmSciTech, 9(3):798-809, 2008), spraying (see Pancholi et al., J. Drug Target. 16(6):494-501, 2008), mixing such as double emulsions (see Kaya et al., Ultrasound in Medicine and Biology. 35(10):1748-1755, 2009), hot melt encapsulation, and drying (e.g., by spray drying, and/or lyophilization) to obtain particles for administration. See also Meure et al., AAPS PharmSciTech 9(3):798-809, 2008. The process of "spray drying" refers to a process wherein a solution is atomized to form a fine mist and dried by direct contact with hot carrier gases. Examples of spray drying methods are also included in the Examples section. In the case of crosslinking the stimuli-responsive shell and/or sheath membrane, additional steps are required for crosslinking. One preferred method of spray drying includes a 3-fluid nozzle.

For example, in one embodiment, a process for preparing gas-filled particles comprises (a) homogenizing, in the presence of air, a solution comprising one or more materials that form a stimuli-responsive shell, thereby forming hollow particles comprising a stimuli-responsive shell; and (b) filling the hollow particles of (a) with one or more gases, e.g., by passive diffusion, to form the gas-filled stable particles described herein.

Other methods for preparing gas-filled particles as described herein are also contemplated. For example, a process for preparing gas-filled particles includes at least two steps: (i) mixing one or more materials as described above in the Examples (e.g., an organic solvent, an aqueous solution, a medium comprising a viscosity enhancing agent, or mixture thereof) to form a pre-suspension, and (ii) dispersing one or more gases into the pre-suspension to form gas-filled particles via, e.g., adsorption to the gas/lipid interface of entrained gas bodies. See, e.g., U.S. Pat. No. 7,105,151. Step (ii) can be performed under high energy conditions, e.g., intense shaking, high shear homogenization, or sonication. See, e.g., US 2009/0191244 and Swanson et al., Langmuir, 26(20):15726-15729, 2010. Acoustic emulsification (i.e. sonication) may be used to agitate the precursor solution and form the particles. Sonication generates particles rapidly and reproducibly within just a few seconds. In sonication, the sonicator horn is typically placed at the suspension-gas interface. The precursor suspension is sonicated for a sufficient time period at a sufficient power to produce the particles. Particles created in this way follow a heterogeneous size distribution. The largest particles are the most buoyant and rise to the top of the suspension, while less buoyant, smaller particles remain motile in the sonicated suspension. This allows for separation based on different migration rates in a gravitational field. In certain embodiments, high energy conditions are by high shear homogenization or sonication. The steps may further comprise crosslinking or polymerization to provide the desired particle.

For example, in one aspect, provided is a method of preparing a particle encapsulating a gas, the method comprising:
(i) mixing one or more materials (e.g., polymers) that form a stimuli-responsive shell in a medium to form a pre-suspension;
(ii) forming particles comprising the stimuli-responsive shell and a hollow core surrounded by the stimuli-responsive shell, wherein the particles are formed by nanoprecipitation of the materials (e.g., polymers) at an air-liquid interface of the pre-suspension;
(iii) filling the particles of (ii) with one or more gases to form gas-filled particles comprising a stimuli-responsive shell. In some embodiments, the particles of (ii) can be filled with one or more gases by passive diffusion.

In this particular aspect, the one or more materials comprise a stabilizing agent.

In another aspect, provided is a method of preparing a particle encapsulating a gas, the method comprising:
(i) mixing one or more materials in a medium to form a pre-suspension, wherein at least one material comprises a covalent or non-covalent crosslinkable group;
(ii) dispersing one or more gases into the pre-suspension to form gas-filled particles comprising a stimuli-responsive shell; and
(iii) subjecting the gas-filled particle to polymerization or crosslinking conditions in order to provide a covalent or non-covalent crosslinked stimuli-responsive shell.

In this particular aspect, the one or more materials does not necessarily comprise a stabilizing agent.

One method for making the particles is a double emulsion method, e.g., water-oil-water. For example a stimuli-responsive polymer may be dissolved in oil which is mixed with water to form droplets. The droplets are added to water to form empty shells or membranes or honeycomb structures. Thus, in some instances the hollow particles of the invention are spherically shaped or honeycomb structures. The particle size, thickness of the stimuli-responsive shell and honeycomb or spherical nature of the particles can be adjusted by manipulating the parameters of the methods of the invention. For instance, particle size can be altered by manipulation of homogenization parameters. Thickness of the stimuli-responsive shell or membrane can be altered by adjusting viscosity, osmotic gradient and/or precipitation speed.

In certain embodiments, the method may comprise a crosslinked membrane encapsulated by a crosslinked shell, i.e., by subjecting the gas-filled particle to polymerization or covalent or non-covalent crosslinking conditions in order to provide a covalent or non-covalent crosslinked stimuli-responsive shell, and then contacting this gas-filled particle with another material, which upon subjecting the mixture to polymerization or covalent or non-covalent crosslinking conditions, encapsulates the membrane as a covalent or non-covalent crosslinked membrane. Alternatively, the shell is crosslinked, but not the membrane. Alternatively, the membrane is crosslinked, but not the shell.

The particles thus produced, suspended in the medium used in step (i), can be concentrated, dried (e.g., lyophilized, spray dried), and/or subjected to size selection by methods known in the art, such as differential centrifugation as described in US 2009/0191244 to produce dried particles or highly concentrated suspensions of particles. Dried particles, stored as a powder, may be a way to achieve longer shelf life, and can be reconstituted by addition of a medium, such as an organic solvent, an aqueous solution, a medium comprising a viscosity enhancing agent, or mixture thereof.

In certain embodiments, the gas of the particle is replaced with another gas, e.g., by applying a stream of the desired gas to, or pulling a vacuum on, the particle to remove the encapsulated gas, then filling the hollow particle with the desired gas.

As understood from the present disclosure, the particles may be also prepared in a medium (e.g., an aqueous medium) comprising one or more viscosity enhancing agents. The inventors contemplate preparing particles in such a medium stabilizes the particle by decreasing the particle size and/or by preventing the particle from interacting with neighboring particles.

Particles and suspensions may be further be stored under inert conditions (e.g., under a blanket of argon) or under a blanket of another gas as describe herein (e.g., oxygen, carbon dioxide, carbon monoxide, nitrogen, nitric oxide, nitrous oxide, an inhalational anesthetic, hydrogen sulfide, helium, or xenon, or a mixture thereof). In certain embodiments, the particles or suspensions are stored in an oxygen-tight container, optionally under high gas pressure. Exemplary pressurization techniques for making gas filled particles under high pressure are described in U.S. Pat. No. 4,344,787, incorporated herein by reference. In certain embodiments, the gas is at 1 atmosphere, and is not pressurized. In certain embodiments, the gas is pressurized to greater than 1 atmosphere, e.g., between about 2 to about 25 atmospheres. In certain embodiments, the gas is pressurized at greater than 1 atmosphere and is delivered at an infusion rate of up to 10 ml per minute to the subject. Alternatively, in certain embodiments, the gas is not pressurized and is delivered at an infusion rate of up to 400 ml per minute to the subject.

Optionally, in another aspect, the invention relates to methods of preparing hollow particles filled with gas. The particles may be formed, for instance around a core component, to create a hollow structure, wherein the core component is removed to form a hollow particle.

Exemplary methods of making hollow particles are described in U.S. Pat. Nos. 3,528,809, 3,674,461, 3,954,678, 4,059,423, 4,111,713, 4,279,632, 4,303,431, 4,303,603, 4,303,732, 4,303,736, 4,344,787, 4,671,909, 8,361,611, 7,730,746, EP1311376, U.S. Pat. Nos. 6,720,007, 3,975,194, 4,133,854, 5,611,344, 5,837,221, 5,853,698, each of which is incorporated herein by reference. The inventors of the present invention contemplate any of the materials as heretofore described may be used to make such hollow particles, and specifically contemplate hollow particles made from PLGA.

For example, in one aspect, provided is a method of preparing a particle encapsulating a core component, the method comprising mixing one or more materials with a core component to form a pre-suspension comprising particles encapsulating the core component around a stimuli-responsive shell.

As is understood herein, the core component may be a volatile component or core. A volatile component or core refers to a material that can be removed from the dried particle to produce a hollow center, by for instance freeze drying. Exemplary volatile components include, but are not limited to, inorganics such as ammonia and its corresponding volatile salts (e.g., ammonium bicarbonate, ammonium acetate, ammonium chloride, ammonium benzoate, ammonium carbonate) and water. Exemplary non-volatile components which can also be included, are salts, buffers, acids, bases, and the like, which upon removal of the volatile component are left as a residue on or in the hollow particle.

The volatile component may further be considered a pore forming agent. Pore forming agents can be included, for example, in an amount of between 0.01% and 75% weight to volume, to increase pore formation. For example, in solvent evaporation, a pore forming agent such as a volatile salt, for example, ammonium carbonate, ammonium bicarbonate, ammonium acetate, ammonium chloride, or ammonium benzoate or other lyophilizable salt, is first dissolved in a medium such as water. The solution containing the pore forming agent is then emulsified with the solution to create droplets of the pore forming agent in the material. After the particle is formed by any of the method described herein, the suspension of particles may be spray dried or taken through a solvent evaporation/extraction process.

Solvent evaporation is described by E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984), the teachings of which are incorporated herein. In an exemplary solvent evaporation method using a pore forming agent, a material is dissolved in a volatile organic solvent such as methylene chloride. A pore forming agent as a solid or in an aqueous solution may be added to the solution. The mixture is sonicated or homogenized and the resulting dispersion or emulsion is added to an aqueous solution that contains a surface active agent such as TWEEN20, TWEEN80, PEG or poly(vinyl alcohol) and homogenized to form an emulsion. The resulting emulsion is stirred until most of the organic solvent evaporates, leaving microspheres.

Hot-melt microencapsulation is described by E. Mathiowitz, et al., Reactive Polymers., 6, 275 (1987), the teachings of which are incorporated herein. In an exemplary hot-melt microencapsulation method using a pore forming agent, the material is first melted and then mixed with the solid particles of the pore forming agent. The mixture is suspended in a non-miscible solvent (like silicon oil), and, while stirring continuously, heated to 5 C above the melting point of the material. Once the emulsion is stabilized, it is cooled until the particles solidify. The resulting particles are washed by decantation with a polymer non-solvent such as petroleum ether to give a free-flowing powder.

In an exemplary spray drying method using a pore forming agent, microparticles can be produced by spray drying by dissolving a material in an appropriate solvent, dispersing a pore forming agent into the solution, and then spray drying the solution to form particles. Using spray drying apparatus available in the art, the polymer solution may be delivered through the inlet port of the spray drier, passed through a tube within the drier and then atomized through the outlet port. The temperature may be varied depending on the gas or material used. The temperature of the inlet and outlet ports can be controlled to produce the desired products. The size of the particulates is a function of the nozzle used to spray the solution, nozzle pressure, the flow rate, the material used, the material concentration, the type of solvent and the temperature of spraying (both inlet and outlet temperature) and the molecular weight. Generally, the higher the molecular weight, the larger the capsule size, assuming the concentration is the same. Typical process parameters for spray drying are as follows: concentration of the material in the medium=0.005-0.10 g/ml, inlet temperature=30°–200° C., outlet temperature=20°–100° C., flow rate=5-200 ml/min., and nozzle diameter=0.2-4 mm ID. Particles ranging in diameter between one and ten microns can be obtained with a morphology which depends on the selection of the material, concentration, molecular weight and spray flow.

Once the particles are formed, the core component is removed, e.g., in vacuum and/or by drying, e.g., by lyophilization and/or by spray drying, to provide a hollow, dried particle. The hollow dried particle may later be reconstituted by addition of another medium, such as an organic solvent, an aqueous solution, a medium comprising a viscosity enhancing agent, or mixture thereof. The particle is then filled with a gas.

The particles may be made by a method using an aqueous core that is then freeze dried to yield the final hollow particle. For example this may be accomplished using a 3-fluid nozzle in a spray drying method. See also US 2011/022010, incorporated herein by reference, which describes spray drying using a 3-fluid nozzle.

In the particle preparation process the polymer and core component may be first mixed with each other. The mixing may involve kneading. The apparatus used for kneading may include a plastomill, a planetary mixer, a roll mill, a kneader, an extruder etc.

The resulting mixture is heated to a temperature not lower than the softening point (or melting point) of the polymer to give a thermal melt admixture which is then cooled and solidified by spraying into a refrigerant preferably at 5 to 50 C. through a multiple-fluid nozzle, for example a 1-fluid or more, preferably 2-fluid or more, more preferably 3-fluid or more nozzle, in a rotating disk atomizer, to recover the composite particles. Preferably, the admixture is sprayed together with a compressed gas into a refrigerant. The refrigerant is particularly preferably in a gaseous phase. The compressed gas used as fluid is a compressed gas or compressed nitrogen preferably at $9.8\times10^4$ Pa or more, more preferably at $9.8\times10^4$ to $29.4\times10^4$ Pa. This gas is preferably heated at a temperature not lower than the spray temperature in order to prevent the nozzle from clogging upon cooling thereby enabling continuous production of the particles.

In order to convert the sprayed particles into fine particles, the multiple-fluid (3-fluid or more) nozzle may preferably be a pencil type nozzle or a straight type nozzle, and particularly a 3-fluid pencil type nozzle and a 4-fluid straight type nozzle can be preferably used. Using the pencil type nozzle the fluid speed at a collision focal spot, and fracture force, are higher due to the condensed stream. The 3-fluid pencil type nozzle and the 4-fluid straight type nozzle, a 3-fluid pencil type nozzle and 4-fluid straight type nozzle are available commercially from Micro Mist Dryer MDL-050C manufactured by Fujisaki Electric Co., Ltd.

For example, the invention is a method of preparing a gas-filled particle comprising drying a particle comprising a core component to produce a hollow dried particle and dispersing one or more gases into the hollow dried particle to form a gas-filled particle, wherein the one or more gases is not a fluorinated gas, perfluorocarbon based liquid, or hemoglobin. In certain embodiments, the drying step is spray drying. In certain embodiments, the core component comprises ammonium carbonate. In certain embodiments, the core component comprises water. In certain embodiments, the method further comprises pressurizing the gas.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1: Exemplary Methods and Materials for Fabrication of the Particles Described Herein Material Synthesis Dextran (MW 40,000) was selected as an exemplary material to produce the particles described herein due to its excellent biocompatibility. The hydrophobic/hydrophilic balance of the dextran (Dex) polymer was adjusted, for example, by functionalizing with acetyl (Ac) groups through an esterification reaction, e.g., using varying amount of acetic anhydride under the presence of a base (e.g., 4-dimethylaminopyridine (DMAP)). Dex-Ac was further functionalized to form succinylated Dex-Ac (Dex-Ac-Suc), for example, by reacting Dex-Ac with succinic anhydride. Alternatively, dextran could be functionalized, for example, with trimethylsilane (Dex-SiMe3). The scheme is shown in FIG. 1.

The functionalized dextran polymers were purified, for example, by precipitating in a solvent such as methanol or diethyl ether, and characterized, for example, by 1H NMR to determine the degree of substitution.

Microparticle Fabrication

Functionalized dextran polymers, e.g., as described above and in FIG. 1, (100 mg) were dissolved at 100 mg in 2.2 ml of an organic solvent (e.g., DMSO) and 1 ml of water, and were subjected to homogenization at various temperatures for 2 minutes to generate microbubbles (MPs). Afterwards, 30 ml of water was added and a MPs cream formed on the top. The bottom solution was withdrawn to wash off the DMSO and the MPs were collected, for example, in fresh water. The MP size can be adjusted by varying the speed of homogenization.

In addition to DMSO, other organic solvents for dissolution of functionalized dextran polymers can be used, including, for example, but not limited to dimethylformamide (DMF), dioxane, tetrahydrofuran (THF), acetone, acetonitrile, and any combinations thereof.

Microparticle Formation Mechanism

Cryo-SEM and SEM were used to investigate the dextran based microparticles formed using the method as described above. SEM results show that the shells of MPs consisted of nanoparticle aggregates, as illustrated in FIG. 2 and FIG. 3. In particular, FIG. 3 shows that MPs made of Dex-SiMe3 contain nanoparticle aggregates on the exterior surface of the shell.

Based on the SEM results illustrated in FIG. 3, without wishing to be bound by theory, MPs can be formed by nanoprecipitation of the polymer at the air-water interface. First, polymers (e.g., functionalized dextran polymers) are soluble in a solvent/water mixture (e.g., DMSO/water mixture). Second, upon homogenization, the air-water interface is created so that the polymers act as surfactants and diffuse to the interface in order to minimize surface tension. This leads to an enriched concentration at interface, resulting in rapid precipitation of polymers and thus forming a shell network of nanoparticle aggregates that coat the MPs. The discrete nanosphere features were more apparent in Dex-MeSi3 MPs due to its higher hydrophobicity.

Example 2: Characterization of Exemplary Particles Described Herein

Gas Release Mechanism

It was observed that MPs described herein, e.g., based on Dex-Ac-Suc, exhibited pH responsiveness. For example, when they were transferred from water into a physiological solution (e.g., with a pH=7.4) such as plasmaLyte, the gas cores of the MPs rapidly filled with fluid and released gas into the surroundings. The nanoparticle aggregates formed on the exterior surface of the MP shells were held together by hydrophobic interactions and hydrogen-bonding between COOH and other groups when the MPs were kept in water. Without wishing to be bound by theory, when the MPs were added from water into a solution with a different pH (e.g., plasmaLyte), deprotonation of COOH triggered by pH change would destabilize the MP shells to deform or disintegrate thereby releasing gas.

The deformability and degradability of shells are considered highly desirable for oxygen delivery application because a large number of MPs can cause potential blockage in blood vessels. In this Example, two Dex-Ac-Suc with different degree of substitution (DS) of succinyl (Suc) groups, 0.1 (low) and 0.3 (high), were investigated. In videos and time-lapse (not shown), it was found that the MPs made of Dex-Ac-Suc with high DS (e.g., DS=0.3) almost instantly dissolute in plasmaLyte with shells disintegrating quickly. The MPs made of Dex-Ac-Suc with low DS (e.g., DS=0.1) were quickly filled with fluid and while the shells did not disappear quickly, they deformed under stirring. Thus, these findings show that DS of Suc groups allows changing shell properties, e.g., its deformability and/or degradability.

Microparticle Stability

Figure 4:
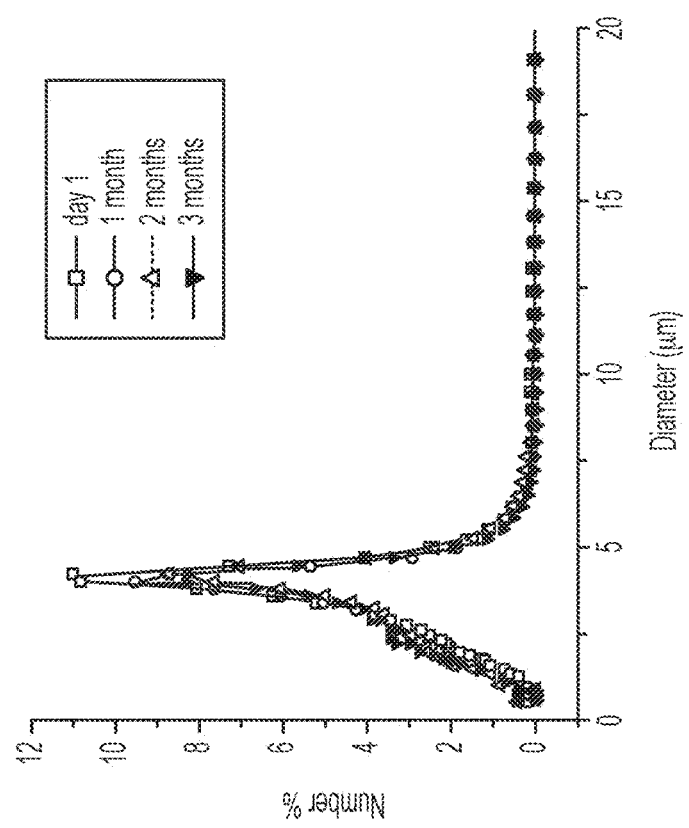
FIG. 4 shows the stability of the Dex-Ac-Suc (low DS) microbubbles over time.

The particles described herein, e.g., Dex-Ac-Suc MPs, are shown to be stable for at least three months or longer (e.g., at least one year or longer) at room temperature with little decrease in foam height, and little change in size as shown in FIG. 4, indicating that no Ostwald ripening and coalescence took place for polymeric shelled MPs.

Upon activation of a release trigger (e.g., pH change), 40% foam or the particles described herein in a 4 mL infusion lasted ~5 min before they were 100% dissolved.

Oxygen Delivery In Vitro

Figure 5:
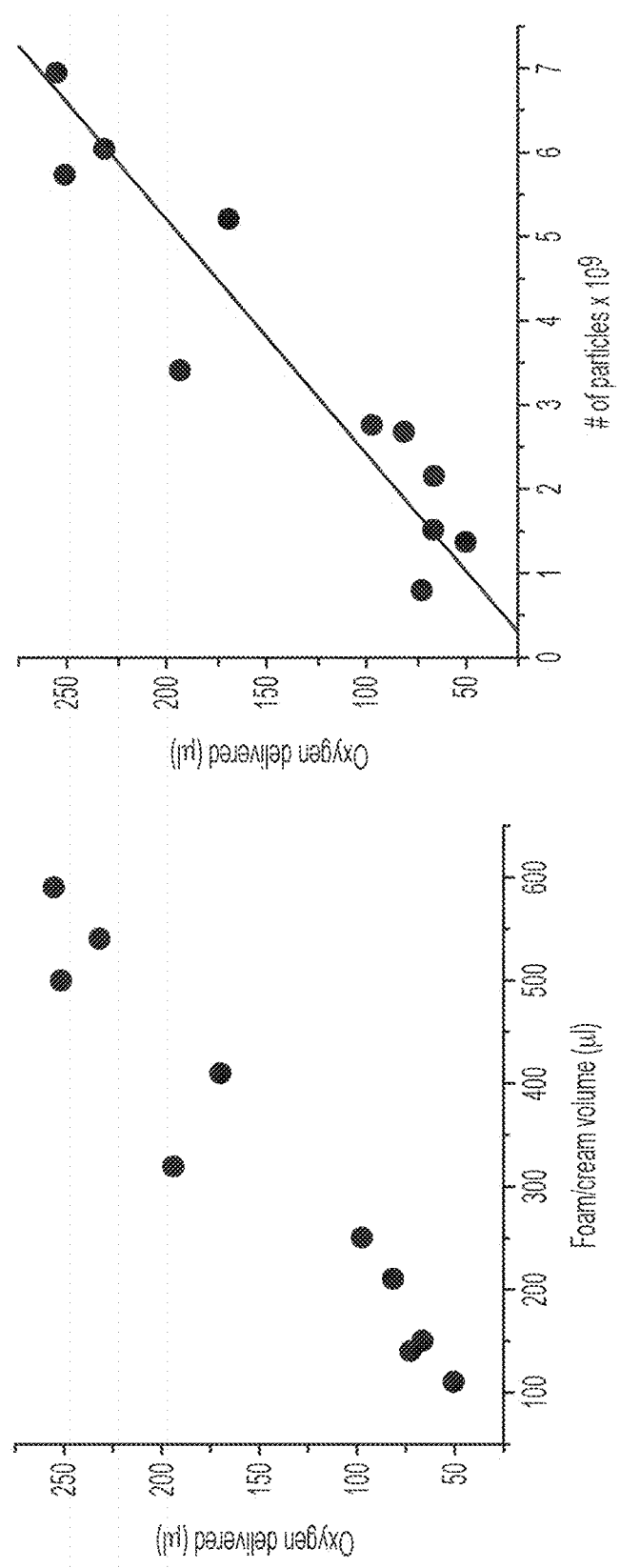
FIG. 5 shows graphs of the oxygenation of human blood by Dex-Ac-Suc based microbubbles. The left image is quantified based on foam/cream volume. The right image is quantified based on the number of particles.
Figure 6:
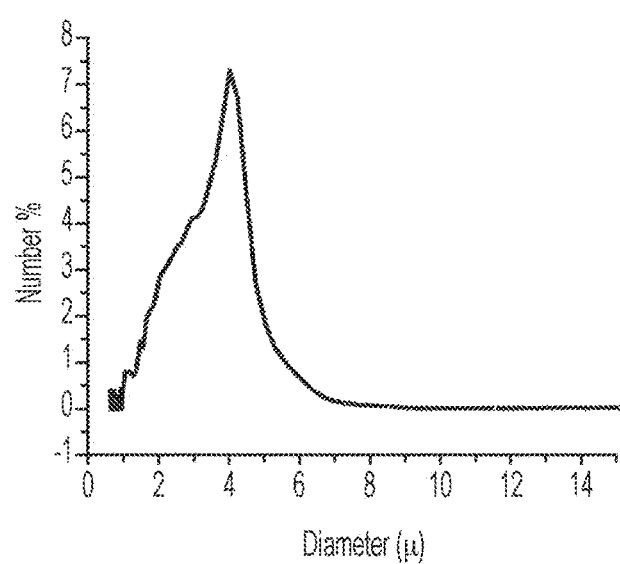
FIG. 6 shows size distribution of Dex-Ac-Suc microbubbles for oxygenation. The speed of homogenization to form the microbubbles is 15 k rpm.
Figure 7:
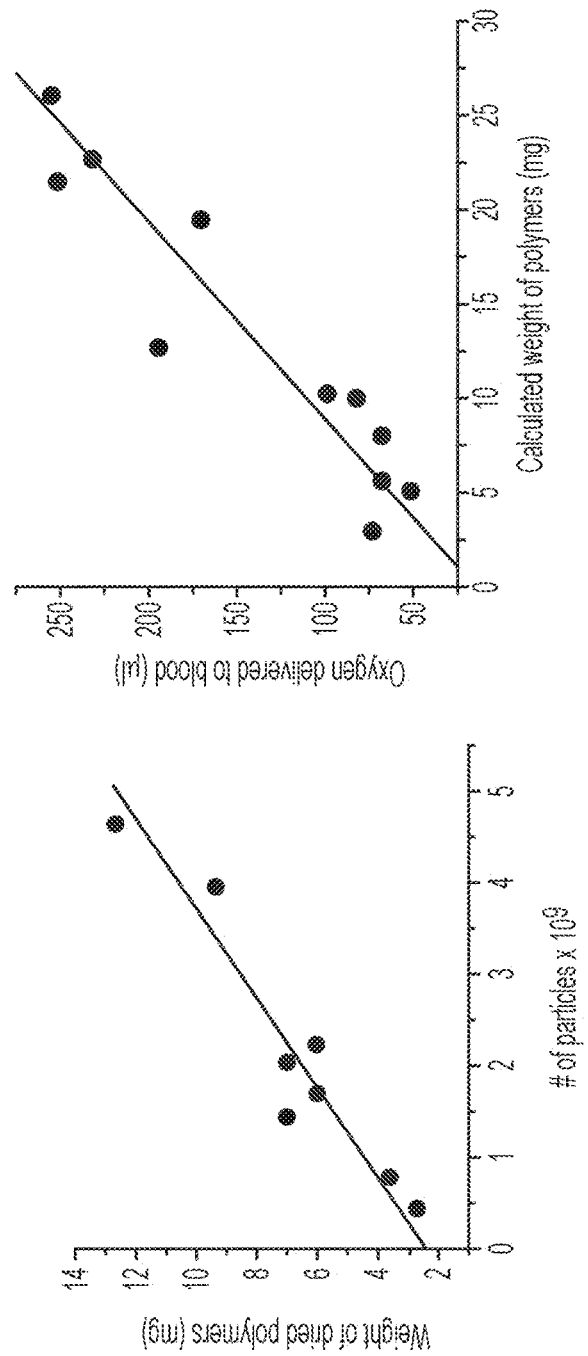
FIG. 7 shows graphs of the weight of Dex-Ac-Suc microbubbles related to number of particles (left image) and volume of oxygen delivered (right image).

It was discovered that Dextran-based MPs, when suspended in water, are gas permeable. This allows the MPs to be back filled with one or more biological gases, e.g., oxygen, by purging the head space of foam. By way of example only, Dex-Ac-Suc (low DS) MPs in 5% dextrose solution were purged with oxygen to investigate their gas carrying capacity for human blood, and the results are shown in FIG. 5. The size distribution was shown in FIG. 6. In addition, weight of polymers were measured in terms of number of particles, and the relation between polymer weight and gas carrying capacity was shown in FIG. 7. The results show that 1 mg of Dex-Ac-Suc (low DS) MPs delivers about 10 µl of oxygen. The gas carrying capacity of the MPs described herein can be varied, e.g., by making MPs of larger size.

Preliminary In Vivo Safety Study

Figure 8:
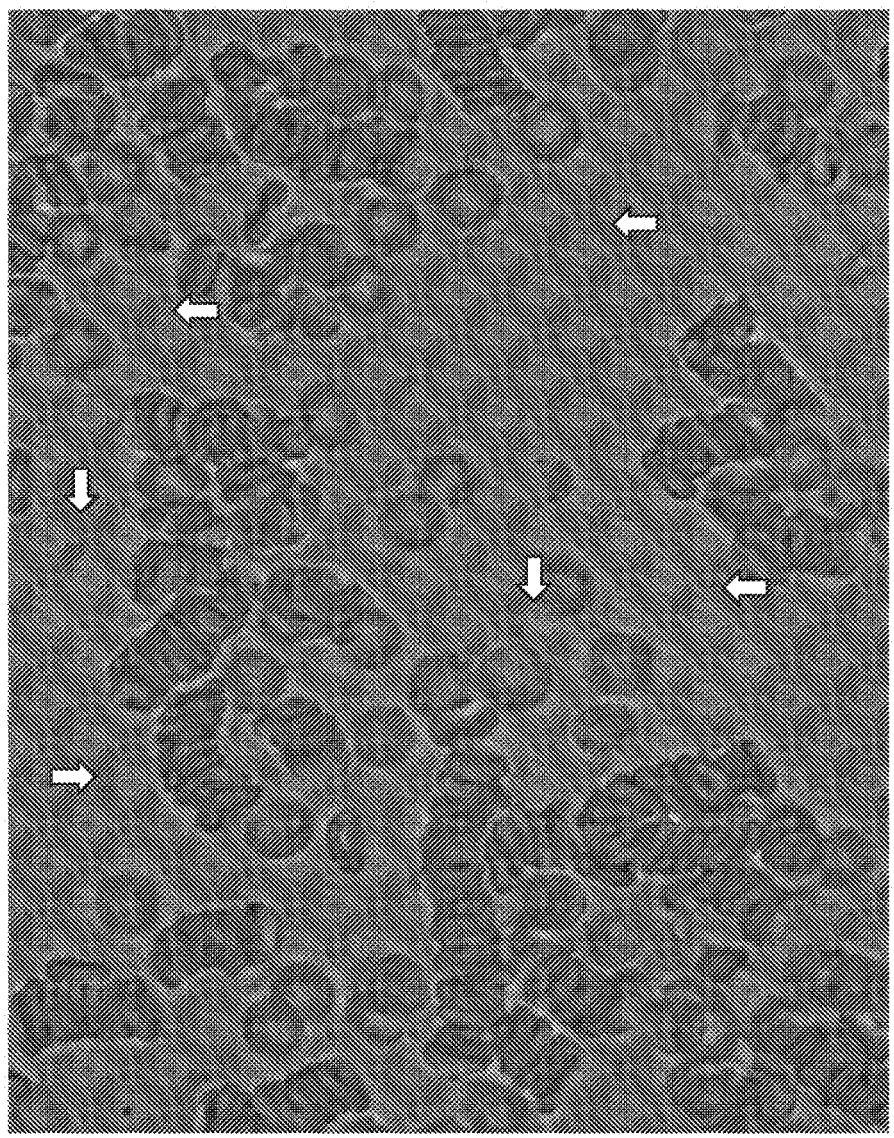
FIG. 8 shows arrows pointing to the collapsed MP shells in rat blood after microparticle injection.
Figure 9:
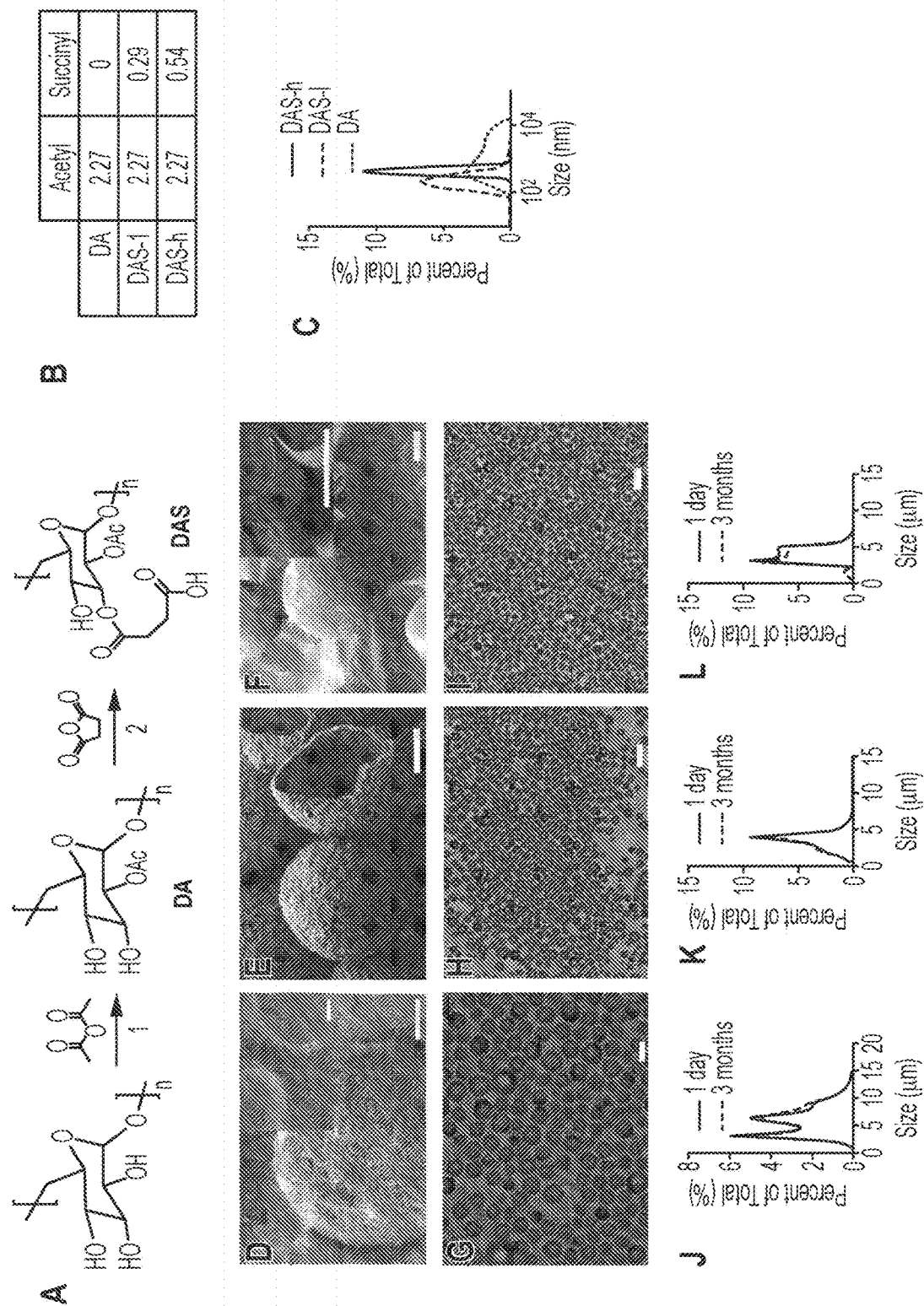
FIG. 9 shows an exemplary design strategy of stable particles according to some embodiments described herein. Panel A shows a synthetic scheme for modification of Dextrans. Panel B shows the degree of substitution of modified dextrans. Panel C shows the dynamic light scattering of 75% DMSO/water solution of DA, DAS-1 and DAS-h. Panel D shows cryo-SEM of DA MBs. Panel E shows cryo-SEM of DAS-1 MBs. Panel F shows cryo-SEM of DAS-h MBs (Scale=1 µm). Panel G shows a microscopic image of DA MBs. Panel H shows a microscopic image of DAS-1 MBs. Panel I shows a microscopic image of DAS-h MBs (Scale=10 µm). Panels J-L show the size distribution of MBs fabricated under 15 k rpm. Panel J shows DA MBs, Panel K shows DAS-1 MBs, and Panel L shows DAS-h MBs.

Dex-Ac-Suc (low DS) MPs (filled with air) were injected into rats breathing 20% oxygen (n=4). Five consecutive injections that were spaced 2 mins apart were injected into each rat within 30 seconds. They all survived the injection. The highest dosage of MPs injected was $3.5 \times 10^{10}$ particles, as in 80 v/v % foam in 5 ml (10% dextrose) solution. Each injection delivered approximately 2 mL of gas. Similar to the observations made in the in vitro blood oxygenation experiment, the MPs quickly hydrated upon mixing with blood under low mechanical force, i.e. stirring or low pressure, and the shells disintegrated or deformed. A blood sample from the rat after injection was shown in FIG. 8. Sub-micro size particles resulting from the collapse of MPs were observed under microscope.

Example 3: Gas-Based Functional Materials by Interfacial Nanoprecipitation

Summary

Cardiac arrest (e.g., complete cessation of blood flow) is the most lethal medical condition and resuscitation requires immediate restoration of oxygen delivery to the myocardium. Intravenous injection (i.v.) of oxygen carrying microcarriers is an emerging strategy for rapid myocardial oxygen delivery; however, existing microcarriers are unstable and cause vascular obstructions making them unsuitable for clinical use. Described in this Example are ultra-stable and pH-triggered self-eliminating microbubbles (MBs) as oxygen carriers, which are produced based on a phenomenon of nanoprecipitation of amphiphilic biopolymers at air/liquid interface. These MBs are stable for months, and rapidly dissolve when infused into blood. Repeated i.v. infusions were safe and hemodynamically well tolerated in rodents. When added to a standard resuscitation algorithm in an asphyxial cardiac arrest model, MBs comprising dextrans with acetyl and succinate moieties (DAS) increased survival from 0% to 100%.

Introduction

Cardiac arrest is a disorder in which complete cessation of heart function leads to immediate termination of blood flow, and systemic oxygen delivery. The key pathology in cardiac arrest is that tissue hypoxia ensues immediately and causes diffuse end-organ injury within minutes. Recent studies suggest that clinical outcomes are significantly higher during uninterrupted CPR (1, 2); and that restoring oxygen delivery to the myocardium using extracorporeal membrane oxygenation (ECMO) improves the likelihood of return of spontaneous circulation (ROSC) as well as neurologically intact survival (3-5). However, ECMO is a limited resource, takes time to implement, and has intrinsic risks. As a result, cardiac arrest has a mortality rate of approximately 90% in the ~600,000 people who suffer from this disease annually in US alone (6), and survivors frequently suffer from neurocognitive disability (7). The ability to increase oxygen delivery to the brain and myocardium via an injectable therapeutic would avoid interruptions in CPR, maximize arterial oxygen content, dilate the pulmonary vasculature and constrict the systemic vasculature, all of which would improve myocardial oxygen delivery and survival from cardiac arrest.

Figure 20:
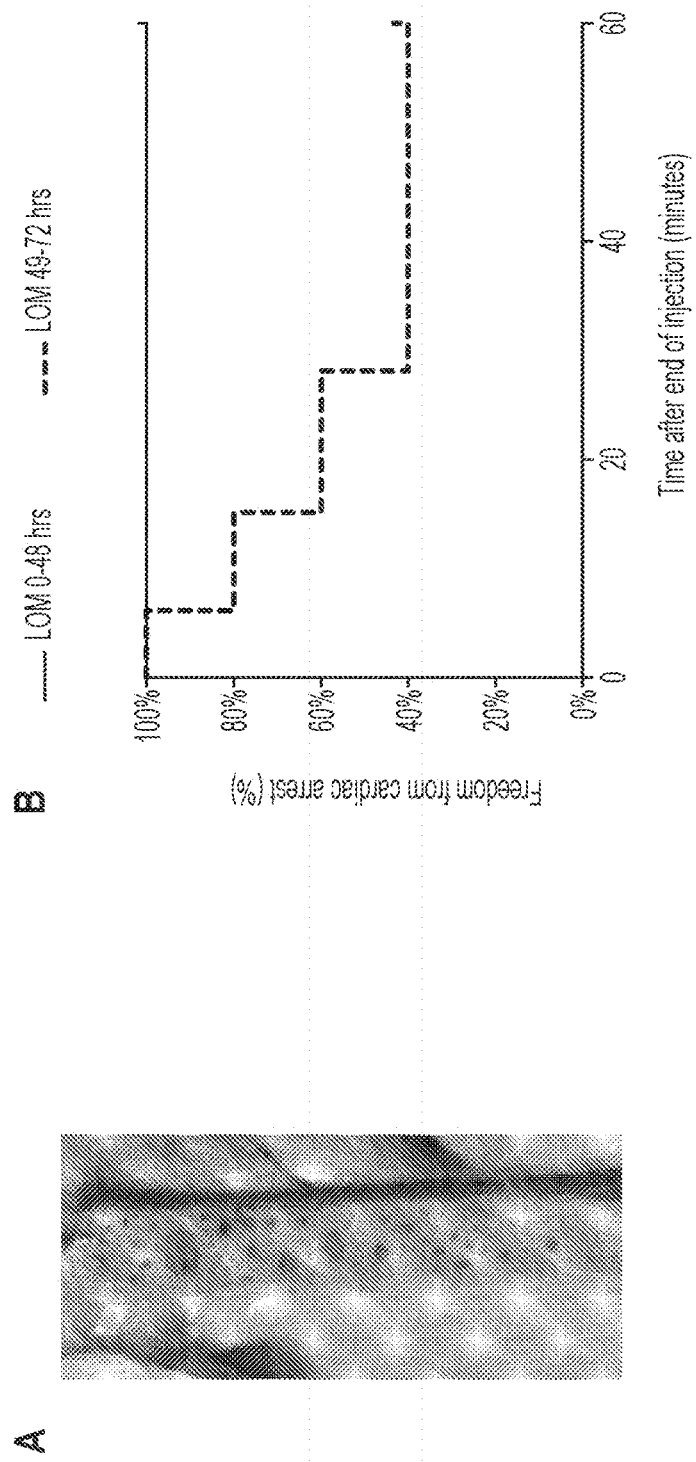
FIG. 20 shows that lipid-based oxygen carriers cause lethal embolism following rapid infusion. Panel A shows rapid infusion of lipidic oxygen microbubbles into the femoral vein of Yorkshire pigs (35 kg) following cardiac arrest resulted in the formation of large free gas bubbles and increased incidence of death from pulmonary obstruction (n=8 LOMs; n=8 controls). Panel B shows a Ka-plan-Meier plot illustrating the incidence of cardiac arrest following infusion of freshly prepared or aged lipidic oxygen microbubbles into the femoral vein of Sprague Dawley rats (Panel B, LOMs, solid curve (n=5); dotted curve (n=5)). Panels C-D show optical micrographs of freshly prepared (Panel C) or aged (Panel D) LOMs reveal the evolution of lipid debris within LOM suspension during storage at 4° C.
Figure 20:
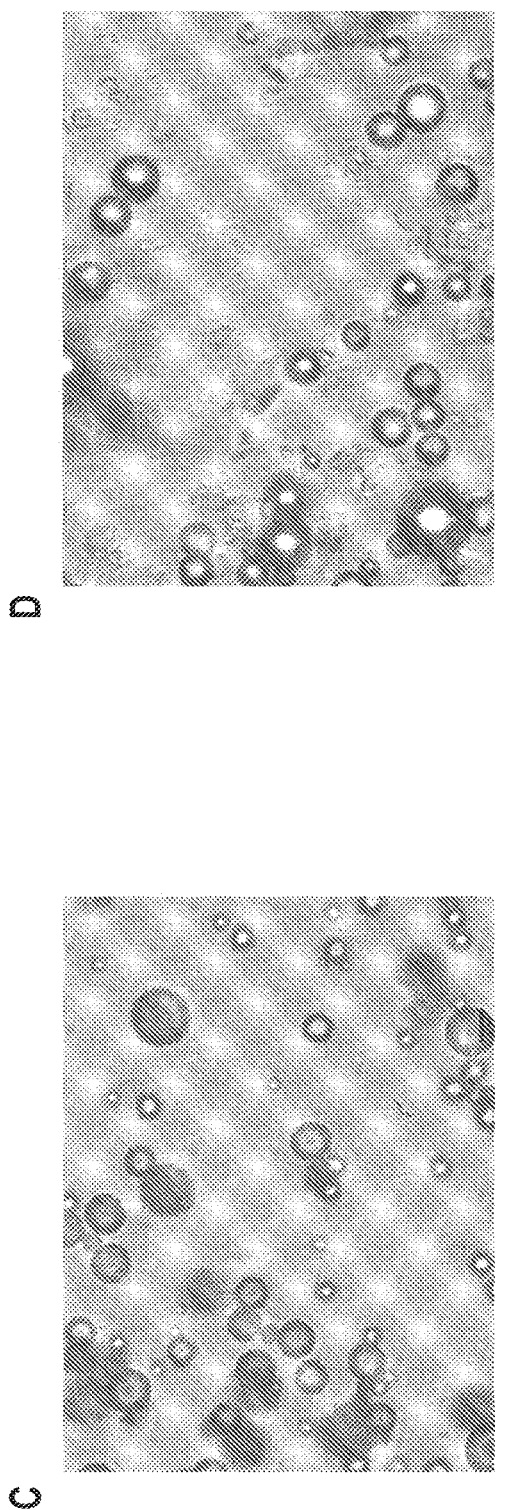
Figure 21:
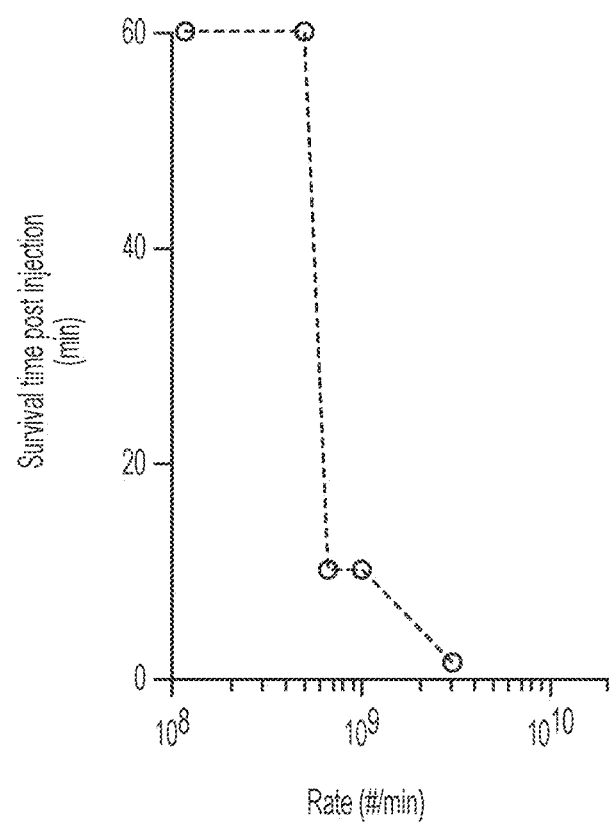
FIG. 21 shows that polymer-based hollow microparticles are lethal at high doses. Infusion of air-filled poly(D,L-lactic-co-glycolic) acid-based PHMs acid cause pulmonary obstruction when infused into rodents at rates greater than $4 \times 10^8$ particles per minute. Animals received a single bolus injection over 5 minutes and were survived for 1-hour.

The most direct route to rapidly introduce oxygen gas into the bloodstream is direct injection through a peripheral catheter (IVO2 therapy). However, i.v. injection of free gas is lethal and requires the use of artificial gas microcarriers, such as lipidic microbubbles, polymer microcapsules, hemoglobin derivatives, and perfluorocarbon-based emulsions (8-14). Microcarriers intended for use in cardiac arrest are desirable to rapidly deliver sufficient volumes of oxygen without causing vascular obstruction; and be strictly size-limited to that of the capillaries (~8 μm), both during prolonged storage and following intravenous injection. These requirements preclude the use of hemoglobin- and perfluorocarbon (PFC)-based carriers because the volume load required to rapidly administer sufficient volumes of oxygen to the bloodstream is prohibitive. Oxygen-loaded and PFC-filled polymer microcapsules are also of limited utility as i.v. infusion of concentrated suspensions caused microvascular obstructions, resulting in tissue damage and death (10, 15-17). Lipidic oxygen microbubbles (LOMs), while the most successful IVO2 drug to date (8), lack the in vivo dissolution behavior and storage stability needed for use in cardiac arrest. For example, it is reported that continuous i.v. infusion of LOMs at controlled rates prevented the onset of cardiac arrest in animals undergoing prolonged asphyxia by tracheal occlusion; however, rapid injection in animals, following ventricular fibrillation-induced cardiac arrest, led to microvascular obstruction and increased mortality (FIG. 20, panels A-D). Furthermore, freshly prepared LOMs were required, as their long-term storage has not yet been realized.

It is contemplated that a desirable gas carrier for cardiac arrest is a microbubble with a responsive solid nano-shell that preserves particle size distributions during long-term storage, but undergoes rapid self-elimination in response to a physiologic trigger. The existence of such a material can permit the prolonged administration of clinically meaningful volumes of oxygen without the risk of vascular obstruction. The latter is imperative in the context of its use, e.g., in cardiac arrest, as the circulation is significantly compromised and even minor microvascular obstructions would be poorly tolerated. This Example describes the synthesis and characterization of ultra-stable polymer microbubbles (MBs) with pH-triggered self-eliminating property, produced based on a unique phenomenon of nanoprecipitation at air/liquid interfaces. The in vivo safety profile, and the ability to facilitate ROSC following asphyxial cardiac arrest of the MBs are demonstrated in this Example.

Microbubble Fabrication

Figure 16:
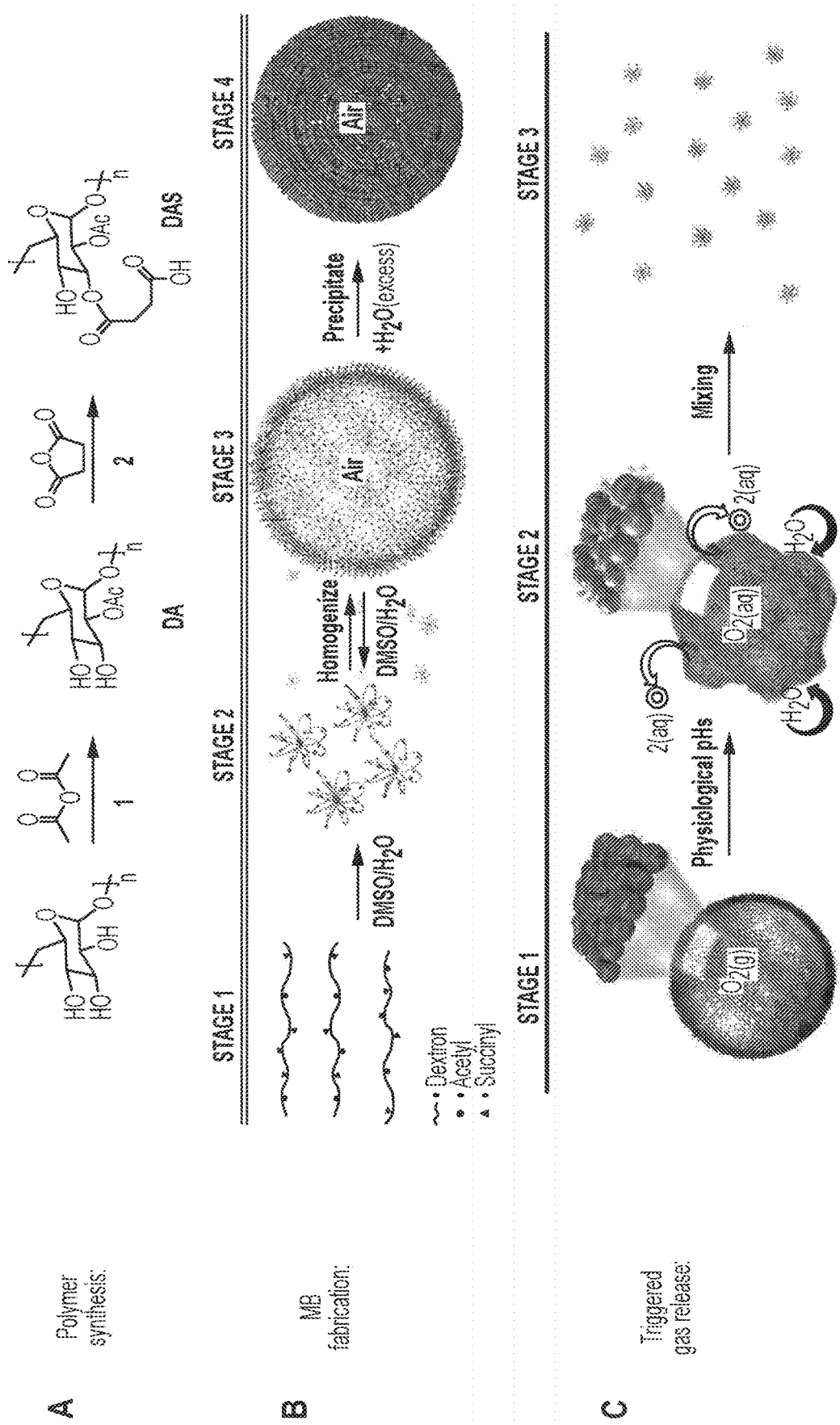
FIG. 16 shows the synthesis of stable dextran-based microbubbles (MBs) with pH-responsive shells for intravenous oxygen delivery. Panel A shows the reaction scheme for the synthesis of amphiphilic and pH-responsive dextran polymers (DAS). Panel B shows that the fabrication of DAS MBs is facilitated via interfacial nanoprecipitation at the air-water interface following high shear homogenization. Panel C shows that exposure of DAS MBs to physiological pH causes rapid hydration of the microbubble, solubilization of the oxygen gas core, and dissolution of the MB shell.

Existing methods to stabilize gas bubbles or control shell properties (e.g., pH-triggered elimination) are lacking (18, 19). Nanoprecipitation is a physical phenomenon that produces polymeric nanostructures through solvent exchange (20). It was hypothesized that prolonged microbubble stability could be achieved by inducing nanoprecipitation at the air/liquid interface (FIG. 16, panels A-C). This approach may provide a facile way to manipulate MB shell morphology and chemo-physical properties by varying polymer designs. To test this hypothesis, biodegradable dextrans were chemically modified with acetyl (DA) and succinate (DAS) moieties with varying degrees of substitution (acetyl:succinyl ratio: DA (2.27:0); DAS-1 (2.27:0.29); DAS-h (2.27:0.54), FIG. 16, panel A; FIGS. 26-29). The acetyl groups renders the polymers amphiphilic; while the succinyl moieties impart the pH responsiveness needed to dissolve the shell under physiological conditions (FIG. 16, panel A). The present derivatives, like other acylated dextrans (21), are not water soluble but form nanoparticle aggregates via nanoprecipitation. These nanoaggregates cannot be directly dispersed to stabilize MBs.

To directly induce nanoprecipitation at the air/liquid (a/l) interface of freshly generated MBs, a co-solvent system was designed. First, modified dextrans (DA, DAS-1 or DAS-h) were solubilized using a DMSO/H$_2$O mixture (75:25) (FIG. 16, panel B, Stage 1) in which they exist as large micellar clusters (FIG. 17, panels A-C and FIG. 16, panel B, Stage 2). Second, this DMSO/water solution was homogenized in the presence air, which generated a transiently stable foam (MBs) (FIG. 16, panel B, Stage 3); the majority of foam at this stage disappeared hours after homogenization, indicating that DAS micelles may behave like surfactants due to their amphiphilic nature (e.g., reversibly assembling at the all interface and temporarily stabilize the MB template). Third, an excess of water was added to the foam as a non-solvent, which further induced nanoprecipitation at the polymeric interface of the MB templates (FIG. 16, panel B, Stage 4). As DMSO rapidly diffuses into the bulk water phase away from the polymer-rich interface, the DAS micelles precipitate as interconnected nanoparticles to form solid-like polymer shells around the gas core. Cryo-SEM characterization of the MBs demonstrates that the shells are composed of polymer nanoaggregates (primary particle <50 nm), indicating that nanoprecipitation took place at the all interface (FIG. 17, panels D-I).

Figure 17:
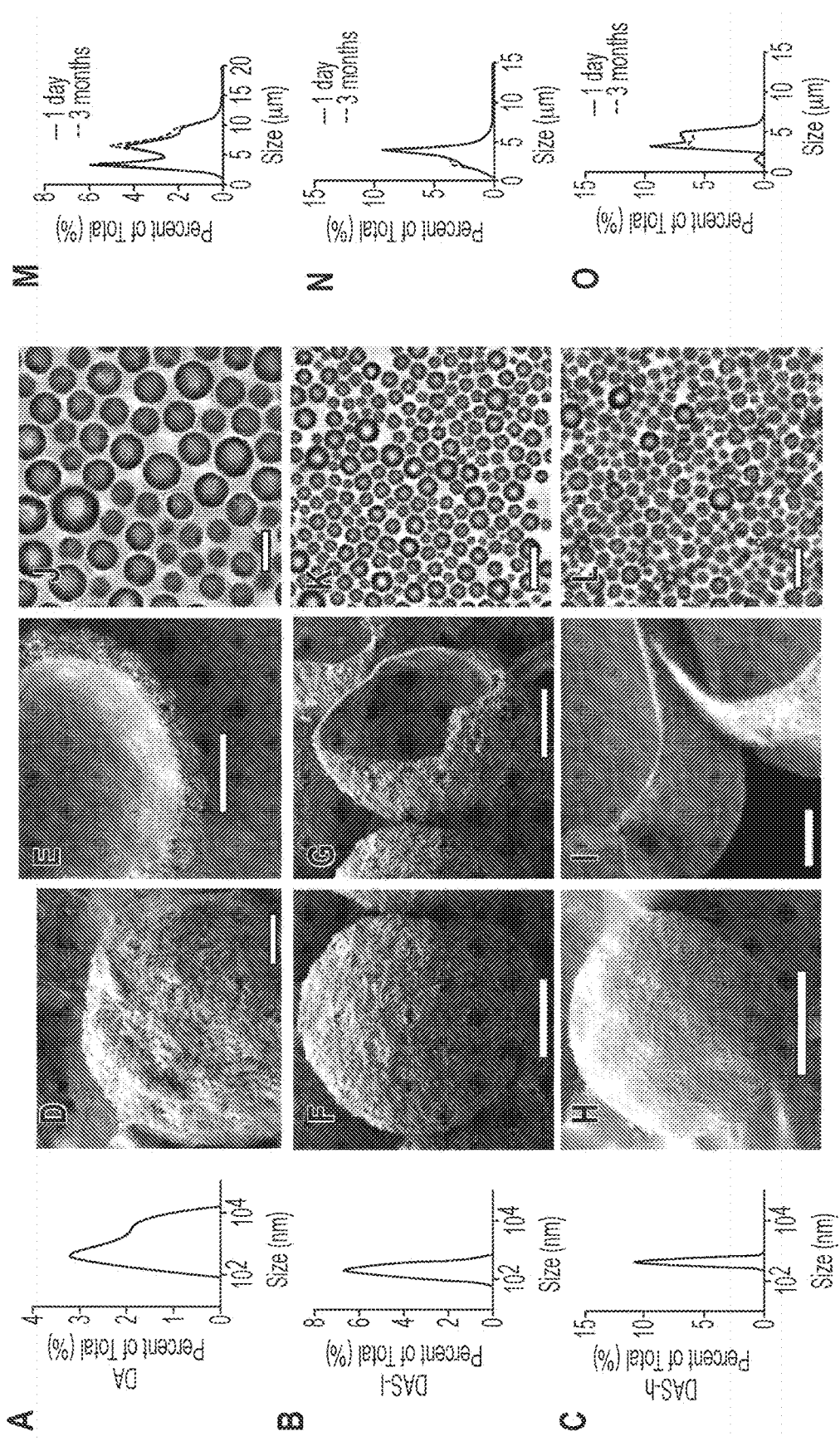
FIG. 17 shows the fabrication of stable microbubbles using interfacial nanoprecipitation of dextran-based derivatives. Panels A-C show dynamic light scattering of DA (Panel A), DAS-1 (Panel B), and DAS-h (Panel C) dissolved in DMSO/water mixture (75:25). Panels D-I show cryo-scanning electron micrographs (cryo-SEM) of the topography and shell structures for MBs fabrication from DA (Panels D and E), DAS-1 (Panels F and G), and DAS-h (Panels H and I) polymers. Panels J-L show optical photomicrographs of DA MBs (Panel J), DAS-1 MBs (Panel K), and DAS-h MBs (Panel L) immediately following fabrication. Panels M-O show size distribution and stability profile of DA MBs (Panel M), DAS-1 MBs (Panel N), and DAS-h MBs (Panel O) fabricated via high shear homogenization at 15 k rpm. Scale bars: 1 μm (Panels D-I); 10 μm (Panels J-L).

Varying the polymer structure afforded control over MB morphology (FIG. 17, panels D-E). For example, the large DA micelles in DMSO/H2O (FIG. 17, panels A-C) resulted in MBs with thick shells (~300 nm), composed of the large primary nanoparticles (~50 nm). In contrast, the succinylation in DAS-1 and DAS-h decreased the hydrophobic interaction in DMSO/$H_2O$, yielded smaller micelles, which eventually led MBs with thinner (20-40 nm) and smoother surface, a desirable feature that increases gas carrying capacity. Using homogenization speeds of 15,000 RPM, DAS-1 and DAS-h MBs had mean diameters 3.39±2.82 μm and 3.61±1.58 μm, respectively (FIG. 2, panels M-O). DAS MBs were stored in 10% dextrose solution (D10) at room temperature. The solid shells of dextran MBs effectively eliminated coalescence and ripening, such that no changes in size distribution or total number of particles were observed after 3 months (FIG. 17, panels J-O).

pH Responsiveness, Rheology, Gas Carrying Capacity, and Blood Compatibility.

Figure 10:
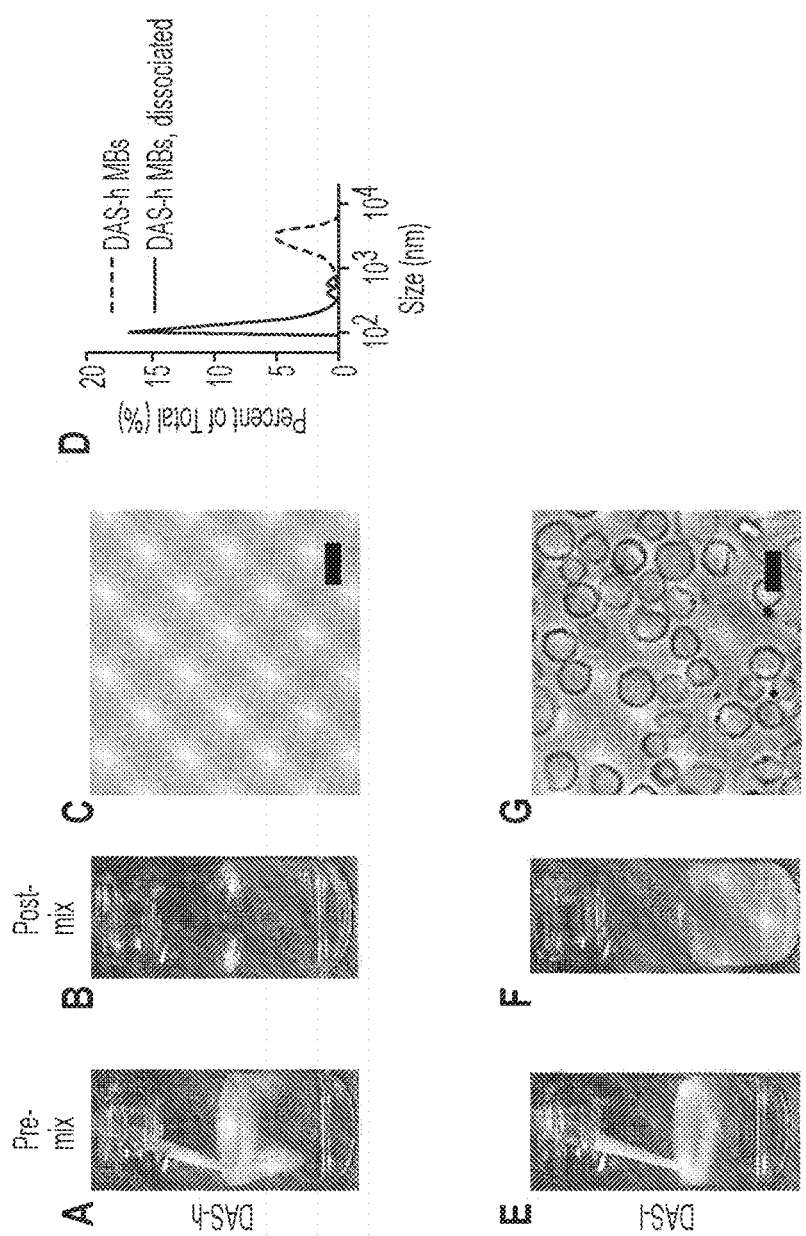
FIG. 10 shows that dextran-based MBs dissolve at physiological pHs and have similar viscosities as blood. Panels A-C show that the addition of DAS-h MBs to a solution of Plasma-Lyte A (pH 7.4, Panel A) results in rapid dissolution of the MB shells (Panel B). There were no visible MBs or particle debris by optical microscopy (Panel C). Panel D shows that dynamic light scattering experiments indicate that dissolution of the DAS-h MB shells results in the formation of soluble nanoparticles. Panels E-G show that in contrast, the addition of DAS-1 MBs to a solution Plasma-Lyte A (pH 7.4, Panel E) produced a cloudy solution (Panel F) that showed water-filled core-shell particles with swollen shells (Panel G). Panel H shows the dissolution kinetics of DAS-h MBs are rapid at physiological pHs. Panels I and J show shear rate viscosity (Panel I) and infinite shear viscosity ($n_\infty$, Panel J) profiles for DAS-h MBs at various concentrations. Scale bars: 5 µm. Error bars represent the standard error of the mean. $P<0.01$, *$P<0.001$, ****$P<0.0001$.
Figure 10:
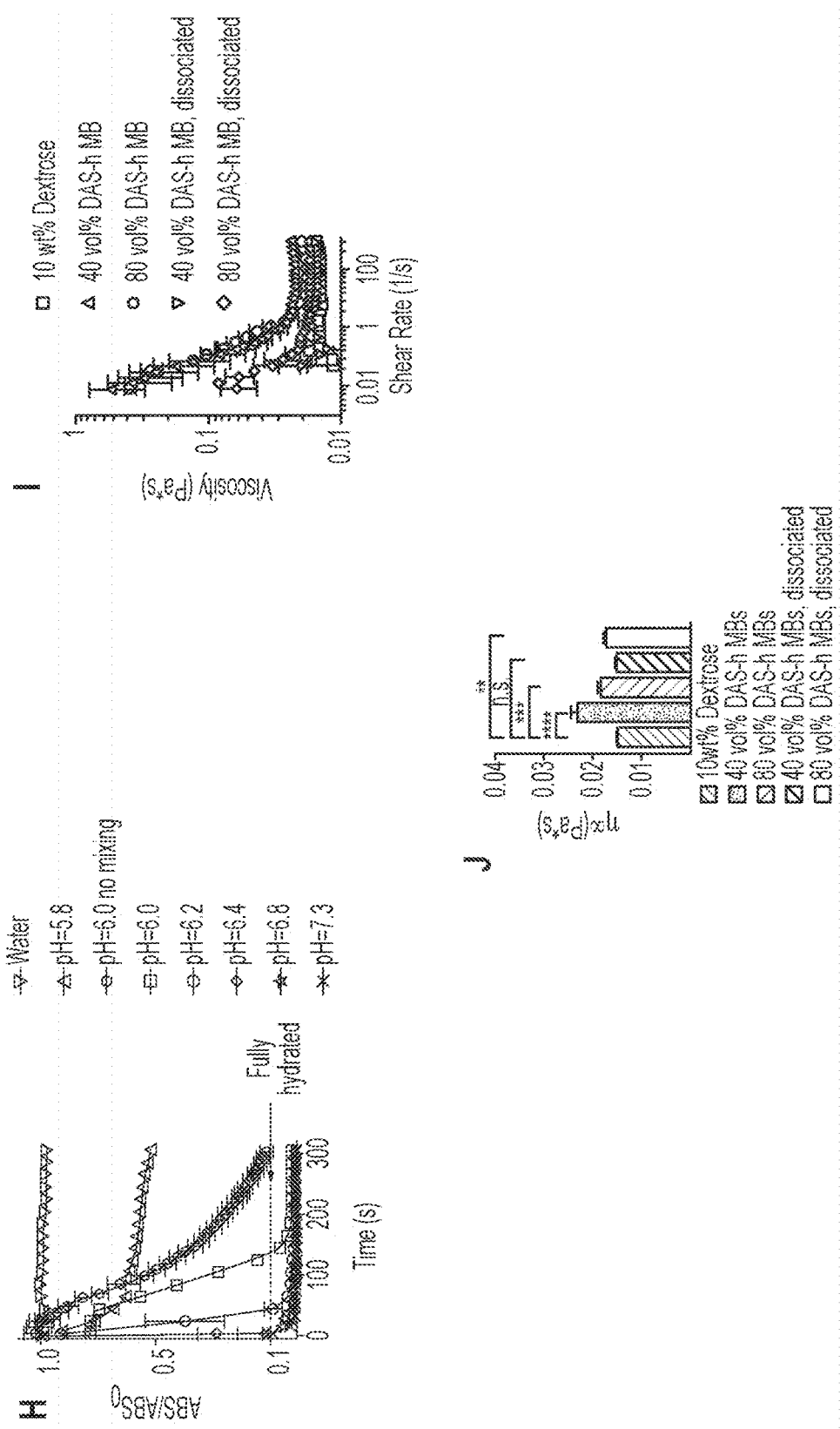

The pH-triggered self-eliminating behavior of the DAS-1 and DAS-h MBs, e.g., for potential IVO2 application was next investigated. Many pH-triggered drug deliveries rely on deprotonation of carboxyl groups (pKa=4~5) (22), which increases charge densities and effects sudden changes in solubility. When DAS-1 and DAS-h MBs were stored in D10, the carboxyl groups predominately existed in protonated form throughout the shells, including those exposed to water on the outer surface (FIG. 16, panel C, Stage 1). When added into Plasma-Lyte A (pH 7.4), DAS-h MBs instantly disappeared upon shaking, producing a clear solution in which neither solid shell debris or gas bubbles were observable (FIG. 10, panels A-C; FIG. 16, panel C, Stages 2 and 3). Further inspection revealed that the microcarrier shell dissociated into soluble nanoparticles (diameter ~100 nm by DLS, FIG. 10, panel D). In contrast, addition of DAS-1 MBs to Plasma-Lyte A produced a cloudy solution that did not disappear with mixing. Microscopic analysis revealed that the presence of fluid-filled microcapsules with intact solid shells (FIG. 10, panels E-G). Water immediately penetrated the microcarrier shell, regardless of the polymer used, to dissolved the gas cores, likely because deprotonation of surface carboxyls increases shell permeability. Note that the water influx forces gas dissolution into the liquid phase, which subsequently diffuses into the surroundings as dissolved gas ($Gas_{(aq)}$) rather than free gas bubbles, a feature which greatly enhances the safety of DAS MBs as gas carriers. Because DAS-h MBs are more heavily carboxylated and exhibit thinner shells than DAS-1 MBs, deprotonation results in the complete self-elimination. Since the pH of arterial and venous blood may be as low as 6.5 in acute illness, the ability of DAS-h MBs to degrade and release gas over a broader range of pH environments using standard turbidity assays was assessed. DAS-h MBs exhibited complete and rapid dissolution over a range of physiological pHs (pH 6.0 to 7.3; FIG. 10, panel H). Given their favorable dissolution kinetics, size distribution, and shell thickness, DAS-h MBs were further investigated for their efficacy as a gas-carrying agent.

The shear-rate viscosity profile of DAS-h MB suspensions before and after pH-triggered self-elimination was studied (FIG. 10, panel I). Foam suspensions were shear thinning at low shear rates with a yield rate $\gamma<0.01$ s$^{-1}$ and a high shear plateau at $\gamma>2$ s$^{-1}$. The high shear rate viscosity of the MB suspensions was comparable to D10 and was similar to reported values for blood (FIG. 10, panel J) (8). Dissolution of the MB shell led to a decrease in the yielding behavior of the solution, with a high shear plateau observed at $\gamma>0.1$ s$^{-1}$. The high shear rate viscosity of the dissolved MB suspensions was of comparable values as the original foam suspensions. This viscosity behavior suggests that MB suspensions will not have adverse rheologic effects on blood flow.

Figure 11:
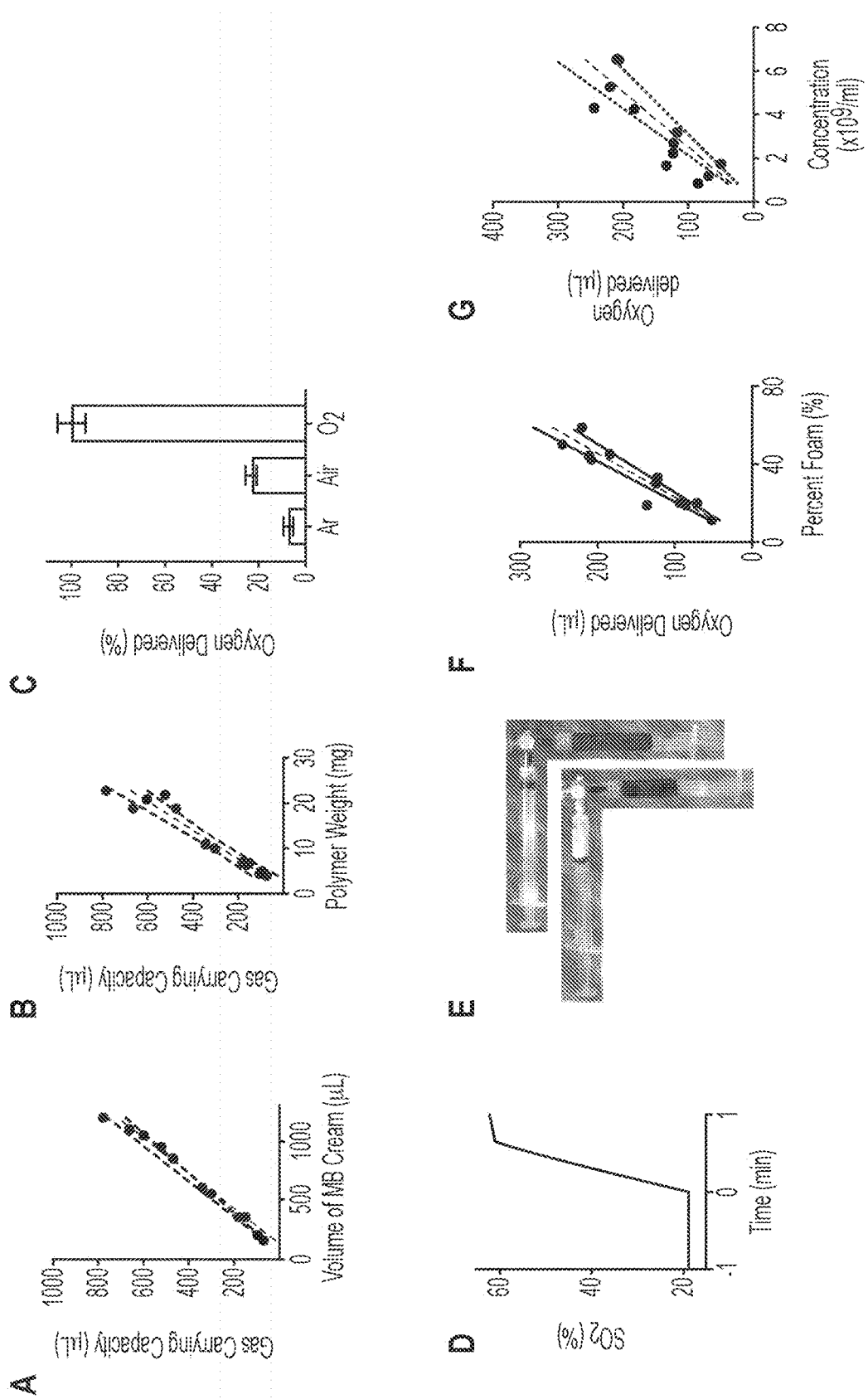
FIG. 11 shows that DAS-h MBs have high gas carrying capacities, are oxygen permeable, and rapidly deliver their gas payloads to desaturated blood. Panels A and B show the gas fraction of DAS-h MB foams (i.e. cream layer) was estimated to be 63% of the cream layer (i.e. slope=0.63±0.02, $R^2$=0.9875, Panel A), which equates to 31.4±2.59 µL $O_2$/mg polymer ($R^2$=0.9305, Panel B). Panel C shows that DAS-h MB foams (10 vol % in D10) are gas permeable. Panels D and E show that gas release from oxygen-loaded DAS-h MBs is instantaneous. Oxygen release kinetics was monitored spectrophotometrically (Panel D) and visually confirmed by the reddening of the blood from a deep maroon (deoxygenated) to a bright red (oxygenated, Panel E). Panel F shows oxygen delivery increased linearly with the increasing concentrations of DAS-h MB foams. Panel G shows oxygen delivered to human blood by mixing 1 mL of $O_2$ loaded DAS-h MBs at various concentrations in terms of number of particles, linear regression 39.6±3.16. Error bars represent standard error of the mean. Panels A, B, and F show fits from linear regression analysis with 95% confidence intervals.
Figure 15:
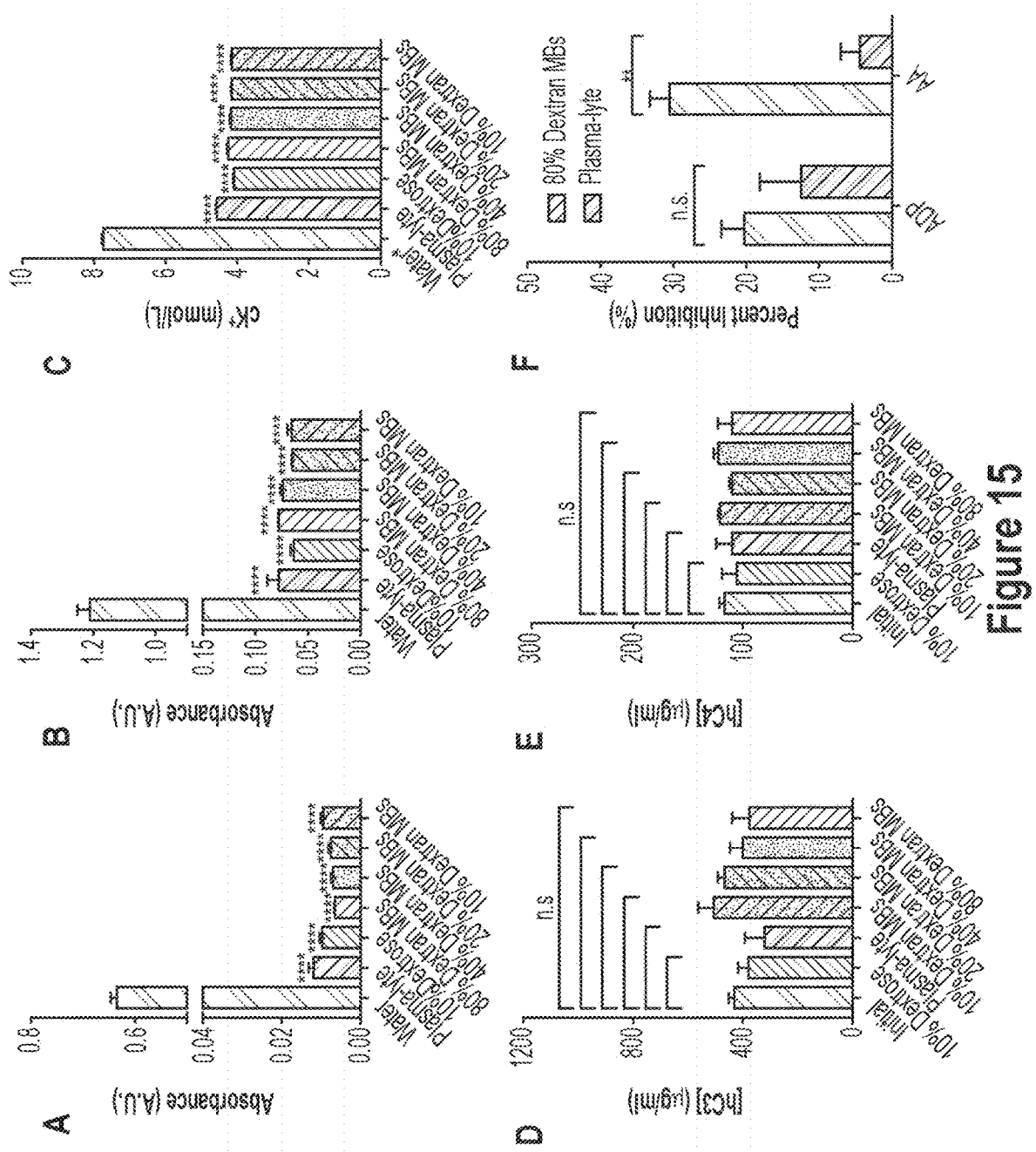
FIG. 15 shows experimental data of exemplary stable particles in ex vivo blood hemolysis assays. Panel A shows blood serum turbidity after incubating MBs with freshly isolated hRBCs for 90 minutes at 37° C. Panel B shows serum lactate dehydrogenase activity after incubating MBs with freshly isolated human red blood cells (hRBCs) for 90 minutes at 37° C. Panel C shows potassium concentrations after incubating MBs with freshly isolated hRBCs for 90 minutes at 37° C. Error bars represent the standard error of the mean. **** P<0.0001. Panels D-E show complement activity. Freshly isolated human serum was tested for activation of human complement following treatment with Air-DAS-h MBs. C3 (Panel D) and C4 (Panel E) complement concentrations after incubating with freshly isolated human serum with dextrose (10 wt %), Plasma-Lyte A, or Air-DAS-h (10, 20, 40, and 80 vol %) at 37° C. for 90 minutes. Panel F shows percent inhibition of platelet function due to the addition of MBs to whole blood for both arachidonic acid (AA) and adenosine diphosphate (ADP) pathways. Error bars represent the standard error of the mean.
Figure 22:
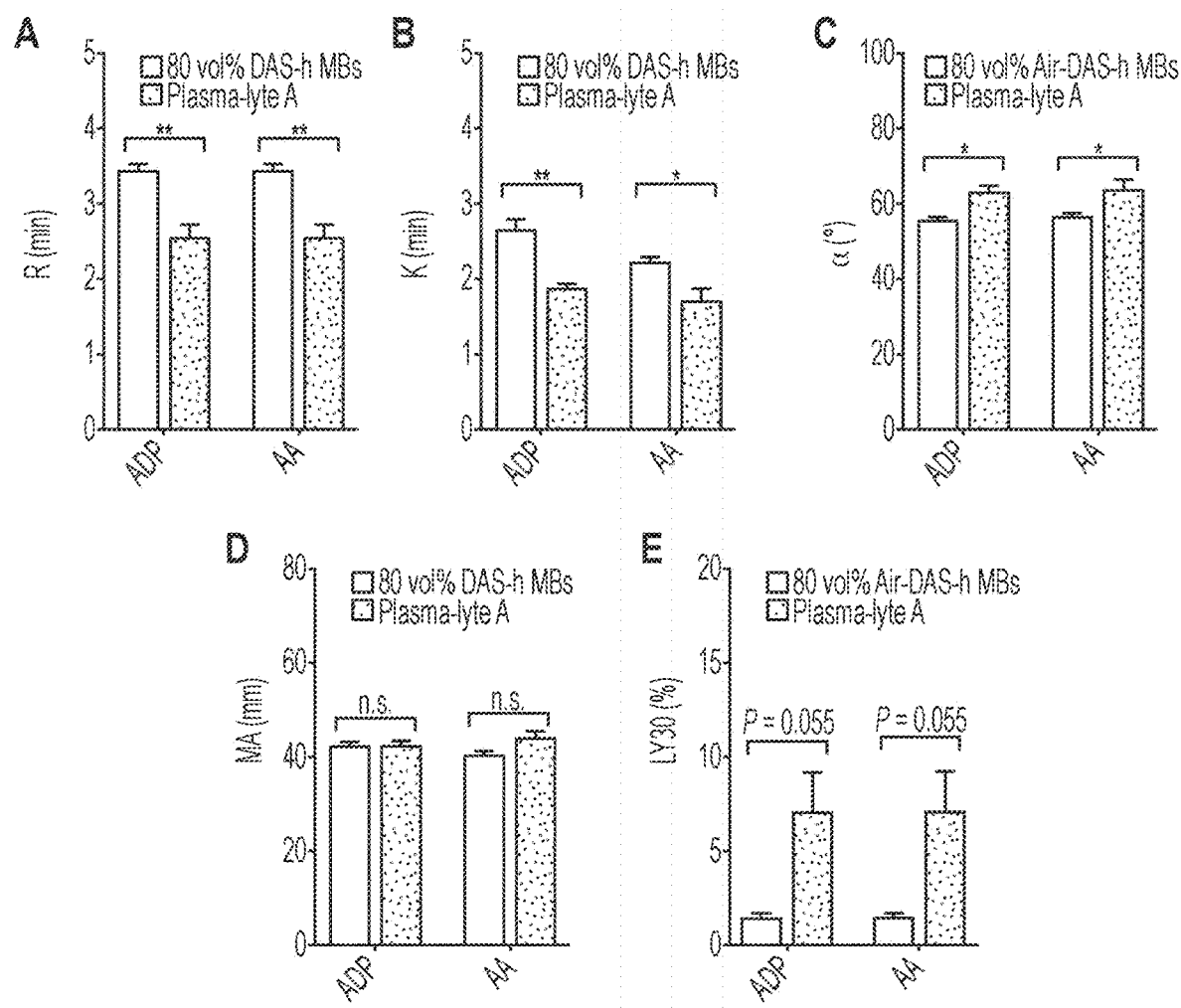
FIG. 22 shows the results of thromboelastography. Panels A and B show that treatment with DAS-h MBs slightly decreases the time for initial clot formation (Panel A, ADP: mean difference=0.9, P<0.05; AA: mean difference=0.9, P<0.05) and clot amplification (Panel B, ADP: mean difference=0.76, P<0.05; AA: mean difference=0.53, P<0.05), relative to controls. Panel C shows that DAS-h MBs slightly decreased clot propagation relative to controls (ADP: mean difference=−7.74, P<0.05; AA: mean difference=−7.07, P<0.05). Panel D shows that DAS-h MBs did not affect clot maximum amplitude (i.e. maximal clot strength, P>0.05). Panel E shows that DAS-h MBs improved clot stability 30 minutes post-MA (ADP: MD=−5.7, P=0.055; AA: MD=−5.7, P=0.055). All values were within normal ranges: R=4-8 minutes; K=0-4 minutes, MA=54-72 min, Alpha angle=47-74°, Lys30=0-8%. Error bars represent the standard error of the mean. * P<0.05, P<0.01, *P<0.001, ****P<0.0001.

The gas carrying capacity of DAS-h MBs was estimated by weight to be ~63% (v/v) (FIG. 11, panel A) or ~31 mL $O_2$/g of polymer (FIG. 11, panel B), which is ~182× greater than oxygen carrying capacity of hemoglobin (0.17 mL/g), on a per gram basis (10). To show that that the MB shells were permeable to gas, DAS-h MBs were manufactured as above (in air) and passively loaded with oxygen or argon gas under slight positive pressure for 48 hours. Air-, argon-, and oxygen-loaded DAS-h MBs were subsequently added to desaturated human blood, the change in oxygen saturation was recorded, and the volume of oxygen released was quantified. Oxygen-loaded DAS-h MBs contained 5× the oxygen of air-loaded MBs, and argon-purged particles released negligible volumes (FIG. 11, panel C). These results show that DAS-h MBs are highly permeable to multiple gases and that loading is nearly quantitative. Finally, oxygen delivery occurred within seconds under sink conditions (FIG. 11, panels D-E) and exhibited a linear dose-response relationship (FIG. 11, panel F), thus demonstrating the ability to control the volume of gas delivered. Furthermore, the biocompatibility of DAS-h MBs were assessed using human blood and serum. They were not hemolytic (FIG. 15, panels A-C) and did not cause activation of human complement (FIG. 15, panels D-E). Their effect on coagulation was within normal range (FIG. 22, panels A-E).

Acute Hemodynamic Effects Following i.v. Injection of Gas-Loaded DAS-h MBs

Figure 12:
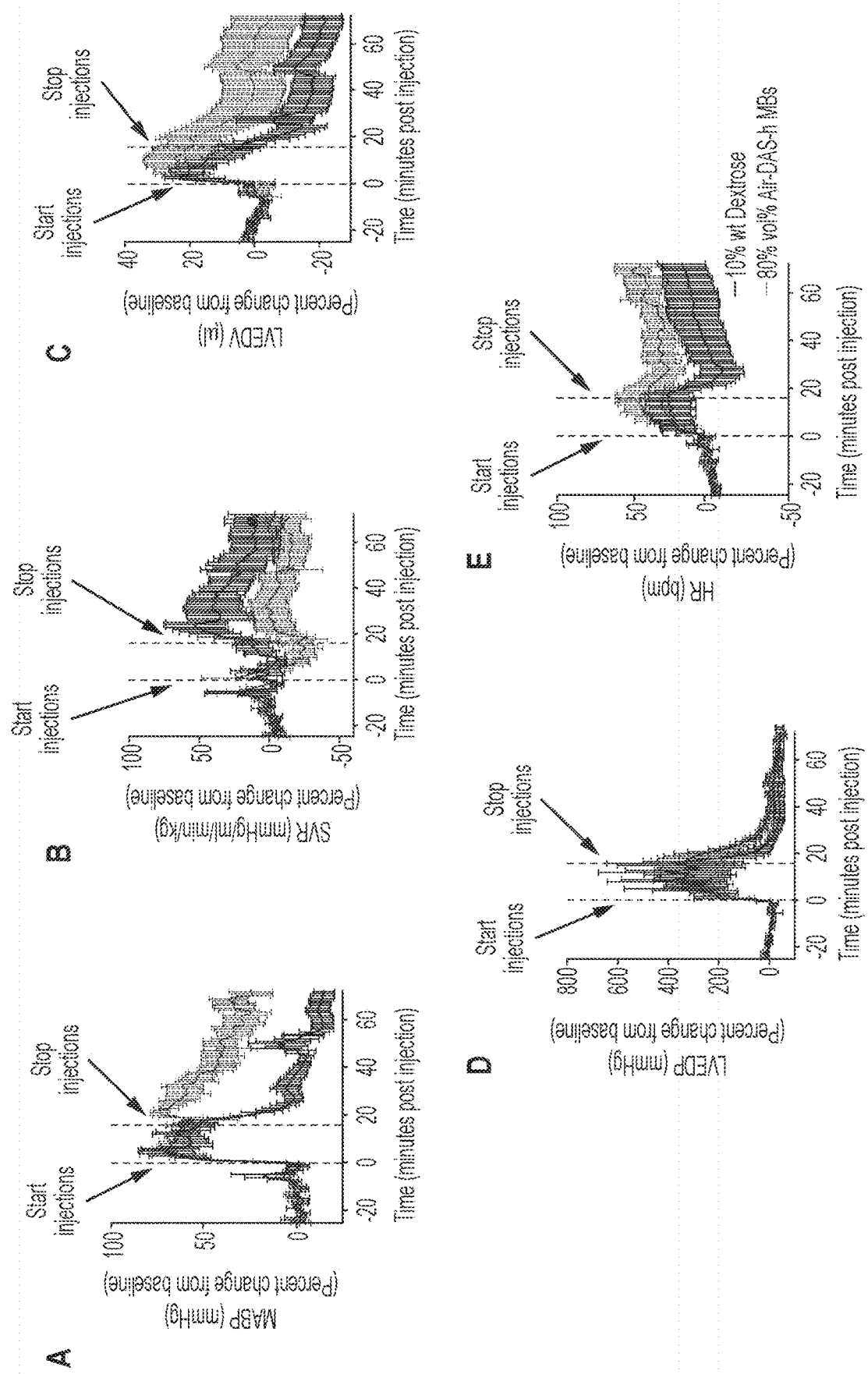
FIG. 12 shows hemodynamic data following i.v. infusion of 80 vol % Air-DAS-h MBs. Panel A shows that the mean arterial blood pressure (MABP) increased during injections, relative to controls, and remained elevated during the 1-hour observation period (mean difference=−32.−2, $P<0.0001$). Panel B shows that the systemic vascular resistance (SVR) decreased during injections, relative to controls, and remained decreased during the 1-hour observation period (mean difference=15.246, P=0.732). Panel C shows that the left ventricular end diastolic volume (LVEDV) was increased in animals receiving Air-DAS-h MBs, relative to controls (mean difference=−12.308, P=0.123). Panel D shows that the left ventricular end diastolic pressure was the same between groups (mean difference=−33.146, P=0.769). Panel E shows that animals receiving Air-DAS-h MBs had elevated heart rates (HR) compared to controls during both the injections and observation periods (mean difference=−18.671, P=0.001). Panel F shows that the $PaO_2/FiO_2$ ratio was similar between groups at baseline, 30 minutes, and 60 minutes post cardiac arrest (P>0.05). Panels G-I show other acute hemodynamic effects following intravenous injection of the stable particles (80 vol %) filled with air according to some embodiments described herein. Error bars represent the standard error of the mean.
Figure 12:
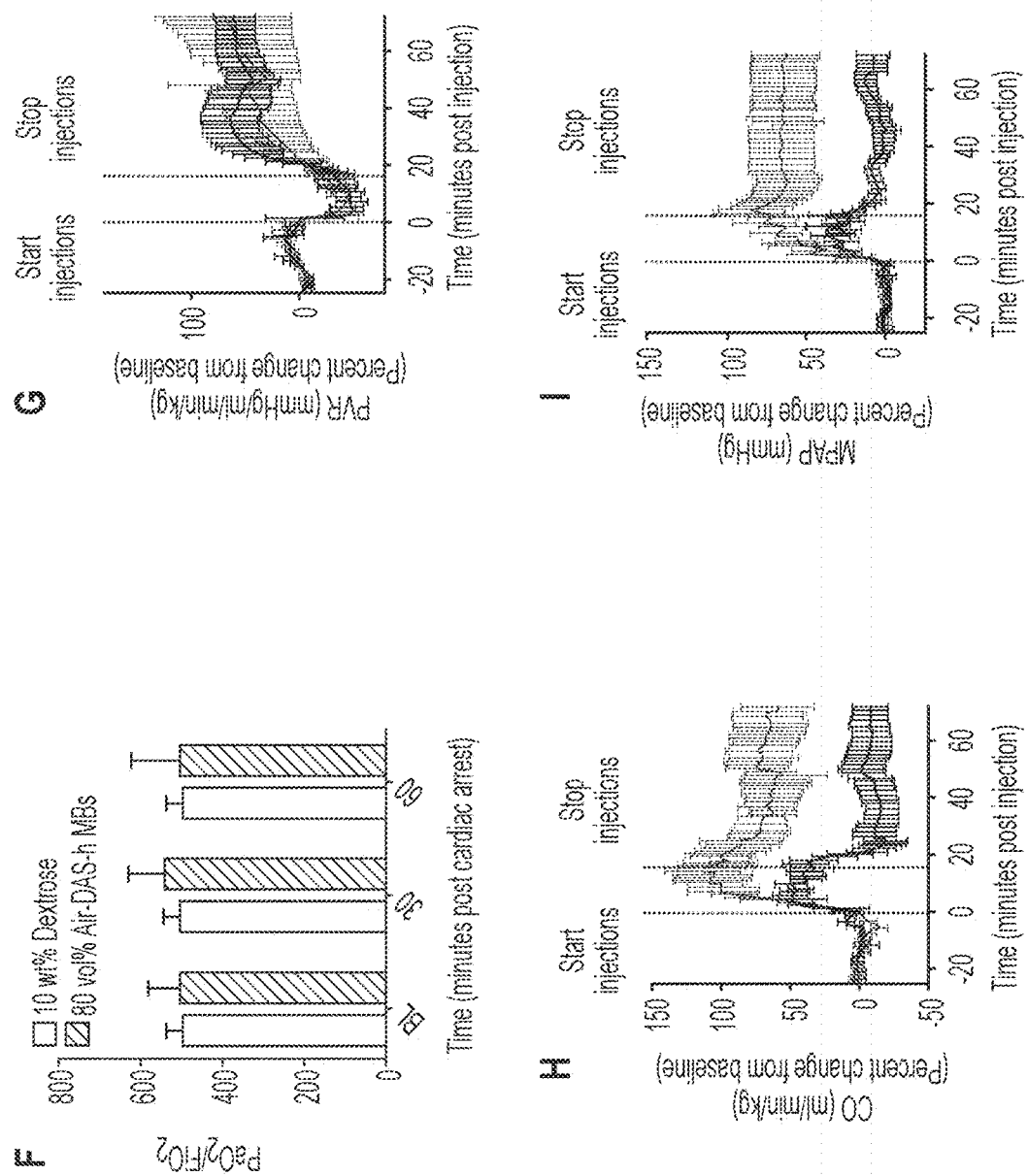
Figure 14:
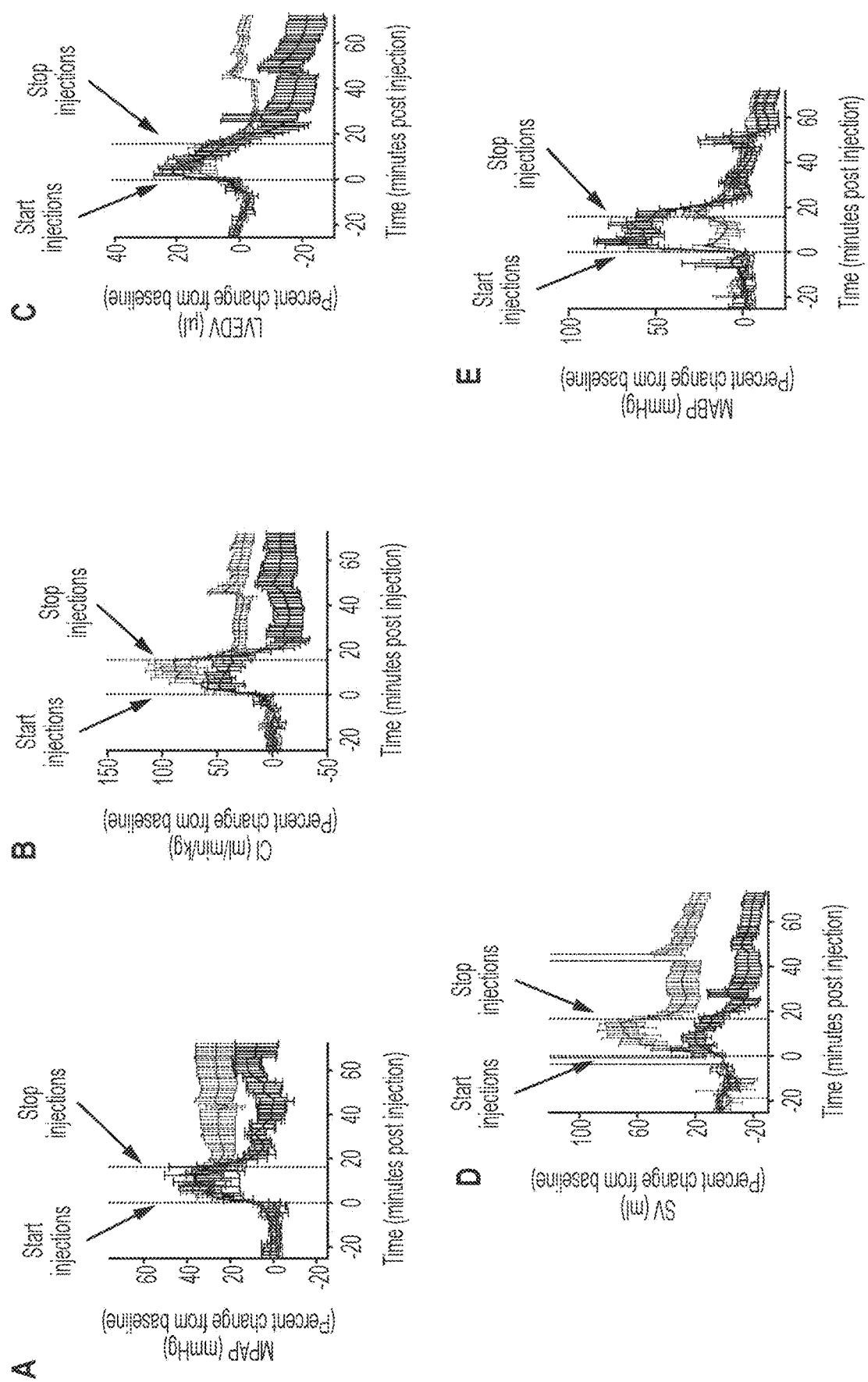
FIG. 14 shows hemodynamic data following i.v. infusion of 40 vol % Ox-DAS-h MBs. Animals receiving repeated infusions of Ox-DAS-h MBs experienced increased mean pulmonary arterial pressure (Panel A, MPAP, mean difference=−20.739, P=0.017), cardiac index (Panel B, CI, mean difference=−30.005, P=0.007), left ventricular end diastolic volume (Panel C, LVEDV, mean difference=−16.117, P=0.029), and stroke volumes (Panel D, SV, mean difference=−35.914, P<0.0001), and decreased systemic vascular resistance (Panel F, SVR, mean difference=45.157, P=0.004), and pulmonary vascular resistance (Panel G, PVR, mean difference=44.479, P<0.0001). There was no difference in the left ventricular end diastolic pressure (Panel H, LVEDP, mean difference=−34.907, P=0.700), heart rate (Panel I, HR, mean difference=−8.131, P=0.071), and mean arterial blood pressure (Panel E, MABP, mean difference=−15.172, P=0.098). Panel J shows that the $PaO_2/FiO_2$ ratio was similar between groups at baseline, 30 minutes, and 60 minutes post cardiac arrest. Error bars represent the standard error of the mean.
Figure 14:
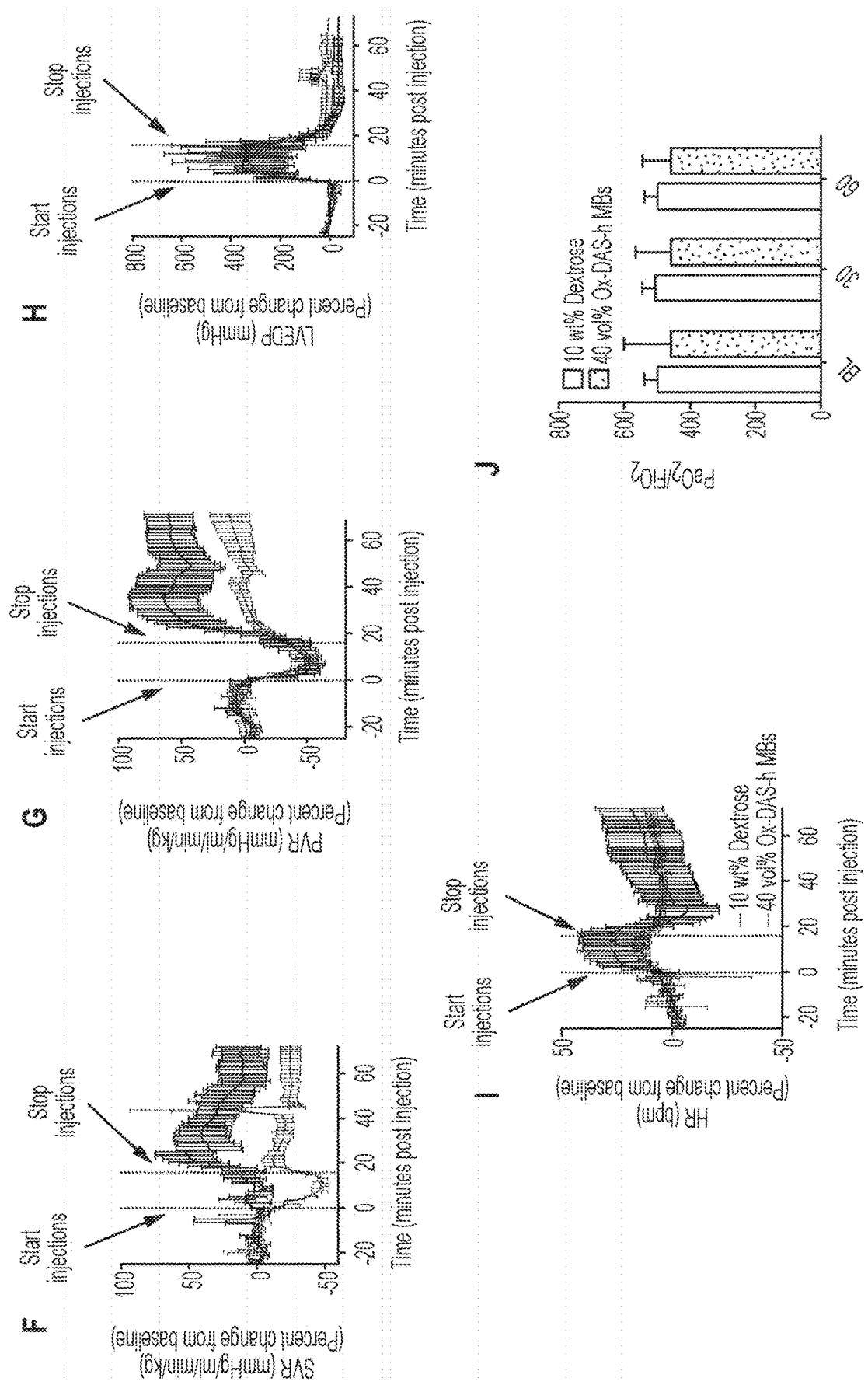
Figure 18:
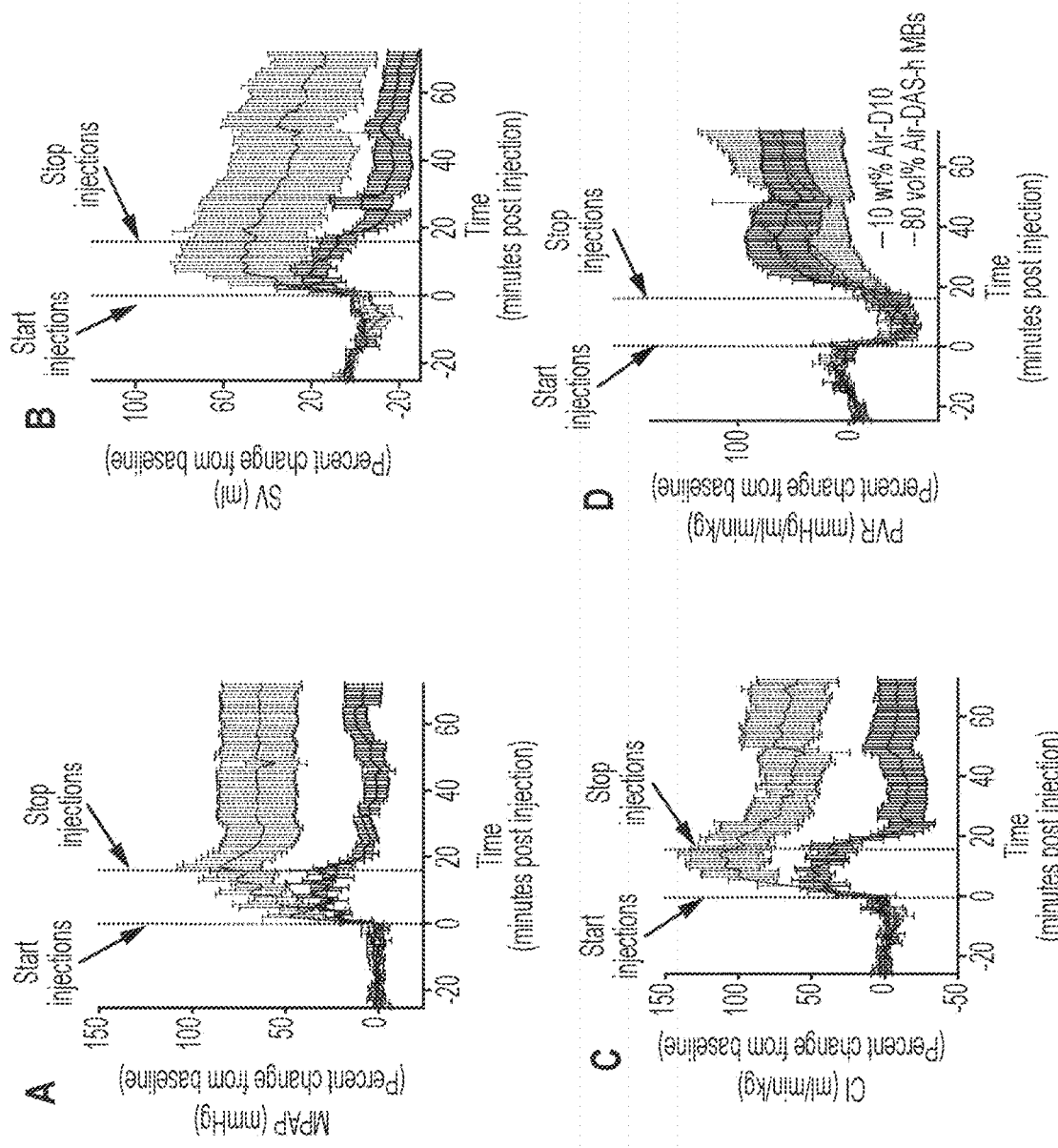
FIG. 18 shows that intravenous injection of concentrated air-filled DAS-h MBs is safe in rodents. Animals received either 5 mL of an 80 vol % Air-DAS-h MB foam suspension (in D10, n=5, test group) or 5 mL of air-saturated dextrose (10 wt %, n=5, control group, Air-D10) every 2 min over a 10 min period. Panels A-C show that the mean pulmonary arterial pressure (Panel A, mean difference=−30.941, P=0.001), stroke volume (Panel B, mean difference=−24.128, P=0.016), and cardiac index (Panel C, mean difference=−55.188, P<0.0001) were significantly higher for animals receiving Air-DAS-h MBs. Panel D shows that pulmonary vascular resistance was significantly lower following infusion of Air-DAS-h MBs (mean difference=39.263, P<0.0001). Control animals treated with Air-D10 are represented by the black curve, and animals receiving Air-DAS-h MBs are represented by the green curve.
Figure 23:
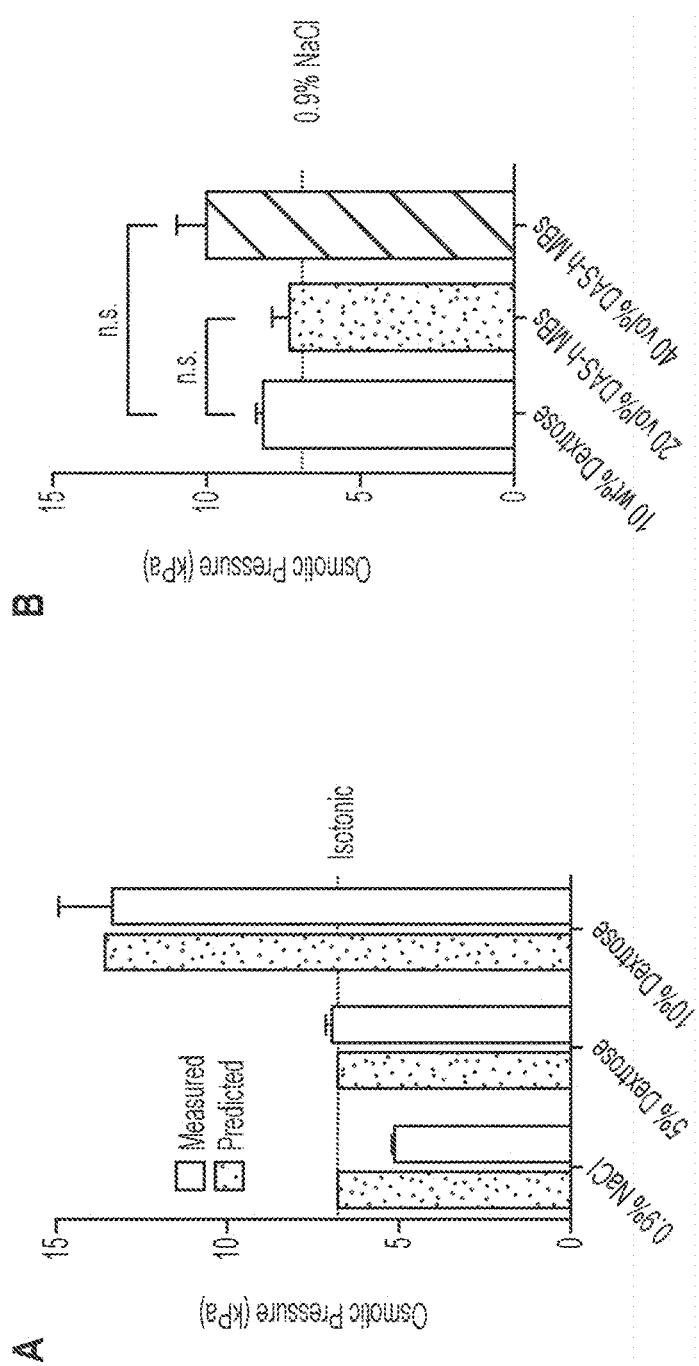
FIG. 23 shows the oncotic effects of DAS-h MBs. Panel A shows the osmotic pressure due to saline (0.9 wt %) and dextrose (5 and 10 wt %). Predicted values were obtained using the Jacobus van't Hoff equation. Panel B shows the osmotic pressure due to the presence of DAS-h MBs at 0, 20, and 40 vol %. Error bars represent the standard error of the mean.
Figure 24:
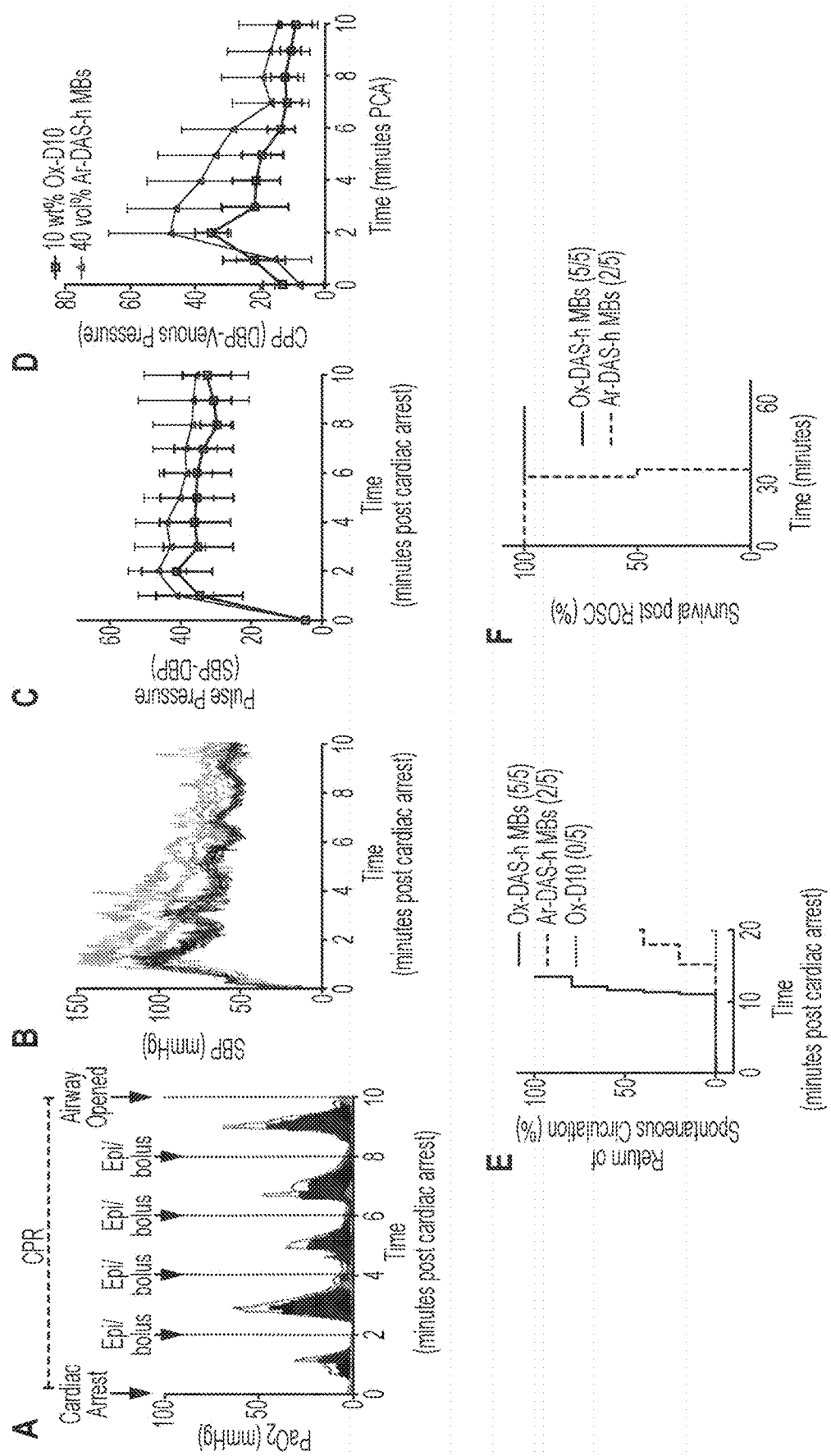
FIG. 24 shows hemodynamic data following treatment with Ar-DAS-h MBs in a rodent model of asphyxial cardiac arrest. Panel A shows that the arterial oxygen tensions in animals receiving Ar-DAS-h MBs (blue curve) were lower than those treated with Ox-D10 alone (black curve). Panel B shows that animals treated with Ar-DAS-MBs maintained elevated blood pressures during cardiac arrest (mean difference at 10 min=−12.038, P=0.041). Panels C and D show that there was no difference in pulse pressure (PP, Panel C, mean difference at 10 min=−3.143, P=1.00) or coronary perfusion pressure (CPP, Panel D, mean difference at 10 min=5.154, P=0.751) during cardiac arrest between groups. Panel E shows that only two animals treated with Ar-DAS-h MBs exhibited return of spontaneous circulation. Panel F shows that animals treated with Ar-DAS-h MBs who exhibited ROSC did not survive the 1-hour observation period. Panels G-L show that arterial blood gases were run at baseline (BL), 3, 6, and 9 minutes post cardiac arrest to monitor $HCO_3$ (Panel G), $PaCO_2$ (Panel H), hemoglobin concentration (Panel I), $PaO_2$ (Panel J), $SaO_2$ (Panel K), and pH (Panel L). Animals treated with Ox-D10 did not experience return of spontaneous circulation (ROSC). Error bars represent the standard error of the mean.
Figure 24:
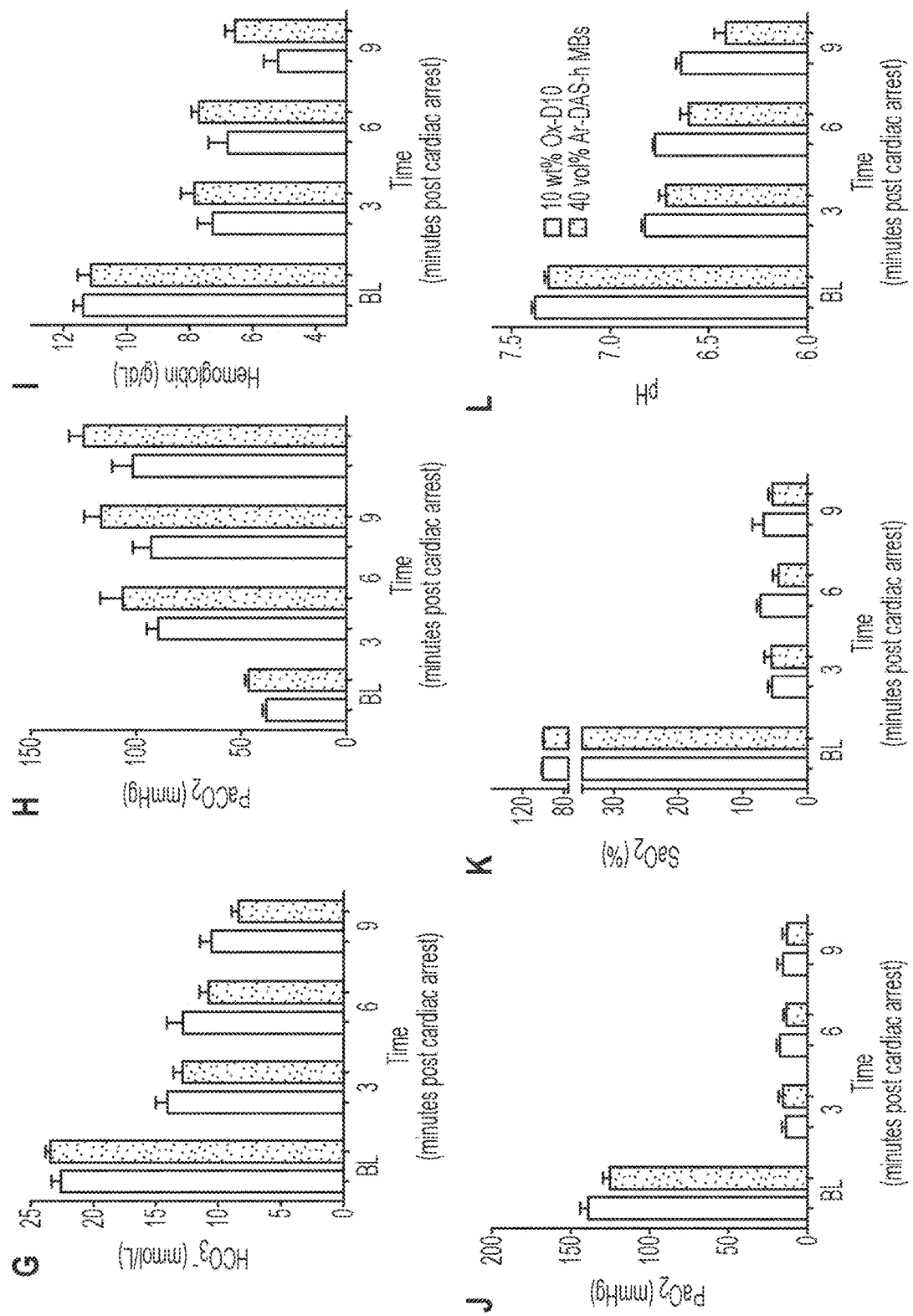

To examine the acute hemodynamic effects following intravenous injection of DAS-h MBs, rodents were anesthetized, intubated, and instrumented for the direct measurement of cardiac output using conductance catheters and of pulmonary arterial pressure using microtip catheters. While breathing 100% oxygen (to maximally saturate the arteries, veins, and tissues with dissolved oxygen), repeated boluses of 2.4 mL of air-loaded DAS-h MBs (Air-DAS-h; 5 mL of 80 vol %) (Group 1) or repeated boluses of 2.4 mL of air-loaded DAS-1 MBs (Air-DAS-1; 5 mL of 80 vol %) (Group 2) were administered intravenously every 2 minutes (5×, 12 mL air total), followed by a 1-hour observation period; control animals received aerated D10 (Air-D10) of equal volumes (Group 3). During acute injections, there were expected increases in mean pulmonary arterial pressure (MPAP), stroke volume (SV), and cardiac index (CI) for both groups, likely related to volume administration, which quickly returned to baseline in controls but remained elevated in animals treated with Air-DAS-h MBs (FIG. 18, panel A-C; FIG. 12, panels A-F and FIG. 14, panels A-J; and Tables 1-3). This is due to the oncotic effects of the nanoaggregates following dissolution of the DAS-h MB shell, which was found to be dose dependent (i.e. the volume expansion effect was less at lower concentrations, FIG. 23, panels A-B). Interestingly, the mean pulmonary vascular resistance (PVR) was lower for Air-DAS-h MBs, likely reflecting the vasodilatory effects of oxygen on the pulmonary vasculature (FIG. 18, panel D). No adverse effects on hemodynamics or lung function were noted during the subsequent observation period (FIG. 12, panels A-F, FIG. 14, panels A-J, and FIG. 24, panels A-L). Collectively, these results indicate that rapid infusion of concentrated DAS-h foams is safe and does not result in microvascular obstruction when rapidly infused at 80 vol %.

Figure 13:
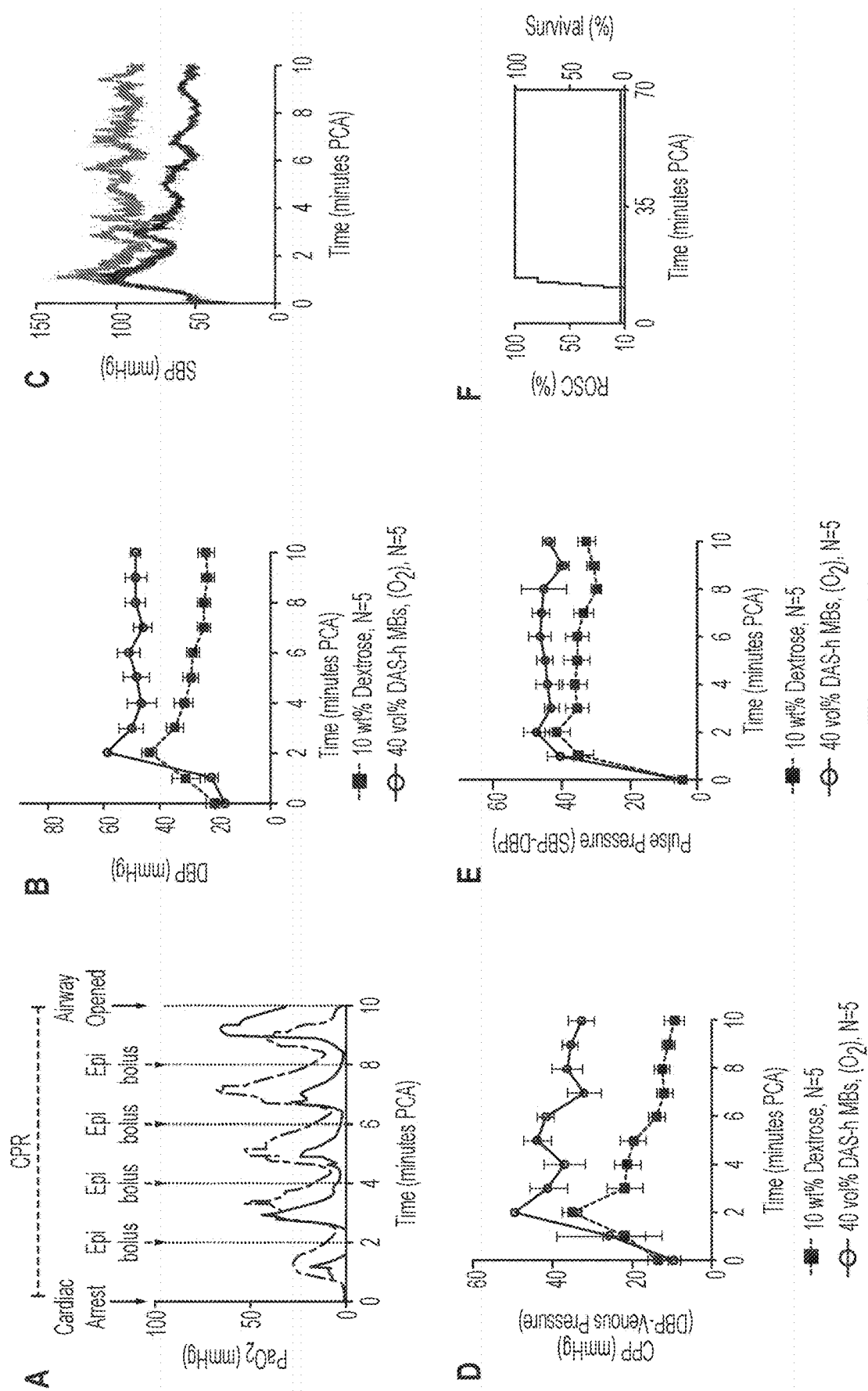
FIG. 13 (panels A-F) shows effects of exemplary stable particles on oxygenation, hemodynamics, and outcomes in asphyxial cardiac arrest.
Figure 19:
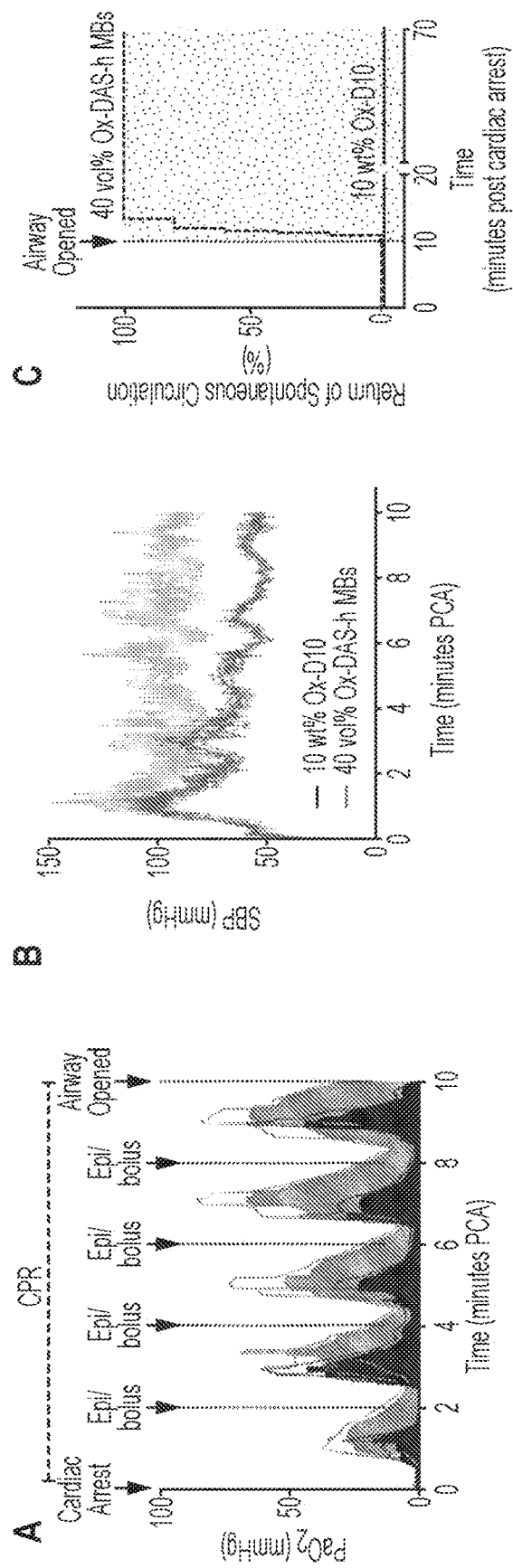
FIG. 19 shows that oxygen-loaded DAS-h MBs improve outcomes following asphyxial cardiac arrest. Animals received either 4 mL of a 40 vol % Ox-DAS-h MB suspension (in D10, n=5, test group) or 4 mL of oxygen-saturated dextrose (10 wt %, n=5, control, Ox-D10) every 2 min during cardiac arrest for 10 min. Panels A and B show arterial oxygen tensions (Panel A) and systolic blood pressure (Panel B) were continuously monitored during 10 minutes of cardiac arrest. Arterial oxygen tensions (Panel A) in animals receiving Ox-DAS-h MBs (red curve) increased significantly compared to those treated with Ox-D10 alone (black curve). Animals treated with Ox-DAS-MBs maintained elevated blood pressures during cardiac arrest (Panel B, mean difference=−28.556, P<0.0001). Panel C shows Kaplan-Meier plot of animals experiencing return of spontaneous circulation following restoration of mechanical ventilation (represented by shaded region).
Figure 25:
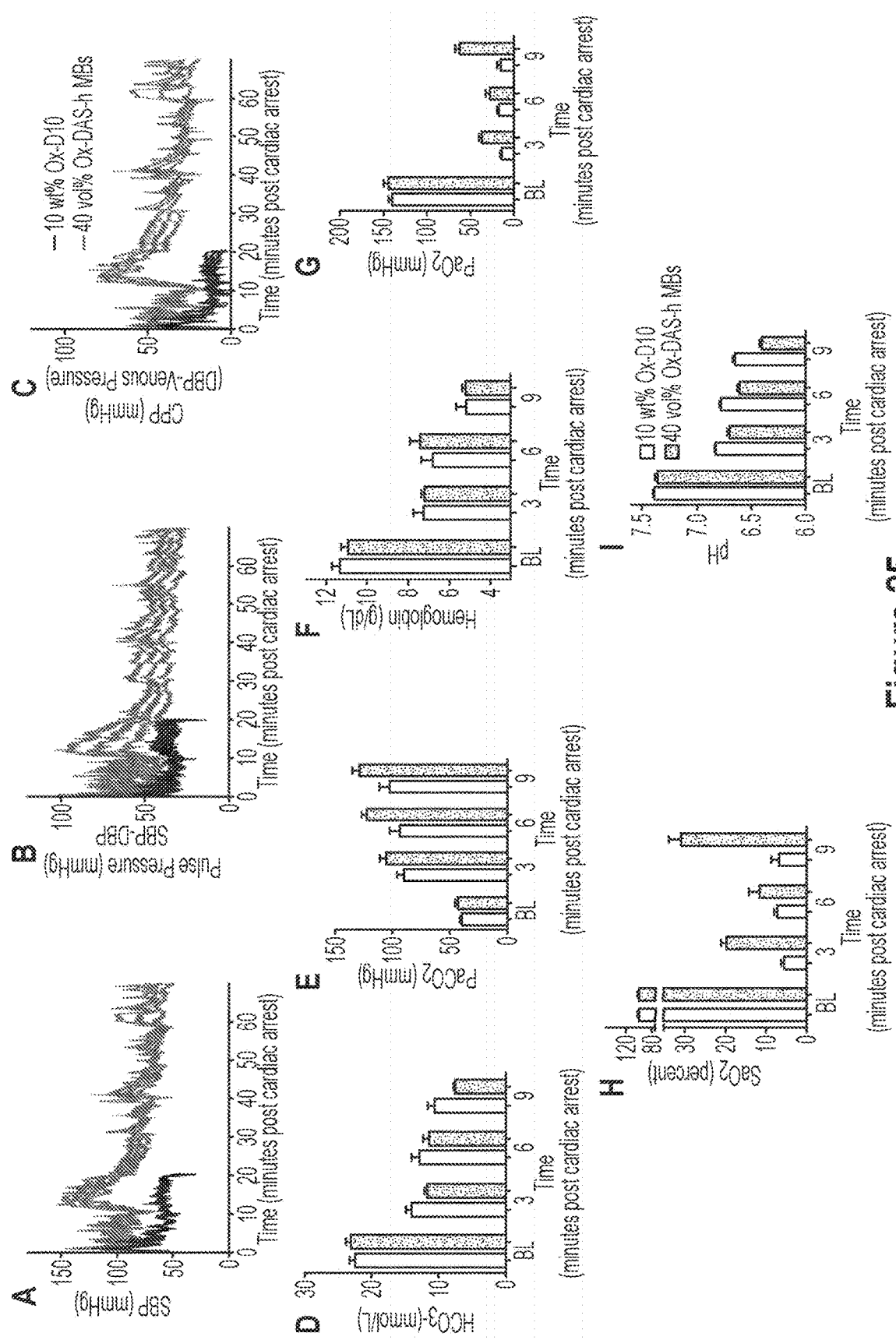
FIG. 25 shows hemodynamic data following rescue from asphyxial cardiac arrest. Animals receiving Ox-DAS-h MBs had higher systolic blood pressure (SBP, Panel A, mean difference=−28.556, P<0.0001), pulse pressure (PP, Panel B, mean difference=−8.656, P=0.23), and coronary perfusion pressure (CPP, Panel C, mean difference=−17.414, P<0.0001) during cardiac arrest compared to animals receiving Ox-D10 (10 wt % dextrose). All animals treated with Ox-DAS-h MBs exhibited ROSC and survived the 1-hour observation period with stable hemodynamics. Panels D-I show that arterial blood gases were run at baseline (BL), 3, 6, and 9 minutes post cardiac arrest to monitor $HCO_3$ (Panel D), $PaCO_2$ (Panel E), hemoglobin concentration (Panel F), $PaO_2$ (Panel G), $SaO_2$ (Panel H), and pH (Panel I). Error bars represent the standard error of the mean.
Figure 26:
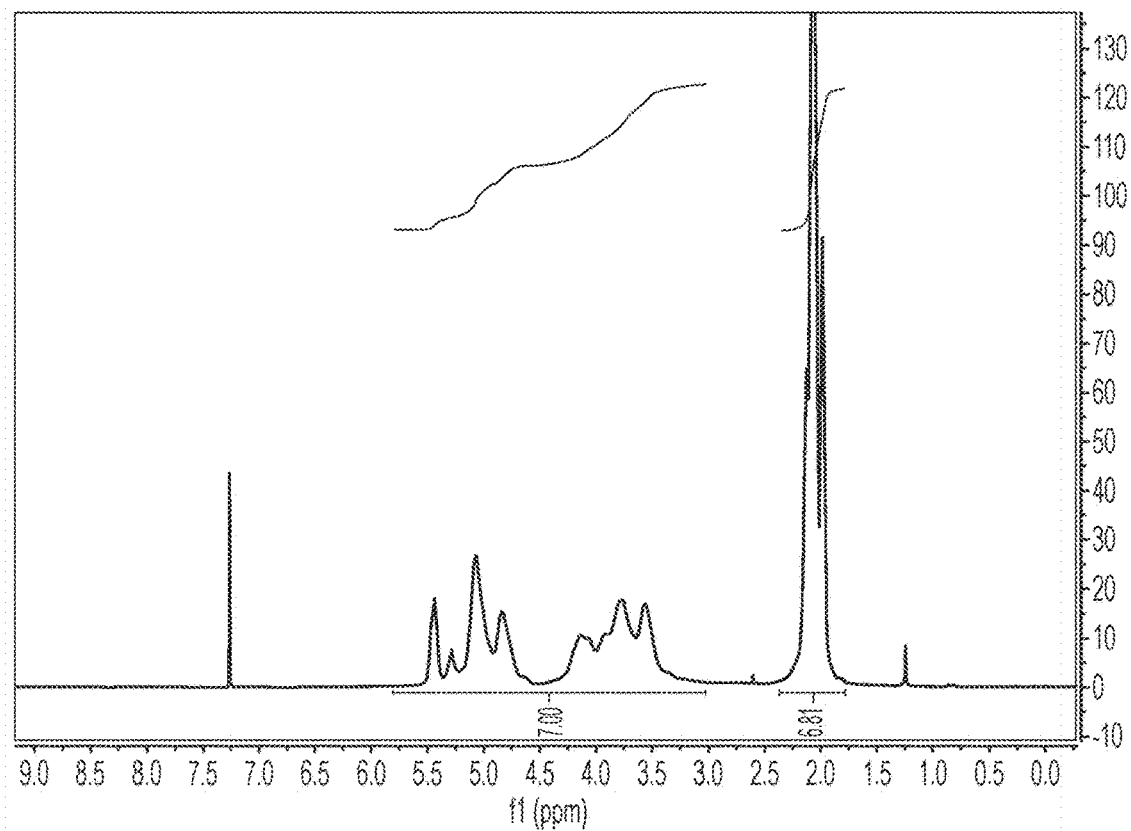
FIG. 26 shows a $^1H$ NMR of DA in DMF-d7.
Figure 27:
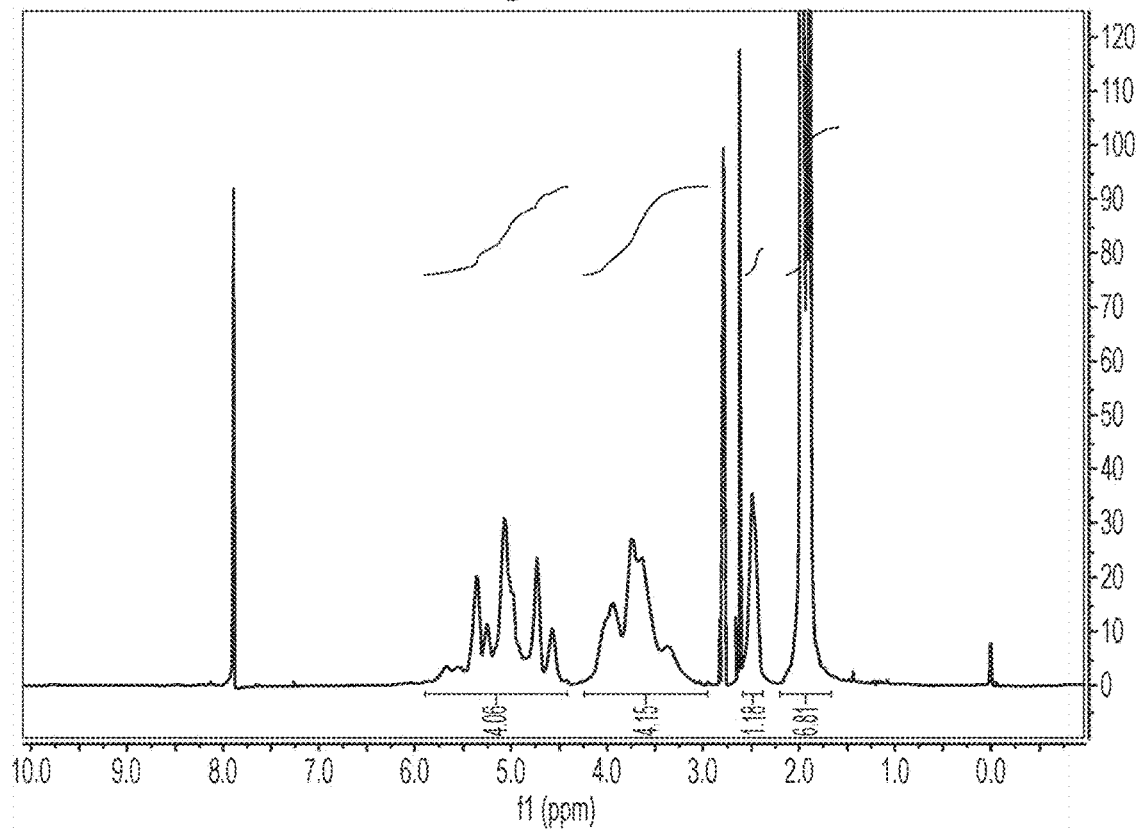
FIG. 27 shows a $^1H$ NMR of DAS-1 in DMF-d7.
Figure 28:
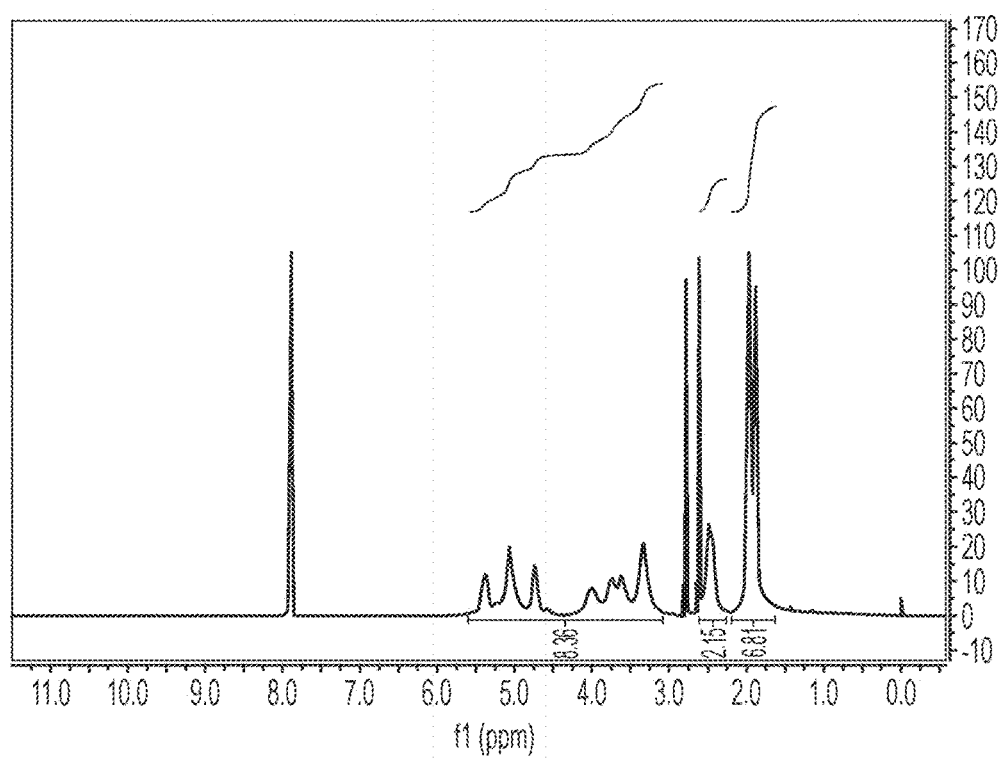
FIG. 28 shows a $^1H$ NMR of DAS-h in DMF-d7.
Figure 29:
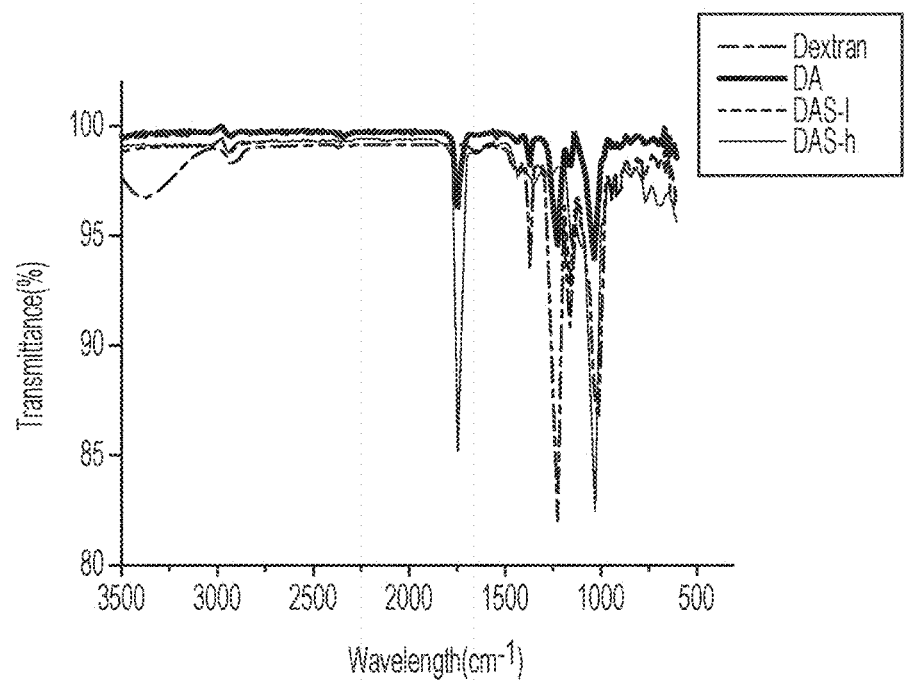
FIG. 29 shows an IR spectrum of dextran derivatives (Dextran, DA, DAS-1, and DAS-h).
Figure 30:
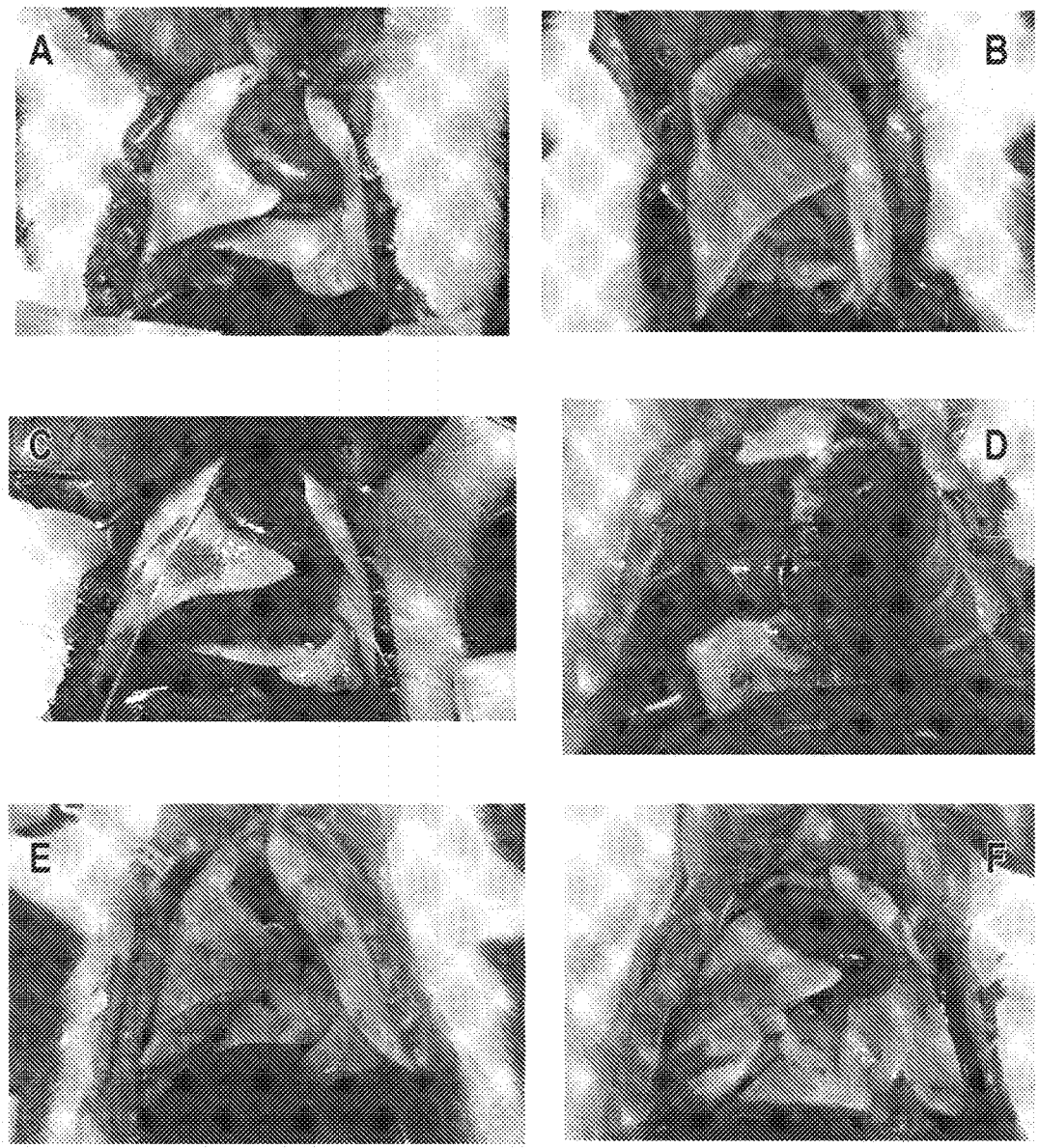
FIG. 30 shows photomicrographs of lung tissue following safety experiments. Panel A shows a representative lung image after receiving 5×5 ml 80 vol % air-filled DAS-h MB injection. Panel B shows a representative lung image after receiving 5×4 ml 40 vol % $O_2$-filled DAS-h MB injection. Panel C shows a representative lung image after receiving 5×5 ml 10% dextrose solution injection (control). Panel D shows an image of a damaged lung as a result of injecting MBs that do not hydrate or dissolve. Panel E shows a representative lung image after surviving the cardiac arrest model with MB treatment. Panel F shows a representative lung image from the control group in the cardiac arrest model, minor damage resulted from CPR.

Effects of DAS-h MBs on Oxygenation, Hemodynamics, and Outcomes in Asphyxial Cardiac Arrest To evaluate the therapeutic potential of DAS-h MBs, it was next to assess the ability to improve survival of rodents when added to a standard resuscitation algorithm following 10 minutes of asphyxial cardiac arrest (as described below) (24). Animals were randomized to receive 4 mL of DAS-h MB foams (40 vol %, ~1 mL $O_2$/injection) containing oxygen (Ox-DAS-h) or argon (Ar-DAS-h) or oxygenated carrier fluid (Ox-D10, serving as control) every 2 minutes during asphyxia. Following each dose of Ox-DAS-h, a sustained increase in $PaO_2$ was noted, which returned to baseline within 2 minutes as oxygen was continually consumed by the body, changes that were absent following administration of Ar-DAS-h MBs (FIG. 19, panel A and FIG. 25, panel A). A similar trend was observed following administration of Ox-D10, but to a significantly lesser extent (FIG. 13, panel A and FIG. 19, panel A). During early CPR, blood pressures were significantly improved in both MB groups compared to Ox-D10, potentially due to the volume expansion effect imparted by the MB shell. Later during CPR, however, only animals treated with Ox-DAS-h MBs exhibited superior hemodynamics, likely due to the systemic vasoconstricting effect of oxygen (FIG. 13, panels B-D; FIG. 19, panel B; FIG. 25, panels A-L and Tables 4-9). Following 10 minutes of CPR, the tracheal tube was opened and 100% oxygen administered, while CPR and medical resuscitation was continued for 10 additional minutes or until return of spontaneous circulation (ROSC). All animals treated with Ox-DAS-h exhibited a rapid ROSC (within 4 minutes), and all survived the 1-hour observation period with stable hemodynamics (FIG. 13, panel E; FIG. 19, panel C). Interestingly, 40% of the animals (⅖) receiving Ar-DAS-h MBs survived the primary cardiac arrest, likely due to the cytoprotective effects of argon gas, but suffered lethal arrests during the observation period. No animals treated with the Ox-D10 exhibited ROSC despite 10 additional minutes of CPR following relief of hypoxemia (FIG. 25, panels E-F and FIG. 19, panel C).

Discussion

Potential applications of bubbles are vast, yet their utility is severely hampered by lack of temporal control over bubble stability (18,19). As shown in this Example, nanoprecipitation of amphiphilic polymers at a/l interface allows fabrication of ultra-stable MBs, as well as control over their chemo-physical properties, with the potential capacity to manipulate shell morphology at the nanoscale (e.g., a "pollen-like" surface pattern (25) observed in DA MBs versus smoother and ultra-thin shells seen in DAS MBs that are also pH-responsive). The proper design of amphiphilic balance in polymers was found to be important to the success of interfacial nanoprecipitation, as derivatives that were too hydrophobic were not effective at stabilizing MBs were noted. For example, for Dextran polymers modified with acetyl groups, the cut-off is DS>2.5. However, for Dextran polymers modified with more hydrophobic moieties the DS needed to render them uneffective is lower. For example, acetyl is replaced with octyl, microbubbles cannot be made with DS>1.9.

Using the microbubble platform presented herein, stable particles of the invention were shown to successfully deliver meaningful bursts of oxygen and also to improve survival from asphyxial cardiac arrest, thus overcoming the limitations of existing IVO2 microcarriers. Several properties make stable particles of the invention a potentially transformative and easily translatable therapy to this lethal disease. First, stable particles of the invention have a long shelf life and controlled size distribution, features that are desirable for translation in an emergency environment (e.g., ambulance, crash cars, battlefield, etc.). Second, stable particles of the invention shells allow facile loading of oxygen (and other gases) post-fabrication, likely indicating that interstitial pores formed within nanoaggregate shells during nanoprecipitation (26). Third, the response trigger, such as a pH-trigger drives instant dissolution of the MB shell and the oxygen core, which allows large volumes of oxygen gas to be safely administered in rapid succession. In no in vivo experiments was vascular blockage noted, which was a problem in other gas delivery systems and would certainly forbid use in cardiac arrest. For example, the lipid shell, in LOMs, effectively retards bubble dissolution (27), even in the presence of an oxygen sink, leading to increased risk of vascular obstruction. In contrast, i.v. injection of nitrogen ($N_2$) and Argon (Ar)-loaded DAS-h MBs, under non-sink conditions, did not result in gas emboli; it is contemplated that by actively accelerating bubble dissolution, complications (e.g., gas nucleation, microparticle jamming) are prevented from occurring or from becoming lethal before outgassing can occur in the lung, thereby greatly increasing the safety profile.

Hyperoxia during reperfusion is known to be harmful following resuscitation from cardiac arrest (28); however, animals never achieved a hyperoxic state, demonstrating that the administration of $IVO_2$ can be titrated to maintain $PaO_2$ within a narrow range. In this experiment, a model of asphyxial cardiac arrest in which the burden of arterial hypoxemia was extreme, as it is in many hospitalized patients suffering from cardiac arrest, was used. Given the partial response to Ar-DAS-h MBs in that setting, the therapeutic benefit of stable particles of the invention likely resulted from a combination of the volume expansion effect of MBs as well as their oxygen carrying capacity. It is also known that argon itself exhibits cytoprotective properties (29), a feature that may have favored survival in the negative control group. However, since the primary target of cardiac arrest therapy in all settings is to optimize myocardial and cerebral oxygen delivery (30), it is possible that the administration of injectable oxygen (with the possible addition of a cytoprotective gas to the gas core) during cardiac arrest of any etiology may improve oxygen delivery by raising arterial oxygen tensions, improving cardiac output during CPR through intravascular volume expansion, and permitting chest compressions to continue uninterrupted throughout a resuscitation, a feature that has been shown to be critical to improving neurologic outcomes (31).

This MB platform may also have a significant impact in other fields of medicine. For instance, stable particles of the invention may be useful adjuncts to improve the efficacy of immuno- and radiotherapies for cancer (32) or to accelerate the healing of diabetic ulcers, non-healing wound, or burn injuries. They could be further used to improve oxygen delivery during organ procurement, as volume expanders in shock states, or as alternative ultrasound diagnostic imaging agents. The incorporation of other medical gases into this system, as well as its potential for chemical modifications/bioconjugations may further broaden its utility in a number of medical and non-medical applications.

Exemplary Methods

Fabrication of Microbubbles (MBs)

First, 100 mg of a dextran derivative (DA, DAS-1, or DAS-h) was dissolved in 2.2 mL of DMSO and transferred to a 50 ml conical tube. Then, 1 mL of water was added into DMSO mixture, which resulted in a viscous, opaque solution. The conical tube was immersed in ice water, and crude foam was generated by applying high-shear homogenization (Heidolph SilentCrusher M mixer) to the DMSO/water solution at the air-liquid interface at 15,000 RPM for 2 minutes. The crude foam was immediately diluted with 30 mL of water and mixed through gentle shaking. The foam solution was left at room temperature to let MBs naturally cream to the top, and the bottom solution was withdrawn from the conical tube with a syringe. This wash step was repeated with water and then with 10% dextrose solution (D10) multiple times. Multiple batches of MBs were then combined and stored in D10 at room temperature.

Cryo-Scanning Electron Microscopy (SEM).

Samples were frozen in slush nitrogen (SN2), then transferred into a MED 020 fitted with freeze fracture chamber. Samples were fractured at a temperature of −150° C. and etched for 8 minutes at −95° C. and coated with 7 nm of PT/Pd. The sample was then transferred to a Zeiss Nvision 40 fitted with a Cryo stage using VCT 100 cryo transfer devise and imaged at −150° C.

Quantification of Gas Carrying Capacity of Microbubbles.

Known volumes of MB cream (100% foam) were weighed and the mass was subtracted from the mass of water of an equivalent volume. The mass difference was then divided by the density of water (1 g/ml) in order to estimate the gas fraction of the MB cream, assuming the mass of MB shells was negligible.

Quantification of Oxygen Delivery to Deoxygenated Human Blood Using MBs.

Varying concentrations of MB foam suspended in D10 solution were loaded with $O_2$ by purging 1 ml aliquots for 48 hours under 100% $O_2$ atmosphere. Donated human red blood cells (hRBCs) (hemoglobin concentration≈6.2 g/dl, pH=7.3, and T=37° C.) were desaturated of dissolved $O_2$ by bubbling a $N_2/CO_2$ (95:5) mixture until the oxyhemoglobin saturation ($SO_2$) was ≤10%. A 3.5 ml sample of deoxygenated hRBCs was loaded into a 5 mL syringe (BD) and the baseline oxygen saturation was immediately measured with a blood gas analyzer (Radiometer ABL 80 Co-Ox Flex). Subsequently, the syringe containing hRBCs was immediately connected with another 5 mL syringe that contained the oxygenated MB sample through a three-way stopcock. The oxygenated MB foam and human blood were mixed by slowly pushing plungers back and forth repeatedly for 1 minute. The increase in $SO_2$, the partial pressure of $O_2$ in solution ($PaO_2$), and the hemoglobin concentration were then measured using the blood gas analyzer. For a control, 1 mL of $O_2$-saturated D10 solution containing no MBs was mixed with the deoxygenated hRBCs using the same protocol. The volume of oxygen ($VO_2$) delivered to the blood from the MBs was calculated using the following equation:

$$VO_2(mL) = \left[\left(\frac{1.36 \text{ ml}_{O_2 \text{ Gas}}}{g_{Hgb}} \times \frac{C \times g_{Hgb}}{dL_{Blood}} \times \frac{\Delta SO_2}{100}\right) + \left(\frac{0.0031}{mmHg} \times PaO_2\right)\right] \times V \times dL_{blood}$$

In this Example, 1.36 is the oxygen carrying capacity (ml) of hemoglobin on a per gram basis; C (g/dl) is the concentration of hemoglobin, $\Delta SO_2$ is the change in $SO_2$ from baseline after adding MBs or D10 solutions, 0.0031 is the conversion constant, and V (mL) is the total volume of the blood. The contribution of oxygen delivered to the hRBCs from the MBs was determined by subtracting the $VO_2$ of the control samples from the measured $VO_2$ of the MB samples.

Oxygen Release Kinetics

MB foam was loaded with oxygen and donated hRBCs were desaturated of oxygen using the procedures mentioned above. A blood oximetric catheter (Vigileo Monitor and PediaSat oximetry catheters; Edward Lifesciences) was inserted into a small aliquot of deoxygenated hRBCs and a baseline $SO_2$ was measured for 10 min while mixing at 1400 RPM at 37° C. The oxygen-loaded MB foam was then added to the deoxygenated hRBCs and the $SO_2$ was continuously measured for 1 hour.

Ex Vivo Blood Assays.

All procedures were approved by the Institutional Review Board (RB) at Boston Children's Hospital. Venous blood was collected from a healthy volunteer (RPS) in tubes containing heparin (17 μl/ml). The erythrocytes were washed four times by centrifugation at 500 g for 10 min and then suspended with Plasma-Lyte A (4 parts erythrocytes to 6 parts Plasma-Lyte A). DAS-h MB suspensions were prepared in D10 solution with increasing bubble concentrations (0-80% foam). Next, 100 μl of the stock erythrocyte solution was diluted with 790 μl of Plasma-Lyte A then added to 110 μl of the MB solution. The solutions were incubated at 37° C. with gentle rocking for 90 min. For a negative control, 100 μl of the stock erythrocyte solutions was added to 1 ml of Plasma-Lyte A (0% hemolysis), and for a positive control, 100 μl of the stock erythrocyte solutions was added to purified water (100% hemolysis). After incubation, the potassium concentration was measured with a blood gas analyzer (Radiometer ABL 80 Co-Ox Flex). Then, the serum was collected by centrifugation at 1,300 RPM for 15 minutes. Hemolysis was determined by measuring the absorbance at 540 nm. Release of Lactate Dehydrogenase (LDH) from the erythrocytes was measured using the LDH-based TOX-7 kit (Sigma-Aldrich) according to the manufacturer's instructions. Each experiment was repeated in triplicate and error bars represent standard error of the mean (SEM).

Complement Activation

Venous blood was collected from a healthy volunteer (RPS) in tubes containing heparin (17 μl/ml). Serum was separated from the erythrocytes by centrifugation at 3000 RPM for 10 minutes using serum separator tubes (BD). DAS-h MB suspensions were prepared in D10 solution with increasing MB concentrations (0-80% foam). Next, 890 μl of the blood serum was added to 110 μl of the MB solution and the solutions were incubated at 37° C. with gentle rocking for 90 minutes. For a negative control, 100 μL of Plasma-Lyte A was added to 900 μL of blood serum. The C3 and C4 complement activation were measured using the Human Complement C3 and C4 ELISA Kits (AssayPro) according to the manufacturer's instructions. Each experiment was repeated in triplicate and error bars represent SEM.

Thrombelastography

Venous blood was collected from a healthy volunteer (RPS) in a citrated collection tube (BD). An 80 vol % foam DAS-h MB suspension was prepared in D10 solution and 1 mL of the suspension as immediately added to 9 mL of blood. For a negative control, 1 mL of Plasma-Lyte A was immediately added to 9 mL of blood. Whole clot formation was immediately measured using a clinically used Thromboelatogram TEG 5000 analyzer (Haemonetics, Braintree, Mass.). The reaction time (R), the angle ($\alpha$), the kinetics time (k), the maximum amplitude (MA), and the Lysis 30 (LY30) were measured for each sample for both Arachidonic acid (AA) and adenosine diphosphate (ADP) pathways. Each experiment was repeated in triplicate and error bars represent SEM.

Hemodynamic Assessments During Oxygen Breathing

All procedures were approved by the Institutional Animal Care and Use Committee (IACUC) at Boston Children's Hospital. Male Sprague Dawley rats (400-500 g), (Charles River Laboratories®) were anesthetized with using ketamine (10 mg/kg, IP) and xylazine (4 mg/kg, IP) followed by inhalational isoflurane (0.5-2%). Animals were intubated and ventilated (SAR-1000, CWE, Inc.) with a tidal volume of 6.2 mL, positive end expiratory pressure (PEEP) of 5 cm $H_2O$, a peak inspiratory pressure (PIP) of 20 cm $H_2O$, and $FiO_2=1.0$. Instrumentation included catheters placed in the femoral artery and vein by cutdown for hemodynamic monitoring, followed by sternotomy and periventricular placement of a pressure-volume catheter into the left ventricle (Millar Mikro-Tip Pressure-Volume Catheter Transducer, 9 mm spacing, model SPR-847, 1.4 F) and a pressure catheter within the pulmonary artery (Millar Mikro-Tip Pressure Catheter Transducer, model SPR-671, 1.4 F). Following instrumentation, a baseline period of 30 minutes was observed, animals received repeated 5 mL boluses (5×) over 60 seconds of either Ox-DAS-h microparticles or carrier fluid every 2 minutes (total of 25 mL) (n=5 animals per group). Thereafter, animals were observed for a 60 minute observation period, with arterial blood gas analysis (ABL80 Flex CO—OX, Radiometer America) performed at 30 and 60 minutes. Left ventricular stroke volume (SV), left ventricular end diastolic volume (LVEDV), left ventricular end diastolic pressure (LVEDP), cardiac output (CO), cardiac index (CI), and pulmonary vascular resistance (PVR=[mean pulmonary arterial pressure-LVEDP]/CI) were exported Q60 seconds (LabChart Pro 8 software, ADInstruments) and compared between groups over time by linear mixed effects modeling with each variable as the output measure and treatment assignment as the predictor correcting for effects of time and repeated measures.

Effects of MB Injection Injections During Asphyxia Cardiac Arrest

Rodents were anesthetized and mechanically ventilated as described above. Instrumentation included a central arterial pressure catheter (Millar Mikro-Tip Pressure Catheter Transducer, model SPR-671, 1.4 F), a peripheral arterial catheter (for arterial blood sampling), and continuous arterial oxygen tension probe (E-Series Sensor, Oxford Optronix Ltd, Oxford, U.K.), all placed via femoral artery cutdowns. A venous catheter was similarly placed for medication administration. Following instrumentation, the $FiO_2$ was set to 0.3 and a 10 minute baseline period was observed. To maintain sedation and chemical paralysis during asphyxial cardiac arrest, IV sedation (ketamine 80 mg/kg and xylazine 10 mg/kg) and neuromuscular blocking agent (rocuronium 2 mg) were administered. Asphyxia was then induced by closing a stopcock on the tracheal tube, stopping all mechanical ventilation. No action was taken until the pulse pressure (systolic-diastolic blood pressure) reached ≤5 mmHg, which defined the onset of cardiac arrest. At that time, high quality, metronome-guided chest compressions were performed by a single provider (JNK) at 150 beats per minutes (BPM). Resuscitation medications included epinephrine (10 µg/kg) every 2 minutes, calcium gluconate (100 mg/kg), sodium chloride (3%, 2 mL/kg), and sodium bicarbonate (1 mEq/kg) administered every 5 minutes. Following each dose of epinephrine, animals received 4 mL of either Ox-DAS-h (40 vol %), Ar-DAS-h (40 vol %), or carrier fluid (n=5 rodents per group) every 2 minutes for 10 minutes. Ten minutes (5 doses of epinephrine and oxygen) following the onset of cardiac arrest, ventilation with $FiO_2$ 1 was restored. Chest compressions and epinephrine administration was continued until ROSC (defined as systolic blood pressure of >40 mmHg without chest compressions) occurred or 10 additional minutes had passed, at which time the experiment was considered a failed resuscitation. Arterial blood was collected at 3, 6, 9, 12, and 20 minutes following the onset of cardiac arrest. Surviving animals were supported in an intensive care environment, including mechanical ventilation and inotropic support, for up to 1 hour. $PaO_2$, systolic blood pressure, coronary perfusion pressure (diastolic blood pressure-venous pressure), and pulse pressure were exported and compared between groups as described above. Differences in ROSC rate and survival time were completed using a log rank test.

Statistical Information

Multiple means were compared using ANOVA analysis. All hemodynamic data was modeled using generalized linear mixed model in SPSS to account for the correlation between within subjects. Safety studies: medium values during baseline period (~30~0 minutes) and injection period (1-15 minutes) were taken for each subject as the original covariates of the model. A stepwise regression method (Akaike Information Criterion) on the fixed effect part of the model was used to determine significant covariates for the model. Efficacy studies: data across all time points were first used to examine the group effect over time and then analyzed only on time 0 and time 10 minutes. A significant level of 0.05 was chosen and Bonferroni test was used to adjust for multiple comparisons.

Supplemental Information

Exemplary Materials

Dextran (Mr ~40,000, from *Leuconostoc* spp.), 4-dimethyl aminopyridine (DMAP), acetic anhydride, succinic anhydride, dextrose (pharmaceutical grade), phosphate buffered saline, anhydrous dimethyl sulfoxide (DMSO), methanol, and diethyl ether were purchased from Sigma and used as received. Plasma-Lyte A was purchased from Baxter Corporation. All water used was deionized water ultrapurified by a Milli-Q System (18 MΩ; Millipore). Medical grade oxygen, argon, and $N_2/CO_2$ (95:5) gas were purchased from Air Gas and used as received.

General Methods

Nuclear magnetic resonance (NMR), 1H spectra were recorded in deuterated solvents on a Varian spectrometer at 400 MHz magnet. Fourier transform infrared spectroscopy (FTIR) was conducted on a Spectrum One FT-IR Spectrometer (PerkinElmer) with polymer powders. Dynamic light scattering (DLS) was conducted on a DelsaNano C instrument to measure the size of the polymer micelles. Light obscuration (Accusizer 780A) was used to measure size distribution of MBs. Viscosity measurement was conducted on a AR2000ex rheometer (TA Instruments).

Acetylation of Dextran

In a 150 mL round bottom flask, 5 g of dextran, 12 g of 4-dimethylaminopyridine (DMAP), and 6 mL of acetic anhydride were dissolved in 50 mL of anhydrous DMSO as a clear solution. The flask was placed in an oil bath with controlled external heating. The reaction was performed at 55° C. for 20 hours with magnetic stirring under $N_2$ atmosphere. Afterward, the reaction flask was removed from the oil bath and cooled to room temperature. The reaction mixture was then added drop-wise to 1.6 L of methanol under vigorous stirring to remove unwanted reactants and solvent and precipitate the acetylated dextran (DA). The crude DA product was collected by centrifugation and washed with methanol for three additional times. The final product was dried under high vacuum at 0.2 Torr at room temperature for 48 hours, and collected as a white powder. $^1$H NMR (400 MHz, CDCl3) δ: 5.51-3.33 (br, Sugar-H, 7H), 2.21-1.88 (3H, br, —$COCH_3$, 3H). The degree of substitution (DS) by acetylation based on $^1$H NMR was calculated to be 2.27.

Succinylation of Acetylated Dextran

In a 100 mL round bottom flask, 5 g of DA (DS Ac 2.27), 3 g (high substitution) or 1 g (low substitution) of DMAP, and 1.2 g (high substitution) or 0.4 g (low substitution) succinic anhydride were dissolved in 50 mL anhydrous DMSO as a clear solution. The flask was placed in an oil bath with controlled external heating. The reaction was performed at 55° C. for 20 hours with magnetic stirring under $N_2$ atmosphere. Afterward, the reaction flask was removed from the oil bath and cooled to room temperature. The reaction mixture was then added drop-wise to 2 L of diethyl ether under vigorous stirring to remove unwanted reactants and solvent and yielded the DAS as a polymer precipitate. Crude DAS product was collected by vacuum filtration and washed with additional diethyl ether. The final product was dried under vacuum at 0.2 Torr at room temperature for 48 hours and collected as white powder. $^1$H NMR (400 MHz, DMF-d7) δ, DAS-1: 5.80-3.10 (br, Sugar-H, and —OH), 2.48 (m, br, —$CH_2$—, 4H), 2.07-1.80 (br, —$COCH_3$), the DS of DAS-1 based on $^1$H NMR was calculated to be Ac 2.27, Suc 0.29. DAS-h: 5.52-1.71 (br, Sugar-H, and —OH), 2.48 (m, br, —$CH_2$—, 4H), 2.08-1.71 (br, —$COCH_3$); the DS of DAS-h based on 1H NMR was calculated to be Ac 2.27, Suc 0.54.

Loading MB Foam with Oxygen Gas

MB foam of various concentrations in D10 solution was added to a 100 mL three neck round bottom flask that was sealed with rubber septum and connected to a Schlenk line through stainless steel needles. Pure $O_2$ gas was allowed to pass through the Schlenk line and the foam was purged under a slightly positive pressure for >48 hours. To confirm the MBs were full loaded with $O_2$, a small aliquot of the foam was immediately measured by a blood gas analyzer (Radiometer ABL 80 Co-Ox Flex) to assure that $pO_2$ of the foam solution was ≥770 mmHg Prior to intravenous injection, the gas-loaded foam was withdrawn into a syringe and capped with a gas tight seal.

Dissolution/Hydration of DAS MBs Triggered by pH

A 20 μl aliquot of MB solution was placed between a glass slide and a cover slip. The optical images of the MBs were recorded using an Olympus IX71 microscope equipped with a CCD camera (Qimagine RETIGA 200R Fas B94) with a 96× objective (Uplan FLN). A 5 μl aliquot of Plasma-Lyte A solution was the added to the edge of cover slip and allowed to diffuse into and mix with the MBs. The dissolution of MBs due to the change in pH was subsequently recorded.

Change in solution turbidity was used to characterize the DAS-h MB dissolution behavior under different pH solutions using a UV/Vis spectrophotometer (Beckman DU 530). PBS solutions of varying pH were made by titration 1×PBS solution with 1N HCl solution until the desired pH was obtained. 100 μl of MB Foam added to 3 mL of the PBS solution in a PMMA cuvette and gently mixed for 5 seconds. The absorption of the solution was then measured at a wavelength of 325 nm every 10 seconds with gentle rocking performed between each measurement. The size distribution of the nanoparticles were subsequently measured using a light scattering analyzer (DelsaNano C).

Oncotic Pressure

Oncotic pressure was measured using a Deluxe Osmometer (Carolina Biological Supply Company). Control solutions (0.9 wt % NaCl, 5 wt % Dextrose (D5), and D10) were measure and compared against predicted values using the equation $\pi = iMRT$. DAS-h MB foams were prepared at concentrations to mimic the osmotic pressure immediately post infusion using D5 as a model isotonic solution.

Tables

TABLE 1

Linear mixed model with accounting for subject correlation on acute hemodynamic effects by infusion of MBs at $FiO_2 = 0.3$

| | |
|---|---|
| Group 1 | 80 vol % Air-DAS-h MBs(5 × 5 ml), $FiO_2 = 0.3$ n = 5 |
| Group 2 | 80 vol % Air-DAS-1 MBs(5 × 5 ml), $FiO_2 = 0.3$ n = 4 |
| Group 3 | 10 wt % D10(5 × 5 ml), $FiO_2 = 0.3$, n = 5 |

| | Comparison between groups injection period + post-injection period | | | Comparison between groups injection period | | | Comparison between groups post-injection period | | |
|---|---|---|---|---|---|---|---|---|---|
| Variable | Group 1 | Group 3 | P-value | Group 1 | Group 3 | P-value | Group 1 | Group 3 | P-value |
| MABP | 25.6 ± 14.4 | 12.0 ± 32.5 | 0.12 | 23.7 ± 18.1 | 55.8 ± 27.4 | 0.031 | 26.1 ± 13.2 | −0.5 ± 20.9 | 0.0046 |
| MPAP | 45.4 ± 31.9 | 11 ± 17.9 | 0.0084 | 71.8 ± 33.8 | 26.2 ± 19.8 | 0.0061 | 37.8 ± 26.9 | 6.6 ± 14.8 | 0.016 |
| PVR | −6.3 ± 90.8 | 29.6 ± 62.3 | 0.32 | −83.8 ± 101.9 | −41.7 ± 30.2 | 0.34 | 16.0 ± 73.7 | 49.8 ± 53.6 | 0.35 |
| SVR | −10.4 ± 18.5 | 20.8 ± 38.5 | 0.042 | −20.7 ± 17.9 | 4.1 ± 23.1 | 0.01 | −7.4 ± 17.6 | 25.5 ± 40.7 | 0.064 |
| LVEDP | 53.2 ± 87.4 | 53.0 ± 233.0 | 0.99 | 145.7 ± 102.6 | 294.4 ± 366.8 | 0.4 | 26.6 ± 60.6 | −15.4 ± 103.2 | 0.14 |
| LVEDV | 3.2 ± 10.2 | −9.3 ± 18.9 | 0.06 | 7.9 ± 8.3 | 13.3 ± 13.4 | 0.32 | 1.8 ± 10.3 | −15.7 ± 14.8 | 0.027 |
| CI | 40.3 ± 27.7 | 2.9 ± 35.5 | 0.023 | 36.1 ± 29.9 | 38.8 ± 26.6 | 0.84 | 41.6 ± 27.0 | −7.3 ± 30.8 | 0.0072 |
| HR | 18.8 ± 17.4 | 12.3 ± 31.3 | 0.65 | 23.7 ± 22.3 | 23.1 ± 27.4 | 0.97 | 17.4 ± 15.5 | 9.2 ± 31.7 | 0.58 |
| SV | 14.7 ± 31.2 | −8.3 ± 21.9 | 0.1 | 6.7 ± 28.5 | 14.7 ± 18.6 | 0.54 | 17.0 ± 31.6 | −14.8 ± 18.1 | 0.039 |

TABLE 1-continued

Linear mixed model with accounting for subject correlation on acute hemodynamic effects by infusion of MBs at $FiO_2 = 0.3$

| Variable | Comparison between groups injection period + post-injection period | | | Comparison between groups injection period | | | Comparison between groups post-injection period | | |
|---|---|---|---|---|---|---|---|---|---|
| | Group 2 | Group 3 | P-value | Group 2 | Group 3 | P-value | Group 2 | Group 3 | P-value |
| MABP | 0.7 ± 35.6 | 12.0 ± 32.5 | 0.43 | 31.3 ± 29.0 | 55.8 ± 27.4 | 0.14 | −12.6 ± 30.2 | −0.5 ± 20.9 | 0.3 |
| MPAP | 75.7 ± 40.2 | 11 ± 17.9 | 0.00023 | 80.8 ± 45.4 | 26.2 ± 19.8 | 0.014 | 73.4 ± 38.0 | 6.6 ± 14.8 | <0.0001 |
| PVR | 122.9 ± 137.3 | 29.6 ± 62.3 | 0.011 | 9.9 ± 53.5 | −41.7 ± 30.2 | 0.018 | 172.4 ± 133.5 | 49.8 ± 53.6 | 0.024 |
| SVR | −4.7 ± 30.7 | 20.8 ± 38.5 | 0.14 | −21.6 ± 29.8 | 4.1 ± 23.1 | 0.013 | 2.7 ± 28.1 | 25.5 ± 40.7 | 0.38 |
| LVEDP | −10.0 ± 76.2 | 53.0 ± 233.0 | 0.31 | 77.3 ± 63.0 | 294.4 ± 366.8 | 0.28 | −48.5 ± 41.9 | −15.4 ± 103.2 | 0.23 |
| LVEDV | −9.0 ± 22.0 | −9.3 ± 18.9 | 0.34 | 13.7 ± 12.6 | 13.3 ± 13.4 | 0.94 | −19.0 ± 17.3 | −15.7 ± 14.8 | 0.17 |
| CI | 27.7 ± 62.5 | 2.9 ± 35.5 | 0.41 | 80.3 ± 51.9 | 38.8 ± 26.6 | 0.035 | 4.6 ± 51.9 | −7.3 ± 30.8 | 0.85 |
| HR | 35 ± 23.3 | 12.3 ± 31.3 | 0.18 | 27.1 ± 11.4 | 23.1 ± 27.4 | 0.76 | 38.4 ± 26.2 | 9.2 ± 31.7 | 0.083 |
| SV | −2.0 ± 39.8 | −8.3 ± 21.9 | 0.79 | 32.5 ± 23.6 | 14.7 ± 18.6 | 0.072 | −17.1 ± 35.9 | −14.8 ± 18.1 | 0.58 |

| Variable | Comparison between groups injection period + post-injection period | | | Comparison between groups injection period | | | Comparison between groups post-injection period | | |
|---|---|---|---|---|---|---|---|---|---|
| | Group 2 | Group 1 | P-value | Group 2 | Group 1 | P-value | Group 2 | Group 1 | P-value |
| MABP | 0.7 ± 35.6 | 25.6 ± 14.4 | 0.0088 | 31.3 ± 29.0 | 23.7 ± 18.1 | 0.48 | −12.6 ± 30.2 | 23.7 ± 18.1 | 0.0014 |
| MPAP | 75.7 ± 40.2 | 45.4 ± 31.9 | 0.073 | 80.8 ± 45.4 | 71.8 ± 33.8 | 0.67 | 73.4 ± 38.0 | 71.8 ± 33.8 | 0.021 |
| PVR | 122.9 ± 137.3 | −6.3 ± 90.8 | 0.0063 | 9.9 ± 53.5 | −83.8 ± 101.9 | 0.076 | 172.4 ± 133.5 | −83.8 ± 101.9 | 0.014 |
| SVR | −4.7 ± 30.7 | −10.4 ± 18.5 | 0.21 | −21.6 ± 29.8 | −20.7 ± 17.9 | 0.81 | 2.7 ± 28.1 | −20.7 ± 17.9 | 0.14 |
| LVEDP | −10.0 ± 76.2 | 53.2 ± 87.4 | 0.016 | 77.3 ± 63.0 | 145.7 ± 102.9 | 0.19 | −48.5 ± 41.9 | 145.7 ± 102.6 | 0.0032 |
| LVEDV | −9.0 ± 22.0 | 3.2 ± 10.2 | 0.01 | 13.7 ± 12.6 | 7.9 ± 8.3 | 0.28 | −19.0 ± 17.3 | 7.9 ± 8.3 | 0.0069 |
| CI | 27.7 ± 62.5 | 40.3 ± 27.7 | 0.39 | 80.3 ± 51.9 | 36.1 ± 29.9 | 0.03 | 4.6 ± 51.9 | 36.1 ± 29.9 | 0.034 |
| HR | 35 ± 23.3 | 18.8 ± 17.4 | 0.17 | 27.1 ± 11.4 | 23.7 ± 22.3 | 0.74 | 38.4 ± 26.2 | 23.7 ± 22.3 | 0.068 |
| SV | −2.0 ± 39.8 | 14.7 ± 31.2 | 0.36 | 32.5 ± 23.6 | 6.7 ± 28.5 | 0.08 | −17.1 ± 35.9 | 6.7 ± 28.5 | 0.082 |

TABLE 2

Linear mixed model with accounting for subject correlation on acute hemodynamic effects by infusion of Air-DAS-h MBs at $FiO_2 = 1$.

| Group 1 | 80 vol % Air-DAS-h MBs(5 × 5 ml), n = 5 |
|---|---|
| Group 2 | 10 wt % D10(5 × 5 ml), n = 5 |

| Variable | Comparison between groups injection period + post-injection period | | | Comparison between groups injection period | | | Comparison between groups post-injection period | | |
|---|---|---|---|---|---|---|---|---|---|
| | Group 1 | Group 2 | P-Value | Group 1 | Group 2 | P-Value | Group 1 | Group 2 | P-Value |
| MABP | 13.3 ± 32.6 | 47.2 ± 25.0 | 0.0021 | 55.8 ± 27.4 | 59.2 ± 22.6 | 0.74 | 0.2 ± 20.9 | 43.7 ± 24.6 | 0.00036 |
| MPAP | 11.2 ± 17.9 | 63.1 ± 40.8 | 0.012 | 26.2 ± 20.0 | 54.9 ± 38.0 | 0.081 | 6.6 ± 14.4 | 65.4 ± 41.3 | 0.0092 |
| PVR | 27.9 ± 62.9 | 23.2 ± 86.6 | 0.86 | −41.7 ± 30.2 | −29.5 ± 30.1 | 0.4 | 49.1 ± 54.4 | 38.2 ± 91.5 | 0.78 |
| SVR | 20.7 ± 37.9 | −9.1 ± 27.6 | 0.085 | 4.1 ± 23.1 | −9.8 ± 29.7 | 0.22 | 25.8 ± 40.1 | 8.9 ± 27.0 | 0.086 |
| LVEDP | 58.2 ± 238.1 | 79.9 ± 180.7 | 0.58 | 294.4 ± 366.8 | 272.8 ± 217.7 | 0.9 | −13.5 ± 106.2 | 25.3 ± 122.8 | 0.095 |
| LVEDV | −8.6 ± 19.0 | 6.6 ± 22.2 | 0.12 | 13.3 ± 13.4 | 19.4 ± 19.8 | 0.45 | −15.3 ± 15.0 | 3.0 ± 21.5 | 0.099 |
| CI | 2.9 ± 35.5 | 72.5 ± 51.9 | 0.0069 | 38.9 ± 26.6 | 80.6 ± 58.8 | 0.048 | −7.3 ± 30.8 | 70.2 ± 49.6 | 0.0083 |
| HR | 12.3 ± 31.3 | 37.1 ± 25.9 | 0.15 | 23.1 ± 27.4 | 34.6 ± 26.7 | 0.45 | 9.2 ± 31.7 | 37.8 ± 25.7 | 0.11 |
| SV | −8.3 ± 21.9 | 31.6 ± 55.6 | 0.11 | 14.7 ± 18.6 | 38.0 ± 57.1 | 0.3 | −14.8 ± 18.1 | 29.7 ± 55.2 | 0.088 |

TABLE 3

Linear mixed model with accounting for subject correlation on acute hemodynamic effects by infusion of Ox-DAS-h MBs at $FiO_2 = 1$.

| Group 1 | 40 vol % Ox-DAS-h MBs(5 × 5 ml), n = 5 |
|---|---|
| Group 2 | 10 wt % D10(5 × 5 ml), n = 5 |

| Variable | Comparison between groups injection period + post-injection period | | | Comparison between groups injection period | | | Comparison between groups post-injection period | | |
|---|---|---|---|---|---|---|---|---|---|
| | Group 2 | Group 1 | P-Value | Group 2 | Group 1 | P-Value | Group 2 | Group 1 | P-Value |
| MABP | 13.3 ± 32.6 | 4.4 ± 13.1 | 0.21 | 55.8 ± 27.4 | 11.3 ± 13.3 | 0.001 | 0.2 ± 20.9 | 2.3 ± 12.2 | 0.73 |
| MPAP | 11.2 ± 17.9 | 26.7 ± 15.8 | 0.067 | 26.2 ± 20.0 | 31.0 ± 14.3 | 0.6 | 6.6 ± 14.4 | 25.4 ± 16.1 | 0.044 |

TABLE 3-continued

Linear mixed model with accounting for subject correlation on acute hemodynamic effects by infusion of Ox-DAS-h MBs at $FiO_2 = 1$.

| | | | | | | | | | |
|---|---|---|---|---|---|---|---|---|---|
| PVR | 27.9 ± 62.9 | −10.5 ± 26.6 | 0.074 | −41.7 ± 30.2 | −40.9 ± 18.3 | 0.94 | −49.1 ± 54.4 | 1.3 ± 21.3 | 0.045 |
| SVR | 20.7 ± 37.9 | −25.4 ± 16.0 | 0.0059 | 4.1 ± 23.1 | −37.4 ± 15.3 | 0.00032 | 25.8 ± 40.1 | 21.7 ± 14.2 | 0.013 |
| LVEDP | 58.2 ± 238.1 | 75.0 ± 162.6 | 0.73 | 294.4 ± 366.8 | 263.4 ± 241.7 | 0.86 | −13.5 ± 106.2 | 17.8 ± 52.8 | 0.21 |
| LVEDV | −8.6 ± 19.0 | 1.4 ± 7.9 | 0.082 | 13.3 ± 13.4 | 11.4 ± 9.1 | 0.73 | −15.3 ± 15.0 | −1.7 ± 4.0 | 0.039 |
| CI | 2.9 ± 35.5 | 39.6 ± 30.3 | 0.019 | 38.9 ± 26.6 | 68.8 ± 42.7 | 0.1 | −7.3 ± 30.8 | 30.8 ± 17.5 | 0.019 |
| HR | 12.3 ± 31.3 | 7.4 ± 5.7 | 0.73 | 23.1 ± 27.4 | 11.3 ± 6.7 | 0.33 | 9.2 ± 31.7 | 6.2 ± 4.8 | 0.84 |
| SV | −8.3 ± 21.9 | 34.0 ± 25.6 | 0.0007 | 14.7 ± 18.6 | 55.0 ± 32.1 | 0.0075 | −14.8 ± 18.1 | 27.4 ± 19.1 | 0.0014 |

Tables 4-10—Statistical Analysis of Hemodynamics in ACA Model

TABLE 4

Statistical analysis of mean systolic blood pressure (SBP) overall

Estimates[a]

| | | | | 95% Confidence Interval | |
|---|---|---|---|---|---|
| group | Mean | Std. Error | df | Lower Bound | Upper Bound |
| Ar | 65.499[b] | 3.229 | 15.000 | 58.616 | 72.381 |
| O2 | 94.053[b] | 3.229 | 15.000 | 87.170 | 100.935 |
| Control | 79.973[b] | 3.229 | 15.000 | 73.091 | 86.856 |

Pairwise Comparisons[a]

| (I) group | (J) group | Mean Difference (I − J) | Std. Error | df | Sig.[c] | 95% Confidence Interval for Difference[c] Lower Bound | Upper Bound |
|---|---|---|---|---|---|---|---|
| Ar | O2 | −28.554* | 4.566 | 15.000 | .000 | −40.855 | −16.253 |
| | Control | −14.475* | 4.566 | 15.000 | .019 | −26.776 | −2.174 |
| O2 | Ar | 28.554* | 4.566 | 15.000 | .000 | 16.253 | 40.855 |
| | Control | 14.079* | 4.566 | 15.000 | .023 | 1.779 | 26.380 |
| Control | Ar | 14.475* | 4.566 | 15.000 | .019 | 2.174 | 26.776 |
| | O2 | −14.079* | 4.566 | 15.000 | .023 | −26.380 | −1.779 |

Based on estimated marginal means
*The mean difference is significant at the .05 level.
[a]Dependent Variable: SBP.
[b]Covariates appearing in the model are evaluated at the following values: time_sec = 300.0372.
[c]Adjustment for multiple comparisons: Bonferroni.

TABLE 5

Statistical analysis of mean systolic blood pressure (SBP) time comparison

| Time | (I) group | (J) group | Mean Difference (I − J) | Std. Error | df | Sig[c] | 95% Confidence Interval for Difference[c] Lower Bound | Upper Bound |
|---|---|---|---|---|---|---|---|---|
| 0 | Ar | O2 | −3.418 | 3.227 | 10.607 | .939 | −12.579 | 5.7431 |
| | | Control | −6.598 | 3.227 | 10.607 | .200 | −15.759 | 2.5631 |
| | O2 | Ar | 3.418 | 3.227 | 10.607 | .939 | −5.743 | 12.579 |
| | | Control | −3.180 | 3.227 | 10.607 | 1.000 | −12.341 | 5.981 |
| | Control | Ar | 6.598 | 3.227 | 10.607 | .200 | −2.563 | 15.759 |
| | | O2 | 3.180 | 3.227 | 10.607 | 1.000 | −5.981 | 12.341 |
| 10 | Ar | O2 | −27.708* | 4.426 | 18.792 | .000 | −39.340 | −16.076 |
| | | Control | 12.038* | 4.426 | 18.792 | .041 | .406 | 23.6701 |
| | O2 | Ar | 27.708* | 4.426 | 18.792 | .000 | 16.076 | 39.340 |
| | | Control | 39.746* | 4.426 | 18.792 | .000 | 28.114 | 51.378 |
| | Control | Ar | −12.038* | 4.426 | 18.792 | .041 | −23.670 | −.406 |
| | | O2 | −39.746* | 4.426 | 18.792 | .000 | −51.378 | −28.114 |

Based on estimated marginal means
*The mean difference is significant at the .05 level.
a. Dependent Variable: SBP.
[c]Adjustment for multiple comparisons: Bonferroni.

TABLE 6

Statistical analysis of mean pulse pressure overall

Estimates[a]

| group | Mean | Std. Error | df | 95% Confidence Interval | |
|---|---|---|---|---|---|
| | | | | Lower Bound | Upper Bound |
| control | 31.912[b] | 2.192 | 18.384 | 27.314 | 36.511 |
| O2 | 40.580[b] | 2.192 | 18.384 | 35.982 | 45.179 |
| Ar | 37.146[b] | 2.202 | 18.703 | 32.533 | 41.759 |

Pairwise Comparisons[a]

| (I) group | (J) group | Mean Difference (I − J) | Std. Error | df | Sig.[c] | 95% Confidence Interval for Difference[c] | |
|---|---|---|---|---|---|---|---|
| | | | | | | Lower Bound | Upper Bound |
| control | O2 | −8.668* | 3.100 | 18.384 | .035 | −16.832 | −.504 |
| | Ar | −5.234 | 3.107 | 18.543 | .327 | −13.409 | 2.942 |
| O2 | control | 8.668* | 3.100 | 18.384 | .035 | .504 | 16.832 |
| | Ar | 3.435 | 3.107 | 18.543 | .849 | −4.741 | 11.610 |
| Ar | control | 5.234 | 3.107 | 18.543 | .327 | −2.942 | 13.409 |
| | O2 | −3.435 | 3.107 | 18.543 | .849 | −11.610 | 4.741 |

Based on estimated marginal means
*The mean difference is significant at the .05 level.
[a]Dependent Variable: PP.
[b]Covariates appearing in the model are evaluated at the following values: time_min = 5.0122.
[c]Adjustment for multiple comparisons: Bonferroni.

TABLE 8

Statistical analysis of mean coronary perfusion pressure overall

Estimates[a]

| group | Mean | Std. Error | df | 95% Confidence Interval | |
|---|---|---|---|---|---|
| | | | | Lower Bound | Upper Bound |
| control | 17.393[b] | 2.374 | 19.696 | 12.437 | 22.350 |
| O2 | 34.937[b] | 2.400 | 20.667 | 29.942 | 39.933 |
| Ar | 25.693[b] | 2.343 | 18.880 | 20.787 | 30.600 |

Pairwise Comparisons[a]

| (I) group | (J) group | Mean Difference (I − J) | Std. Error | df | Sig.[c] | 95% Confidence Interval for Difference[c] | |
|---|---|---|---|---|---|---|---|
| | | | | | | Lower Bound | Upper Bound |
| control | O2 | −17.544* | 3.376 | 20.178 | .000 | −26.356 | −8.732 |
| | Ar | −8.300 | 3.335 | 19.287 | .066 | −17.043 | .444 |
| O2 | control | 17.544* | 3.376 | 20.178 | .000 | 8.732 | 26.356 |
| | Ar | 9.244* | 3.354 | 19.766 | .037 | .472 | 18.016 |
| Ar | control | 8.300 | 3.335 | 19.287 | .066 | −.444 | 17.043 |
| | O2 | −9.244* | 3.354 | 19.766 | .037 | −18.016 | −.472 |

Based on estimated marginal means
*The mean difference is significant at the .05 level.
[a]Dependent Variable: CPP.
[b]Covariates appearing in the model are evaluated at the following values: time_min = 5.0667.
[c]Adjustment for multiple comparisons: Bonferroni.

TABLE 7

Statistical analysis of mean pulse pressure time comparison
Pairwise Comparisons[a]

| time_min | (I) group | (J) group | Mean Difference (I − J) | Std. Error | df | Sig.[c] | 95% Confidence Interval for Difference[c] | |
|---|---|---|---|---|---|---|---|---|
| | | | | | | | Lower Bound | Upper Bound |
| .00 | control | O2 | −.740 | 3.237 | 29.919 | 1.000 | −8.951 | 7.470 |
| | | Ar | −.147 | 3.237 | 29.919 | 1.000 | −8.357 | 8.064 |
| | O2 | control | .740 | 3.237 | 29.919 | 1.000 | −7.470 | 8.951 |
| | | Ar | .594 | 3.237 | 29.919 | 1.000 | −7.617 | 8.804 |
| | Ar | control | .147 | 3.237 | 29.919 | 1.000 | −8.064 | 8.357 |
| | | O2 | −.594 | 3.237 | 29.919 | 1.000 | −8.804 | 7.617 |
| 10.00 | control | O2 | −10.967* | 3.237 | 29.919 | .006 | −19.178 | −2.757 |
| | | Ar | −3.143 | 3.237 | 29.919 | 1.000 | −11.353 | 5.068 |
| | O2 | control | 10.967* | 3.237 | 29.919 | .006 | 2.757 | 19.178 |
| | | Ar | 7.825 | 3.237 | 29.919 | .066 | −.386 | 16.035 |
| | Ar | control | 3.143 | 3.237 | 29.919 | 1.000 | −5.068 | 11.353 |
| | | O2 | −7.825 | 3.237 | 29.919 | .066 | −16.035 | .386 |

| Group | (I) time_min | (J) time_min | Mean Difference (I − J) | Std. Error | df | Sig.[c] | 95% Confidence Interval for Difference[c] | |
|---|---|---|---|---|---|---|---|---|
| | | | | | | | Lower Bound | Upper Bound |
| control | .00 | 10.00 | −28.223* | 3.152 | 15.000 | .000 | −34.941 | −21.504 |
| | 10.00 | .00 | 28.223* | 3.152 | 15.000 | .000 | 21.504 | 34.941 |
| O2 | .00 | 10.00 | −38.450* | 3.152 | 15.000 | .000 | −45.168 | −31.731 |
| | 10.00 | .00 | 38.450* | 3.152 | 15.000 | .000 | 31.731 | 45.168 |
| Ar | .00 | 10.00 | −31.219* | 3.152 | 15.000 | .000 | −37.937 | −24.500 |
| | 10.00 | .00 | 31.219* | 3.152 | 15.000 | .000 | 24.500 | 37.937 |

Based on estimated marginal means
*The mean difference is significant at the .05 level.
[a]Dependent Variable: PP.
[c]Adjustment for multiple comparisons: Bonferroni.

TABLE 9

Statistical analysis of mean coronary perfusion pressure time comparison
Pairwise Comparisons[a]

| time_min | (I) group | (J) group | Mean Difference (I − J) | Std. Error | df | Sig.[c] | 95% Confidence Interval for Difference[c] Lower Bound | Upper Bound |
|---|---|---|---|---|---|---|---|---|
| .00 | control | O2 | 3.856 | 4.150 | 31.214 | 1.000 | −6.643 | 14.355 |
| | | Ar | 5.378 | 4.150 | 31.214 | .614 | −5.121 | 15.877 |
| | O2 | control | −3.856 | 4.150 | 31.214 | 1.000 | −14.355 | 6.643 |
| | | Ar | 1.522 | 4.150 | 31.214 | 1.000 | −8.977 | 12.021 |
| | Ar | control | −5.378 | 4.150 | 31.214 | .614 | −15.877 | 5.121 |
| | | O2 | −1.522 | 4.150 | 31.214 | 1.000 | −12.021 | 8.977 |
| 10.00 | control | O2 | −23.405* | 4.402 | 31.165 | .000 | −34.542 | −12.269 |
| | | Ar | −5.154 | 4.402 | 31.165 | .751 | −16.291 | 5.983 |
| | O2 | control | 23.405* | 4.402 | 31.165 | .000 | 12.269 | 34.542 |
| | | Ar | 18.251* | 4.150 | 31.214 | .000 | 7.752 | 28.751 |
| | Ar | control | 5.154 | 4.402 | 31.165 | .751 | −5.983 | 16.291 |
| | | O2 | −18.251* | 4.150 | 31.214 | .000 | −28.751 | −7.752 |

| Group | (I) time_min | (J) time_min | Mean Difference (I − J) | Std. Error | df | Sig.[c] | 95% Confidence Interval for Difference[c] Lower Bound | Upper Bound |
|---|---|---|---|---|---|---|---|---|
| control | .00 | 10.00 | 3.939 | 4.448 | 20.296 | .386 | −5.330 | 13.208 |
| | 10.00 | .00 | −3.939 | 4.448 | 20.296 | .386 | −13.208 | 5.330 |
| O2 | .00 | 10.00 | −23.322* | 4.199 | 18.127 | .000 | −32.139 | −14.505 |
| | 10.00 | .00 | 23.322* | 4.199 | 18.127 | .000 | 14.505 | 32.139 |
| Ar | .00 | 10.00 | −6.593 | 4.199 | 18.127 | .134 | −15.410 | 2.224 |
| | 10.00 | .00 | 6.593 | 4.199 | 18.127 | .134 | −2.224 | 15.410 |

Based on estimated marginal means
*The mean difference is significant at the .05 level.
[a]Dependent Variable: CPP.
[c]Adjustment for multiple comparisons: Bonferroni.

TABLE 10

Comparison of oxygen carrying capacity of various PFC-based blood substitutes relative to DAS-h. Because the gas fraction is consumed following i.v. injection, the total volume delivered for DAS-h MBs is significantly less than PFC-based systems.

| Product | % PFC | Oxygen carrying capacity (mL $O_2$ $dL^{-1}$ $mmHg^{-1}$) | Actual volume required to deliver 5 mL $O_2$ (mL) | Actual volume required to deliver 100 mL $O_2$ (mL) |
|---|---|---|---|---|
| Fluosol | 4.0% FDC and 6% FTPA | 8.00E−04 | 822 | 16447 |
| Oxypherol | 20% FTBA | 6.00E−03 | 110 | 2193 |
| Perftoran | 2% FDC and 3% FMCP | 8.00E−04 | 822 | 16447 |
| Oxygent | 8% PFOB and 2% PFDB | 3.10E−02 | 21 | 424 |
| Oxyfluor | 78% PFDCO | 1.80E−03 | 365 | 7310 |
| Oxycyte | 60% TBPCH | 1.70E−02 | 39 | 774 |
| DAS-h | NA | 3.20E−02 | 15 | 312 |
| DAS-h | NA | 6.60E−02 | 5 | 99 |

Example 4: Exemplary Use of Stable Particles as Ultrasound Contrast Agents

Traditional polymeric shelled microparticles have been used as ultrasound contrast agents (UCAs) because of their high stability [33]. However, traditional polymeric shelled UCAs are of low echogenicity, due to the rigidity of the shell; they primarily produce contrast by dampening the sound signals [33]. Instead, UCAs with soft shells, such as lipid microbubbles, generate strong harmonic backscattering when oscillating in response to incident pressure waves. This nonlinear behavior is highly desirable for imaging purposes, because it improves the specificity of microbubble-enhanced ultrasound [34-35]. However, lipid based UCAs greatly lack stability as well as circulating residence time under imaging conditions [36,37]. Accordingly, there is still a need for novel stable particles that can be used as effective ultrasound contrast agents.

Figure 31:
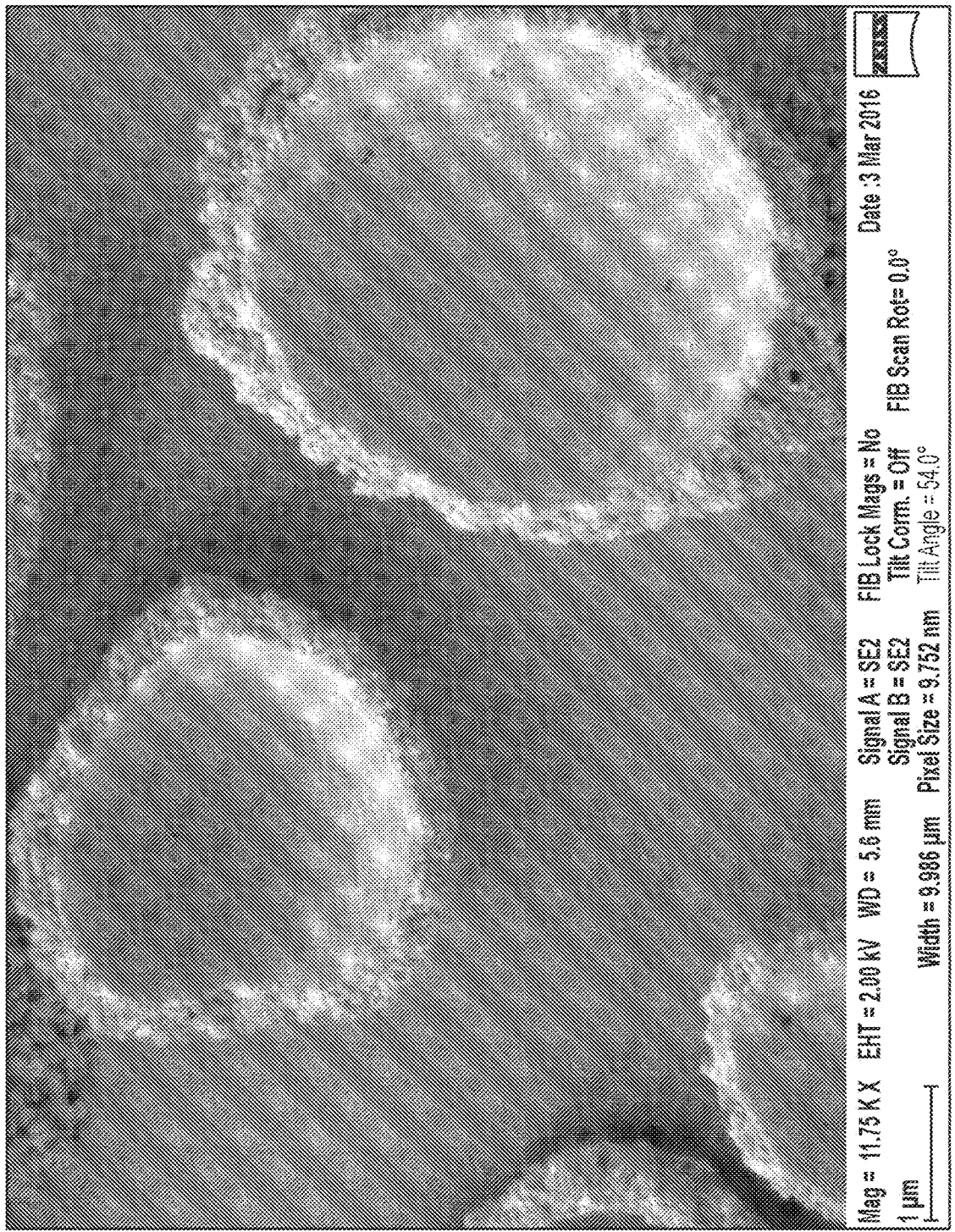
FIG. 31 shows scanning electronic microscopy (SEM) of acetylated dextran (Dex-Ac) MBs, showing the porous shells.

In one aspect, the polymeric stable particles or microbubbles (MBs) described herein produced by interfacial nanoprecipitation can be used as ultrasound-based theranostic agents, e.g., for both imaging and therapeutic uses (e.g., drug delivery, sonoporation). The polymeric MBs produced by interfacial nanoprecipitation possess porous shells (FIG. 31). In some embodiments, gas within the MBs can be capable of oscillating freely to some extent through the interstitial capillaries within the shell, thus exhibiting non-linear behaviors to allow harmonic imaging using ultrasound. In addition, by manipulating the shell compositions, MBs can be designed that cavitate at specific sound pressure, measured by mechanical index (MI).

Figure 32:
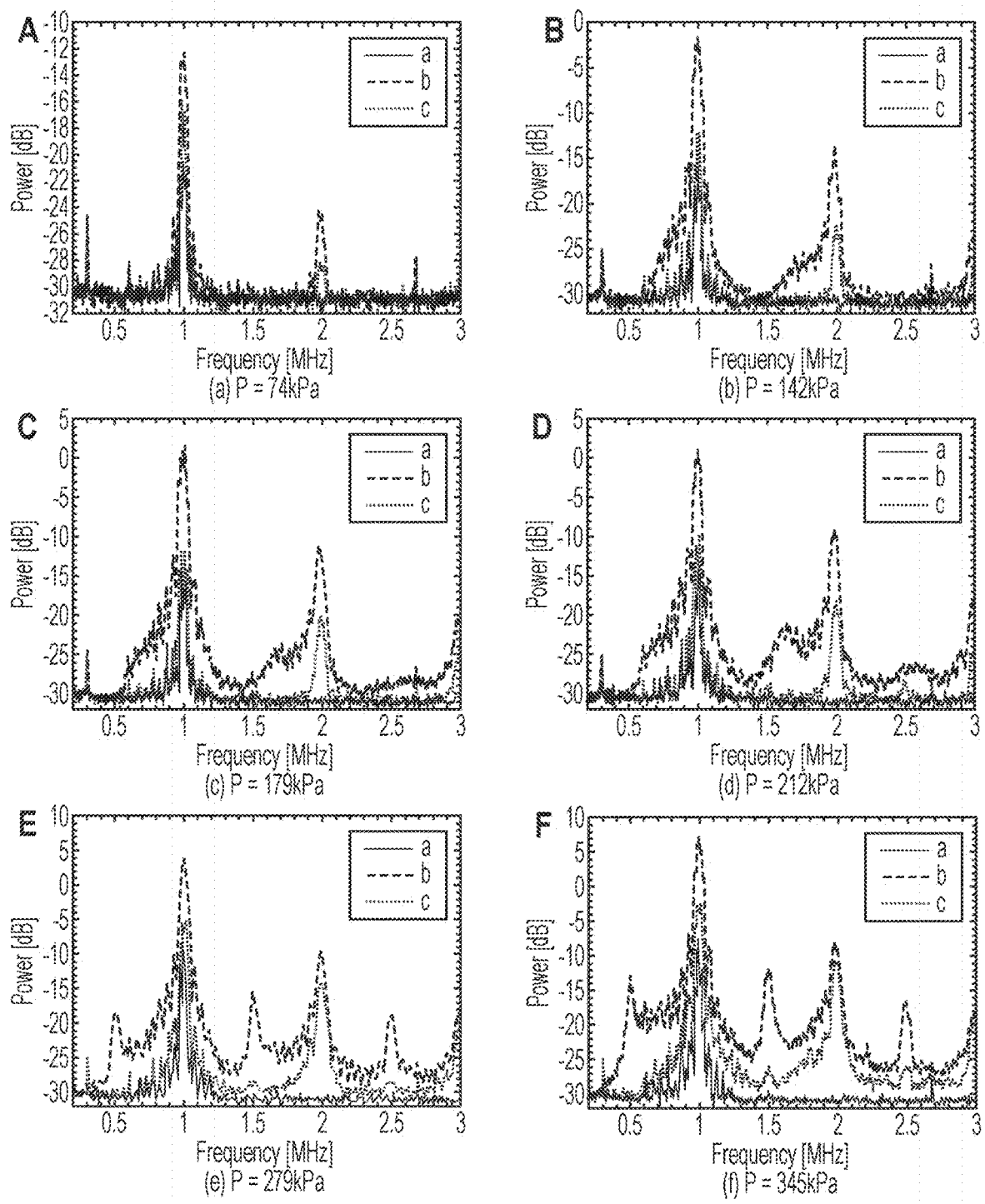
FIG. 32 shows non-linear backscattering of various MBs ($1 \times 10^4$ #/ml) in response to 1 MHz transmitted pulses in water: a, black curve, non-porous hollow octylated-dextran polymer microparticles, b, blue curve, acetylated dextran (Dex-Ac) MBs, c, red curve, acetylated and succinylated dextran (DAS) MBs. Panel A: MI=0.074. Panel B: MI=0.142. Panel C: MI=0.179. Panel D: MI=0.212. Panel E: MI=0.279. Panel F: MI=0.345.
Figure 33:
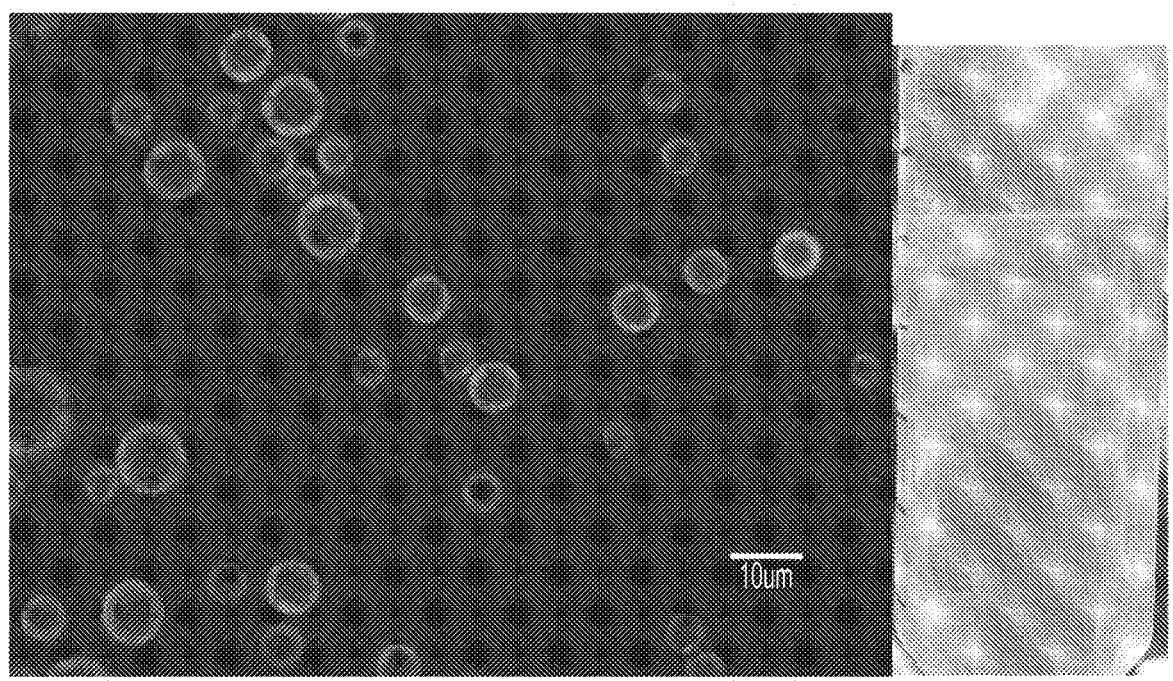
FIG. 33 shows fluorescent microscopic image of Dex-Ac MBs loaded with nile red in the shell, used as a substitute for drug loading (left). (5 wt % relative to polymer were added in solution prior to homogenization). The nile-red loaded Dex-Ac MBs gave a pink color (right).
Figure 34:
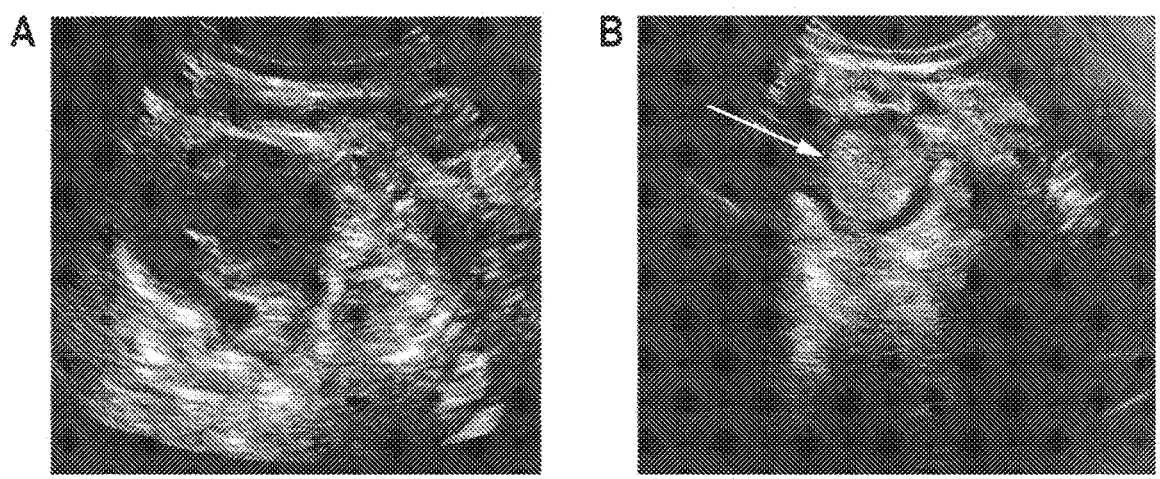
FIG. 34 shows Dex-Ac MBs produced ultrasound contrast in four chamber cardiac view in a rat under harmonic imaging. Panel A shows before injecting MBs. Panel B shows after injecting MBs (1 ml, $1 \times 10^7$#/ml), the arrow indicates the intense signal produced by the circulating MBs.
Figure 35:
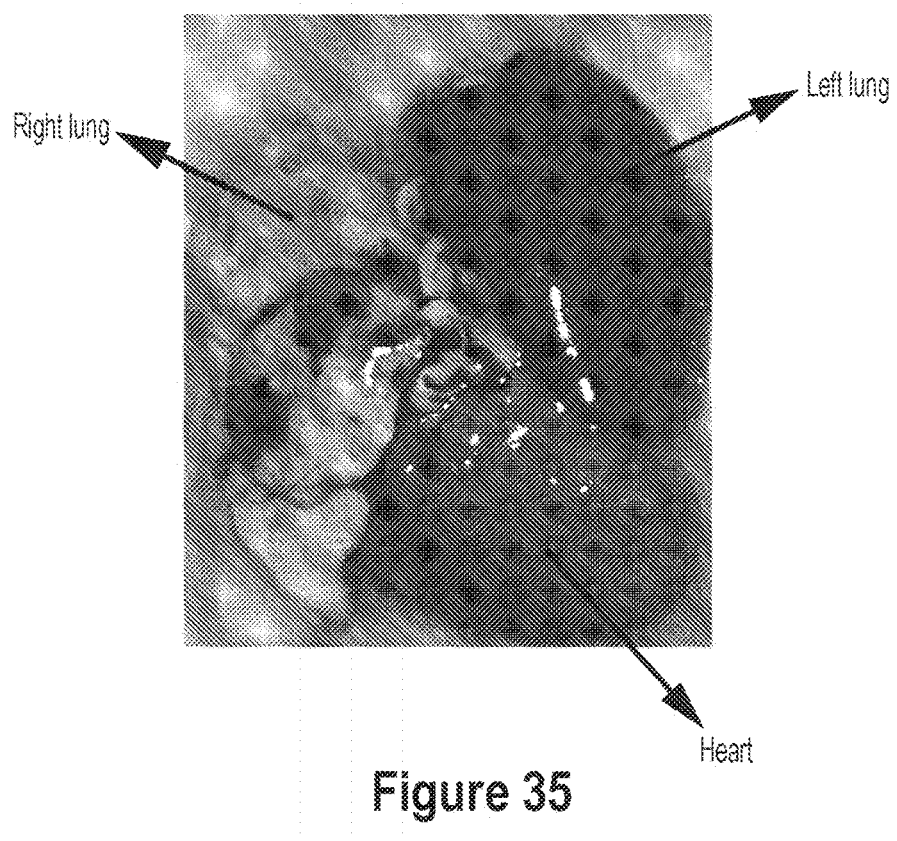
FIG. 35 shows a demonstration of sonoporation by inertia cavitation of Dex-Ac MBs. The left-side lung (dark) was selectively subjected to high MI pulses (1.2) in the presence of circulating MBs (injected with 1 ml, $1 \times 10^7$#/ml) to induce MB cavitation. The resultant hemorrhage indicates the selective sonoporation at target site.

As shown in FIG. 32, the traditional non-porous polymeric microparticles (a) did not exhibit any nonlinear behaviors, due to the rigidity of the shell. In contrast, both porous Dex-Ac MBs (b) and DAS MBs (c) exhibited generated second harmonic in response to the incident pressure wave, at MI as low as 0.07, similar to lipid bubbles [37]. The significant inertia cavitation of Dex-Ac MBs occurred at MI of 0.2 (or, pressure of 212 kPa); where only at much higher MI (i.e. 0.34) inertia cavitation of DAS MBs started to take place. Thus, this demonstrates the ability to design MBs with their specific MI thresholds for cavitation through chemical modifications of polymer precursors. This is advantageous for applications as theranostic MBs. Drugs can be easily loaded into polymeric shells of MBs during fabrication process as shown in FIG. 33, and these MBs can be used as contrast agent (FIG. 34) for imaging below the MI/pressure threshold that causes cavitation. Raising MI at specific location can cavitate MBs thus allowing both drug release from the shells, and also sonoporation that increase the cell permeability at targeted sites (FIG. 35).

Example 5: Oil-Templated Interfacial Precipitation to Produce Nanobubbles

Typically, core-shell particles can be fabricated using perfluorocarbon (PFC)-template based phase separation. This method may require use of multiple components including, e.g., surfactants, porogen, and/or other additives, and it can be challenging to reduce particle size while maintain the desirable morphology, e.g., single core-shell, porous shells, etc.

This Example provides an exemplary method to fabricate stable nano-sized bubbles (NBs). A proper chemical design of a polymer was utilized in the context of a PFC templated phase separation technique, which (1) significantly reduces the surface tension and thus spontaneously forms nano-sized core-shell emulsion droplets, and subsequently undergoes interfacial nanoprecipitation to form porous shells. Thus, no additional components other than oils and water are required.

To demonstrate this, dextran polymers were chemically modified by tuning their amphiphilicity (FIG. 36, Panel A) so that they were able to self-emulsify oils in water and subsequently underwent spontaneous interfacial nanoprecipitation to generate PFC-oil filled core-shell nanoparticles. In some embodiments, the shell comprises nanoprecipitates.

Subsequent freeze-drying yields stable air-filled NBs (FIG. 36, Panel B) with core-shell morphologies (FIG. 36, Panels C and D) and mean diameters of ~350 nm.

In some embodiments, ~470 mg chemically-modified polymers were dissolved in ~16.5 ml dichloromethane (DCM) containing ~0.47 ml perfluorooctylbromide (PFOB). The polymer solution was then added into ~80 ml of water and homogenized for ~1 min at ~9000 rpm, and then poured into ~1.2 L water immediately afterward. After 12 h, the PFC-filled nanoparticles were collected by centrifuging, and washed. Finally, the air-filled NBs were obtained as white powder after freeze-drying for 48 h.

Figure 36:
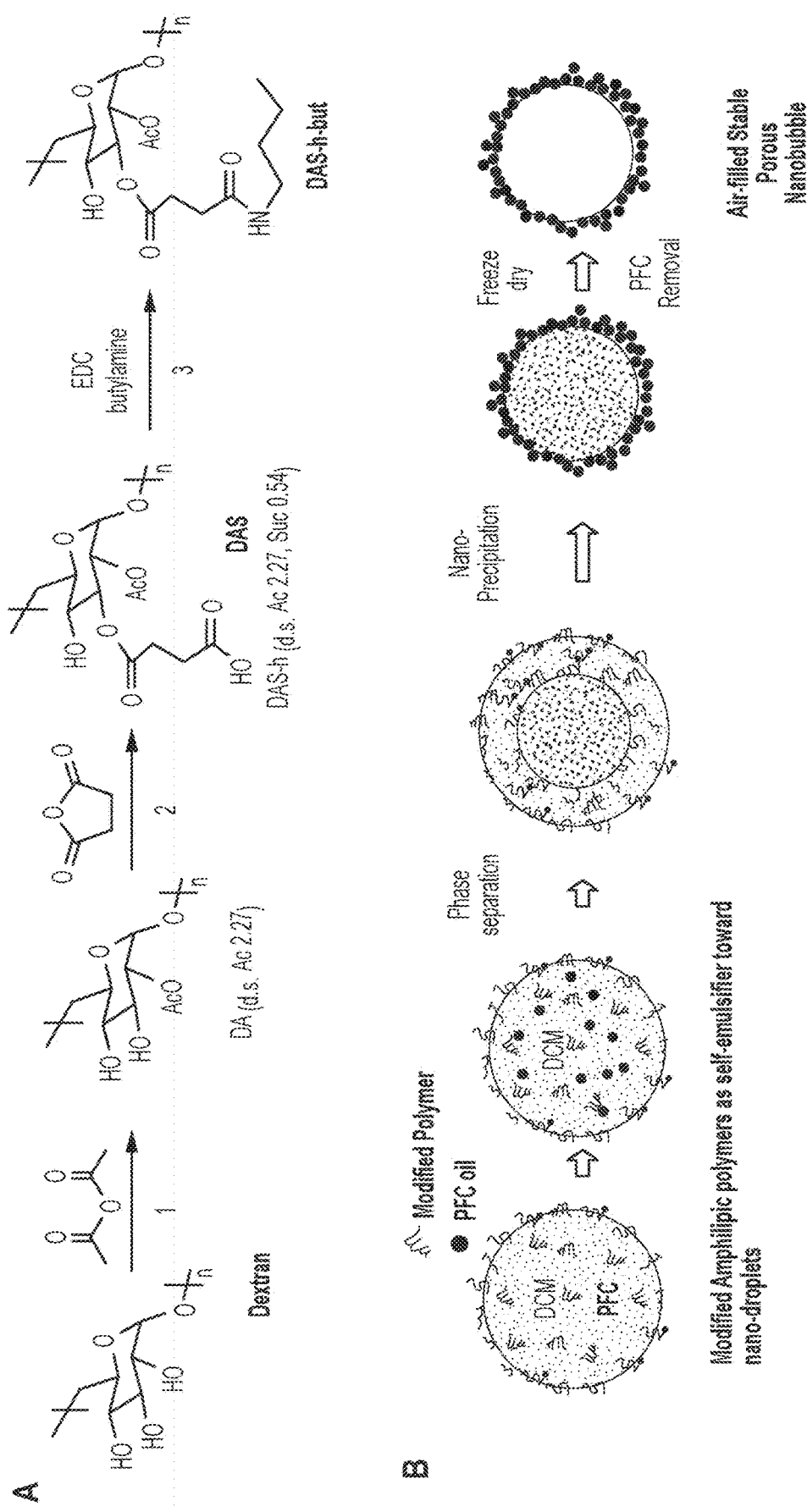
FIG. 36 shows oil-templated interfacial precipitation to produce nano-sized bubbles (NBs). (Panel A) Exemplary polymer synthesis; (Panel B) Schematic showing a general scheme of an exemplary fabrication method for NBs; (Panels C and D) SEM images of porous NBs, scale bar 200 nm; (Panel E) Ultrasonic contrast imaging of air-filled NBs (bright circle); (Panel F) Surfactant (e.g., SDS) caused water-influx into NBs and disappearance of contrast signal.
Figure 36:
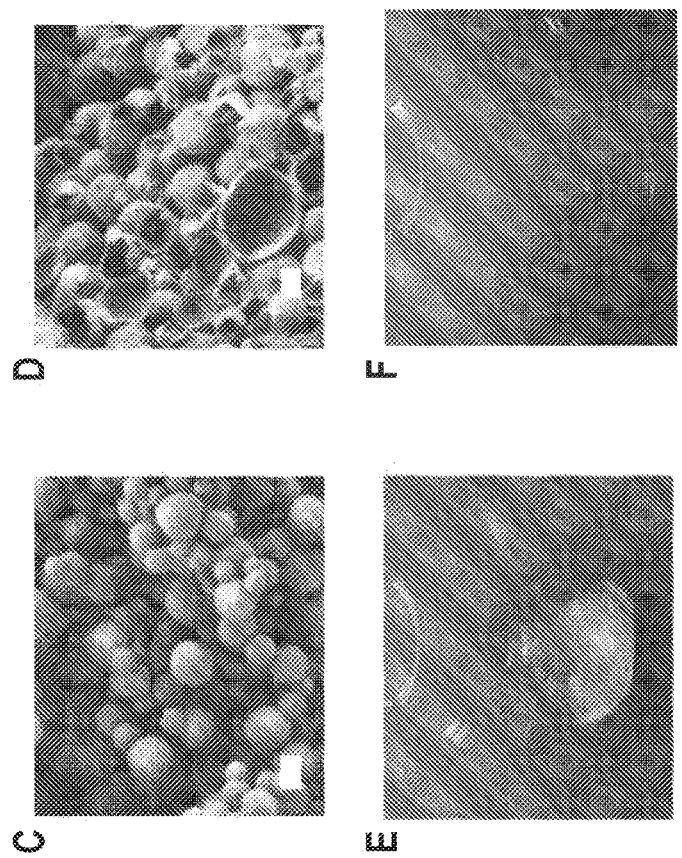

The air-filled NBs can be used for various applications, e.g., as ultrasound contrast agents and blood substitutes for gas delivery. For example, the gas-filled (e.g., air-filled) NBs are echogenic, indicating a core-shell structure, wherein the core encapsulates a gas (FIG. 36, Panel E). The NBs allow harmonic imaging with excellent enhancement of harmonic signal (e.g., up to 20 dB) at low acoustic pressure (e.g., <200 Kpa, f=1 HMz). Thus, the NBs can be used as ultrasound nano-contrast agents.

When gas-filled (e.g., air-filled) NBs were mixed with a solution of a surfactant (e.g., sodium dodecyl sulfate (SDS)), water displaced the gaseous core, rendering them non-echogenic (FIG. 36, Panel F). In some embodiments, absorption of small surfactants can wet air-filled open capillaries in water and cause fluid-influx, this indicates that in some embodiments, NBs can possess highly porous shells that can provide efficient gas exchange. Thus, in some embodiments, the NBs can be injected in vivo to be used as a blood substitute, e.g., as intravascular oxygen delivery carriers.

REFERENCES

1. L. W. Andersen, A. Granfeldt, C. W. Callaway, S. M. Bradley, J. Soar, J. P. Nolan, T. Kurth, M. W. Donnino, Association between tracheal intubation during adult in-hospital cardiac arrest and survival. JAMA 317, 494-506 (2017).
2. J. L. Benoit, D. K. Prince, H. E. Wang, Mechanisms linking advanced airway management and cardiac arrest outcomes. Resuscitation 93, 124-127 (2015).
3. I. Ortega-Deballon, L. Hornby, S. D. Shemie, F. Bhanji, E. Guadagno, Extracorporeal resuscitation for refractory out-of-hospital cardiac arrest in adults: A systematic review of international practices and outcomes. Resuscitation 101, 12-20 (2016).
4. T. Sakamoto, N. Morimura, K. Nagao, Y. Asai, H. Yokota, S. Nara, M. Hase, Y. Tahara, T. Astumi, Extracorporeal cardiopulmonary resuscitation versus conventional cardiopulmonary resuscitation in adults with out-of-hospital cardiac arrest: a prospective observational study. Resuscitation 85, 762-768 (2014).
5. Y. S. Chen, J. W. Lin, H. Y. Yu, W. J. Ko, J. S. Jerng, W. T. Chang, W. J. Chen, S. C. Huang, N. H. Chi, C. H. Wang, L. C. Chen, P. R. Tsai, S. S. Wang, J. J. Hwang, F. Y. Lin, Cardiopulmonary resuscitation with assisted extracorporeal life-support versus conventional cardiopulmonary resuscitation in adults with in-hospital cardiac arrest: an observational study and propensity analysis. Lancet 372, 554-561 (2008).
6. M. S. Link, L. C. Berkow, P. J. Kudenchuk, H. R. Halperin, E. P. Hess, V. K. Moitra, R. W. Neumar, B. J. O'Neil, J. H. Paxton, S. M. Silvers, R. D. White, D. Yannopoulos, M. W. Donnino, Part 7: Adult Advanced Cardiovascular Life Support: 2015 American Heart Association Guidelines Update for Cardiopulmonary Resuscitation and Emergency Cardiovascular Care. Circulation 132, S444-S464 (2015).
7. P. S. Chan, B. K. Nallamothu, H. M. Krumholz, J. A. Spertus, Y. Li, B. G. Hammill, L. H. Curtis, Long-term outcomes in elderly survivors of in-hospital cardiac arrest. N. Engl. J. Med. 368, 1019-1026 (2013).
8. J. N. Kheir, L. A. Scharp., M. A. Borden, E. J. Swanson, A. Loxley, J. H. Reese, K. J. Black, L. A. Velazquez, L. M. Thomson, B. K. Walsh, K. E. Mullen, D. A. Graham, M. W. Lawlor, C. Brugnara, D. C. Bell, F. X. McGowan, Oxygen gas-filled microparticles provide intravenous oxygen delivery. Sci. Transl. Med. 4, 140ra88 (2012).
9. J. A. Feshitan, N. D. Legband, M. A. Borden, B. S. Terry, Systemic oxygen delivery by peritoneal perfusion of oxygen microbubbles. Biomaterials 35, 2600-2606 (2014).
10. R. P. Seekell, A. T. Lock, Y. Peng, A. R. Cole, D. A. Perry, J. N. Kheir, B. D. Polizzotti, Oxygen delivery using engineered microparticles. PNAS 113, 12380-12385 (2016).
11. H. Sakai, H. Horinouchi, Y. Masada, S. Takeoka, E. Ikeda, M. Takaori, K. Kobayashi, E. Tsuchida, Metabolism of hemoglobin-vesicles (artificial oxygen carriers) and their influence on organ functions in a rat model. Biomaterials 25, 4317-4325 (2004).
12. Y. Huang, T. Komatsu, H. Yamamoto, H. Horinouchi, K. Kobayashi, E. Tsuchida, PEGylated albumin-heme as an oxygen-carrying plasma expander: Exchange transfusion into acute anemia rat model. Biomaterials 27, 4477-4483 (2006).
13. J. Bauer, M. Zähres, A. Zellermann, M. Kirsch, F. Petrat, H. de Groot, C. Mayer, Perfluorocarbon-filled poly(lactide-co-gylcolide) nano- and microcapsules as artificial oxygen carriers for blood substitutes: a physico-chemical assessment. J. Microencapsul. 27, 122-132 (2010).
14. B. D. Spiess, Perfluorocarbon emulsions as a promising technology: a review of tissue and vascular gas dynamics. J. Appl. Physiol. 106, 1444-1452 (2009).
15. K. B. Ferenz, I. N. Waack, J. Laudien, C. Mayer, M. Broecker-Preuss, H. de Groot, M. Kirsch. Safety of poly (ethylene glycol)-coated perfluorodecalin-filled poly(lactide-co-glycolide) microcapsules following intravenous administration of high amounts in rats. Results Pharma Sci. 4, 8-18 (2014)
16. H. L. Kutscher, P. Chao, M. Deshmukh, Y. Singh, P. Hu, L. B. Joseph, D. C. Reimer, S. Stein, D. L. Laskin, P. J. Sinko, Threshold size for optimal passive pulmonary targeting and retention of rigid microparticles in rats. J. Control. Release 143, 31-37 (2010).
17. J. Zagorski, J. Debelak, M. Gellar, J. A. Watts, J. A Kline, Chemokines Accumulate in the Lungs of Rats with Severe Pulmonary Embolism Induced by Polystyrene Microspheres. J. Immunol. 171, 5529-5536 (2003).
18. E. Dressaire, R. Bee, D. C. Bell, A. Lips, H. A. Stone, Interfacial polygonal nanopatterning of stable microbubbles. Science 320, 1198-1201 (2008).
19. J. R. Rodriguez, A. Sevilla, C. M. Bazán, J. M. Gordillo. Generation of Microbubbles with Applications to Industry and Medicine. Annu. Rev. Fluid Mech. 47, 405-429 (2015).
20. S. Hornig, T. Heinze, R. C. Becer, U. S. Schubert, Synthetic polymeric nanoparticles by nanoprecipitation. J. Mater. Chem. 19, 3838-3840 (2009).
21. T. Liebert, S. Hornig, S. Hesse, T. Heinze, Nanoparticles on the basis of highly functionalized dextrans. J. Am. Chem. Soc. 127, 10484-10485 (2005).
22. G. Kocak, C. Tuncer, V. Bütün, pH-Responsive polymers. Polym. Chem. 8, 144-176 (2017).
23. B. Macafee, J. P. Campbell, K. Ashpole, M. Cox, F. Matthey, L. Acton, S. M. Yentis, Reference ranges for thromboelastography (TEG®) and traditional coagulation tests in term parturients undergoing caesarean section under spinal anaesthesia. Anaesthesia 67, 741-747 (2012).
24. C. W. Callaway, J. Soar, M. Aibiki, B. W. Böttiger, S. C. Brooks, C. D. Deakin, M. W. Donnino, S. Drajer, W. Kloeck, P. T. Morley, L. J. Morrison, R. W. Neumar, T. C. Nicholson, J. P. Nolan, K. Okada, B. J. O'Neil, E. F. Paiva, M. J. Pan, T. L. Wang, J. Witt, Part 4: Advanced Life Support: 2015 International Consensus on Cardiopulmonary Resuscitation and Emergency Cardiovascular Care Science With Treatment Recommendations. Circulation 132, S84-S145 (2015).
25. H. Song, Y. A. Nor, M. Yu, Y. Yang, J. Zhang, H. Zhang, C. Xu, N. Mitter, C. Yu. Silica nanopollens enhance adhesion for long-term bacterial inhibition. J. Am. Chem. Soc. 138, 6455-6464 (2016)
26. Q. Wang, S. Samitsu, Y. Fujii, C. Yoshikawa, T. Miyazaki, H. Banno, I. Ichinose, Nanoprecipitation for ultrafiltration membranes. J. Polym. Sci., Part B: Polym. Phys. 53, 615-620 (2015).
27. Y. Shen, R. L. Powell, M. L. Longo. Influence of the dissolution rate on the collapse and shedding behavior of monostearin/monopalmitin-rich coated microbubbles. Langmuir, 24, 10035-10040 (2008).
28. J. H. Kilgannon, A. E. Jones, N. I. Shapiro, M. G. Angelos, B. Milcarek, K. Hunter, J. E. Parrillo, S. Trzeciak, Association between arterial hyperoxia following resuscitation from cardiac arrest and in-hospital mortality. JAMA 303, 2165-2171 (2010).
29. A. Brücken, A. Cizen, C. Fera, A. Meinhardt, J. Weis, K. Nolte, R. Rossaint, T. Pufe, G. Marx, M. Fries, Argon reduces neurohistopathological damage and preserves functional recovery after cardiac arrest in rats. Br J Anaesth 110, i106-i112 (2013).
30. R. M. Sutton, S. H. Friess, M. R. Maltese, M. Y. Naim, G. Bratinov, T. R. Weiland, M. Garuccio, U. Bhalala, V. M. Nadkarni, L. B. Becker, R. A. Berg, Hemodynamic-directed cardiopulmonary resuscitation during in-hospital cardiac arrest. Resuscitation 85, 983-986 (2014).
31. G. Nichol, et al. Trial of Continuous or Interrupted Chest Compressions during CPR. N. Engl. J. Med. 373, 2203-2214 (2015).
32. P. N. Span, J. Bussink, J. H. A. M. Kaanders, Engineered microparticles delivering oxygen to enhance radiotherapy efficacy. PNAS 113, E8009 (2016).
33. Paefgen V. et al, Evolution of contrast agents for ultrasound imaging and ultrasound-mediated drug delivery. *Front Pharmocol.* 2015, 6, 197.
34. Burns P. N. Harmonic imaging with ultrasound contrast agents. *Clin. Radiol.* 1996, 51, 50-55.
35. De Jong N., et al, Basic acoustic properties of microbubbles. *Echocardiography* 2002, 19, 229-240.
36. Teraphongphom, N. et al, Nanoparticle loaded polymeric microbubbles as contrast agents for multimodal imaging. *Langmuir,* 2015, 31, 11858-11867.
37. Tsao, N. H. and Hall, E. A. H. Enzyme-degradable hydrib polymer/silica microbubbles as ultrasound contrast agents. *Langmuir,* 2016, 32, 6534-6543.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A composition comprising a stable particle having a shell surrounding a gas core,
    wherein the shell includes a release trigger,
    wherein the release trigger is a pH-responsive trigger,
    wherein the shell comprises succinylated and acetylated dextran (Dex-Ac-Suc), and
    wherein the succinyl moiety of the Dex-Ac-Suc is the pH-responsive trigger.

2. The composition of claim 1, wherein the shell comprises nanoparticle aggregates.

3. The composition of claim 2, wherein the stable particle is formed by nanoprecipitation of an amphiphilic polymer comprising the release trigger at an air/liquid interface to form the shell.

4. The composition of claim 3, wherein the amphiphilic polymer comprises acetylated dextran (Dex-Ac).

5. The composition of claim 2,
    wherein the nanoparticle aggregates comprise primary particles, each primary particle having an average diameter of 50 nm or less, and wherein the shell has a thickness of 10-280 nm.

6. The composition of claim 1, wherein the stable particle is formed by nanoprecipitation of an amphiphilic polymer comprising the release trigger at an air/liquid interface to form the shell.

* * * * *